(12) United States Patent
Markert

(10) Patent No.: US 12,064,452 B2
(45) Date of Patent: *Aug. 20, 2024

(54) CULTURED THYMUS TISSUE TRANSPLANTATION PROMOTES DONOR-SPECIFIC TOLERANCE TO ALLOGENEIC SOLID ORGAN TRANSPLANTS

(71) Applicant: Duke University, Durham, NC (US)

(72) Inventor: Mary Louise Markert, Durham, NC (US)

(73) Assignee: Duke University, Durham, NC (US)

( * ) Notice: Subject to any disclaimer, the term of this patent is extended or adjusted under 35 U.S.C. 154(b) by 125 days.

This patent is subject to a terminal disclaimer.

(21) Appl. No.: 17/486,045

(22) Filed: Sep. 27, 2021

(65) Prior Publication Data

US 2022/0079989 A1 Mar. 17, 2022

Related U.S. Application Data

(60) Division of application No. 16/283,007, filed on Feb. 22, 2019, now Pat. No. 11,819,520, which is a continuation of application No. PCT/US2019/019137, filed on Feb. 22, 2019.

(60) Provisional application No. 62/634,377, filed on Feb. 23, 2018.

(51) Int. Cl.

| | | |
|---|---|---|
| *A61K 38/13* | (2006.01) | |
| *A01N 1/02* | (2006.01) | |
| *A61K 9/00* | (2006.01) | |
| *A61K 31/343* | (2006.01) | |
| *A61K 31/436* | (2006.01) | |
| *A61K 31/573* | (2006.01) | |
| *A61K 35/26* | (2015.01) | |
| *A61K 35/34* | (2015.01) | |
| *A61K 38/17* | (2006.01) | |
| *A61K 39/00* | (2006.01) | |
| *A61K 39/395* | (2006.01) | |
| *A61L 27/38* | (2006.01) | |
| *A61P 37/06* | (2006.01) | |
| *C07K 16/28* | (2006.01) | |
| *G01N 33/50* | (2006.01) | |
| *A61K 35/12* | (2015.01) | |

(52) U.S. Cl.
CPC ............ *A61K 35/26* (2013.01); *A01N 1/0284* (2013.01); *A61K 9/0019* (2013.01); *A61K 31/343* (2013.01); *A61K 31/436* (2013.01); *A61K 31/573* (2013.01); *A61K 35/34* (2013.01); *A61K 38/13* (2013.01); *A61K 38/1722* (2013.01); *A61K 39/0008* (2013.01); *A61K 39/3955* (2013.01); *A61L 27/3804* (2013.01); *A61L 27/3895* (2013.01); *A61P 37/06* (2018.01); *C07K 16/2893* (2013.01); *G01N 33/5047* (2013.01); *A61K 2035/122* (2013.01); *A61L 2430/20* (2013.01); *A61L 2430/40* (2013.01); *C07K 2317/24* (2013.01); *G01N 2800/245* (2013.01)

(58) Field of Classification Search
None
See application file for complete search history.

(56) References Cited

U.S. PATENT DOCUMENTS

| | | |
|---|---|---|
| 5,614,187 A | 3/1997 | Sachs |
| 5,624,823 A | 4/1997 | Sachs et al. |
| 5,658,564 A | 8/1997 | Sykes et al. |
| 5,876,708 A | 3/1999 | Sachs |
| 6,296,846 B1 | 10/2001 | Sachs et al. |
| 6,911,220 B1 | 6/2005 | Sachs |
| 7,173,016 B2 | 2/2007 | DiMartino et al. |
| 8,933,194 B2 | 1/2015 | Yang et al. |
| 10,612,092 B2 | 4/2020 | Suthanthiran |
| 2004/0086508 A1 | 5/2004 | Skurkovich et al. |
| 2006/0110387 A1 | 5/2006 | Brunetta |
| 2006/0147428 A1 | 7/2006 | Sachs |
| 2007/0202085 A1 | 8/2007 | Hu et al. |
| 2009/0041854 A1 | 2/2009 | Markert |
| 2012/0263737 A1 | 10/2012 | Taylor et al. |
| 2015/0110754 A1 | 4/2015 | Bai |
| 2020/0012845 A1 | 1/2020 | Tracy et al. |

FOREIGN PATENT DOCUMENTS

| | | |
|---|---|---|
| JP | 2002-542174 A | 12/2002 |
| WO | 2000/062657 A2 | 10/2000 |
| WO | 2009/120341 A2 | 10/2009 |
| WO | 2012/092578 A1 | 7/2012 |
| WO | 2019/0165195 A1 | 8/2019 |

OTHER PUBLICATIONS

"Anti-Cytokeratin AE1/AE3 Antibody, recognizes acidic & basic cytokeralins, clone AE1/AE3", www.sigmaaldrich.com/US/en/producl/mm/mab3412, 8 pages.

"Anti-pan Cytokeratin antibody [AE1/AE3] (ab27988)", www.abcam.com/pan-cytokeralin-anlibody-ae1ae3-ab27988.html, 4 pages.

"Cytokeratin, Multi (AE1/AE3) Antibody—MCK Immunohistochemical Slain", https://shop.leicabiosystems.com/us/ihc-sh/ihc-primary-antibodies/pid-cytokeralin-multi-ae1-ae3, 3 pages.

"Keratin, type I cytoskelelal 14 [*Homo sapiens*]," 3 pages. www.ncbi.nlm.gov/protein/NP_000517.3.

Ariyoshi, et al, "Antibody Reactivity with New Antigens Revealed in Multitransgenic Triple Knockout Pigs May Cause Early Loss of Pig Kidneys in Baboons", Xenotransplantation. 2021;28:e12642. 1 of 9 pages.

(Continued)

*Primary Examiner* — G. R. Ewoldt
(74) *Attorney, Agent, or Firm* — Hamilton, Brook, Smith & Reynolds, P.C.

(57) ABSTRACT

Methods and compositions for promoting donor-specific tolerance and immunocompetence to a recipient of a solid organ transplant, by implanting an allogeneic solid organ in a recipient in need of a solid organ transplant and further comprising surgical implantation of a tissue-engineered allogeneic cultured postnatal thymus tissue product in the recipient of a solid organ from a donor.

12 Claims, 37 Drawing Sheets
(26 of 37 Drawing Sheet(s) Filed in Color)

(56) References Cited

OTHER PUBLICATIONS

Armstrong, et al., Analysis of Primate Renal Allografts After T-Cell Depletion with Anti-CD3-CRM9. Transplantation, Jul. 15, 1998;66(1):5-13. 20 Pages.
Bhagra, et al., "Cardiac Transplantation: Indications, Eligibility and Current Outcomes", Heart (2019);105:252-260.
Biron-Pain, K. et al. "Expression and functions of galectin-7 in human and murine melanomas", PLoS One May 2013, vol. 8, Issue 5, e63307, 10 pages.
Black, et al., "Solid Organ Transplantation in the 21st Century", Ann Transl Med (2018) 6(20):409, 12 pages.
Braunberger, et al., "Tolerance Induced Without Immunosuppression in a T-Lymphocyte Suicide-Gene Therapy Cardiac Allograft Model in Mice", J Thorac Cardiovasc Surg. (Jan. 2000); 119(1):46-51.
Brown, et al, "A Humanized Mouse Model Generated Using Surplus Neonatal Tissue" Stem Cell Report, vol. 10, Issue 4, Apr. 10, 2018, pp. 1175-1183.
Bunting MD, Comerford I, McColl SR (2011) Finding their niche: chemokines directing cell migration in the thymus mmunol Cell Biol 89:185-196 doi:10.1038/icb.2010.142.
Duggan, et al,"Progress Towards Xenogenic Tolerance", www.co-transplantation.com, vol. 25, No. 5, Oct. 2020, pp. 457-463.
Fitzhugh DJ, Shan S, Dewhirst MW, Hale LP (2008) Bromelain treatment decreases neutrophil migration to sites of inflammation Clin Immunol 128:66-74 doi:10.1016/j.clim.2008.02.015.
Flores KG, Li J, Sempowski GD, Haynes BF, Hale LP (1999) Analysis of the human thymic perivascular space during aging J Clin Invest 104:1031-1039 doi:10.1172/JCI7558.
Griesemer AD, et al. "Results of gal-knockout porcine thymokidney xenografts," Am J Transplant 9:2669-2678 (2009).
Gruver AL, Hudson LL, Sempowski GD (2007) Immunosenescence of ageing J Pathol 211 :144-156 doi:10.1002/path.2104.
Jafezi-Moghadam A, Thomas KL, Prorock AJ, Huo Y, Ley K (2001) L-selectin shedding regulates leukocyte recruitment J Exp Med 193:863-872 doi:10.1084/jem.193.7.863.
Hale, LP et al. "Histopathologic assessment of cultured human thymus", PLOS One, Mar. 24, 2020, 20 pages.
Hammerman, Marc R., "Xenotransplantation in the Kidney: A Historical Perspective", Kidney Development, Disease, Repair and Regeneration, Chapter 37, pp. 507-519 (2016).
Hernandez-Lopez C, Varas A, Sacedon R, Jimenez E, Munoz JJ, Zapata AG, Vicente A (2002) Stromal cell-derived actor 1/CXCR4 signaling is critical for early human T-cell development Blood 99:546-554 doi:10.1182/blood.v99.2.546.
Hong R, Moore AL (1996) Organ culture for thymus transplantation Transplantation 61 : 444-448 :doi: 10 .1097 /00007890-199602150-00023.
Hu Z, Lancaster JN, Ehrlich LI (2015) The Contribution of Chemokines and Migration to the Induction of Central Tolerance in the Thymus Front Immunol 6:398 doi:10.3389/fimmu.2015.00398.
Ito R et al. (2017) Late Effects of Exposure to Ionizing Radiation and Age on Human Thymus Morphology and Functior Radial Res 187:589-598 doi:10.1667/RR4554.1.
Ivetic A, Hoskins Green HL, Hart SJ (2019) L-selectin: A Major Regulator of Leukocyte Adhesion, Migration and Signaling Front Immunol 10:1068 doi:10.3389/fimmu.2019.01068.
J.O., et al, "Heart En Bloc Thymus Cotransplantation in NHPs-ATC Abstracts", ATC Meeting Abstracts, Jan. 5, J021, https://atcmeetingabstracts.com/abstracl/heart-en-bloc-thymus-cotransplantation-in-nhps/, 4 pages.
Johnston, et al, "Heart and En-bloc Thymus Transplantation in Miniature Swine", Cardiothoracic Transplantation, The Journal of Thoracic and Cardiovascular Surgery, vol. 130, No. 2, pp. 554-559 (Aug. 2005).
Jones, et al., "Assessing Solid Organ Donors and Monitoring Transplant Recipients or Human Immunodeficiency Virus, Hepatitis B Virus, and Hepatitis C Virus Infection—U.S. Public Health Service Guideline, 2020" MMWR, vol. 69, No. 4, Jun. 26, 2020, 20 pages.
Kawai, et al., "CD154 Blockade For Induction of Mixed Chimerism and Prolonged Renal Allograft Survival in Nonhuman Primates", Am J Transplant 4: 1391-1398 (2004).
Kawai, et al., Effect of Mixed Hematopoietic Chimerism on Cardiac Allograft Survival in Cynomolgus Monkeys. Transplantation 73: 1757-1764 (2002). 8 pages.
Kawai, et al., "HLA-Mismatched Renal Transplantation Without Maintenance Immunosuppression," N Engl J Med 358:353-361 (2008).
Kawai, et al., "Long-term Outcome and Alloantibody Production in a Non-Myeloablative Regimen for Induction of Renal Allograft Tolerance", Transplantation (1999) 68: 1767-1775. 16 pages.
Kawai, et al., "Mixed Allogeneic Chimerism and Renal Allograft Tolerance in Cynomolgus Monkeys", Transplantation (1995) 59:256-262.
Kirk et al., "Optimization of De Novo Belatacept-based Immunosuppression Administered to Renal Transplant Recipients", Am J Transplant; 21:1691-1698 (2021).
Kozai Met al. (2017) Essential role of CCL21 in establishment of central self-tolerance in T cells J Exp Med J14:1925-1935 doi:10.1084/jem.20161864.
Kuwabara I et al. (2002) Galectin-7 (PIG1) exhibits pro-apoptotic function through JNK activation and mitochondrial cytochrome c release J Biol Chem 277:3487-3497 doi:10.1074/jbc.M109360200.
Lambrigts, et al, "Implantation Of Autologous Thymus Into The Heart Prior To Procurement", Transplantation, vol. 66, No. 6, pp. 810-814 (Sep. 27, 1998).
Lancaster JN, Li Y, Ehrlich UR. Chemokine-Mediated Choreography of Thymocyte Development and Selection. Trends Immunol. 2018;39(2):86-98. Epub Nov. 23, 2017. doi: 10.1016/j.il.2017.10.007. PubMed PMID: 29162323; PMCID: PMC5800975.
Le PT, Kurtzberg J, Brandl SJ, Niedel JE, Haynes BF, Singer KH (1988) Human thymic epithelial cells produce Jranulocyte and macrophage colony-stimulating factors J Immunol 141 : 1211-1217.
Liu C et al. (2005) The role of CCL21 in recruitment of T-precursor cells to fetal thymi Blood 105:31-39 doi:10.1182/blood-2004-04-1369.
Lkhagvasuren E, Sakata M, Ohigashi I, Takahama Y (2013) Lymphotoxin beta receptor regulates the development of CCL21-expressing subset of postnatal medullary thymic epithelial cells J Immunol 190:5110-5117 doi:10.4049/immunol.1203203.
LoCascio SA, et al., "Mixed Chimerism, Lymphocyte Recovery, and Evidence for Early Donor-specific Unresponsiveness in Patients Receiving Combined Kidney and Bone Marrow Transplantation to Induce Tolerance", Transplantation. Dec. 27, 2010;90(12):1607-15.
Lu, et al. "Cardiac Allograft Tolerance Induced by Isogeneic CD4+ CD25+ Regulatory T Cells", Exp Clin Transplant, Apr. 2012;12(2):133-8.
Madariaga, et al, "Organ-specific Differences in Achieving Tolerance", Curr Opin Organ Transplant. (Aug. 2015); 20 4): 392-399, 16 pages.
Magee CN, et al., "Notch-1 Inhibition Promotes Immune Regulation in Transplantation via Regulatory T Cell-Dependent Mechanisms", Circulation. Sep. 9, 2019; 140(10):846-863.
Matthews, et al, "New-Onset Diabetes Mellitus Aller Transplantation in a Cynomolgus Macaque (*Macaca fasicularis*)", Comparitive Medicine, American Association for Laboratory Animal Science, vol. 65, No. 4, pp. 352-356, Aug. 2015.
Menard, et al, "Immunosuppression in Experimental Heart Transplantation", Organtransplantation in Rats and Mice, Chapter 38, pp. 375-384 (1998).
Ashton-Rickardt PG, et al., "Peptide Contributes To The Specificity of Positive Selection of CD8+ T Cells in the Thymus," Cell. 1993; 73(5):1041-1049. doi:10.1016/0092-8674(93)90281-t.
Atkinson K, et al., Thymus Transplantation After Allogeneic Bone Marrow Graft to Prevent Chronic Graft-Versus-Host Disease in Humans, Transplantation. 1982;33(2):168-173. http://www.ncbi.nlm.nih.gov/pubmed/7036469. Accessed Sep. 8, 2018.

(56) References Cited

OTHER PUBLICATIONS

Born W, et al., "Expression and Role of the T Cell Receptor in Early Thymocyte Differentiation In Vitro," J Immunol. 1987; 138(4):999-1008. http://www.ncbi.nlm.nih.gov/pubmed/3492547. Accessed Sep. 17, 2018.

Brent L, et al., "Transplantation Tolerance," Br Med Bull. 1976; 32(2):101-106. http://www.ncbi.nlm.nih.gov/pubmed/60159. Accessed Sep. 17, 2018.

Campos L, et al., "Prolonged Survival of Rat Orthotopic Liver Allografts After Intrathymic Inoculation of Donor-Strain Cells," Transplantation. 1993; 55(4):866-870. http://www.ncbi.nlm.nih.gov/pubmed/8475562. Accessed Sep. 18, 2018.

Chinn IK, et al., "Long-term Tolerance to Allogeneic Thymus Transplants in Complete DiGeorge Anomaly," Clin Immunol. 2008 ;126(3):277-281. doi:10.1016/j.clim.2007.11.009.

Chowdhury NC, et al., "Acquired Systemic Tolerance to Rat Cardiac Allografts Induced by Intrathymic Inoculation of Synthetic Polymorphic MHC Class I Allopeptides," Transplantation. 1996; 62(12):1878-1882. http://www.ncbi.nlm.nih.gov/pubmed/8990380. Accessed Sep. 18, 2018.

Ciupe SM, et al., "The Dynamics of T-Cell Receptor Repertoire Diversity Following Thymus Transplantation For DiGeorge Anomaly," PLoS Comput Biol. Jun. 2009; 5(6):e1000396. doi: 10.1371/journal.pcbi.1000396. Epub Jun. 12, 2009. PubMed PMID: 19521511; PubMed Central PMCID: PMC2690399.

Hale et al., "Corticosteroids Regulate Epithelial Cell Differentiation and Hassall Body Formation in the Human Thymus", J Immunol. Jan. 1, 2004; 172(1):617-24.

Hall BM, et al., The Cellular Basis of Allograft Rejection In Vivo. I. The Cellular Requirements For First-set Rejection of Heart Grafts, J Exp Med. 1978; 148(4):878-889. http://www.ncbi.nlm.nih.gov/pubmed/359750. Accessed Sep. 5, 2018.

Hall BM, et al., "The Cellular Basis of Allograft Rejection In Vivo. II. The Nature of Memory Cells Mediating Second Set Heart Graft Rejection," J Exp Med. 1978; 148(4):890-902. http://www.ncbi.nlm.nih.gov/pubmed/359751. Accessed Sep. 17, 2018.

Hornik CP, et al., "Successful Extracorporeal Membrane Oxygenation For Respiratory Failure in an Infant with DiGeorge Anomaly, Following Thymus Transplantation," Respir Care. Jun. 2011; 56(6):866-70. doi: 10.4187/respcare.01051. Epub Feb. 11, 2011. PubMed PMID: 21333090.

Isakovic K, et al., "Role of the Thymus in Tolerance. I. Tolerance to Bovine Gamma Globulin in Thymectomized, Irradiated Rats Grafted with Thymus From Tolerant Donors," J Exp Med. 1965; 122(6):1103-1123. http://www.ncbi.nlm.nih.gov/pubmed/4159035. Accessed Sep. 5, 2018.

Kappler JW, et al., "T Cell Tolerance by Clonal Elimination in the Thymus," Cell. 1987; 49(2):273-280. http://www.ncbi.nlm.nih.gov/pubmed/3494522. Accessed Sep. 17, 2018.

Kawai T, et al "Tolerance," Transplantation. 2014; 98(2): 117-121. doi:10.1097/TP.0000000000000260.

Kisielow P, et al., "Positive Selection of Antigen-Specific T Cells in Thymus by Restricting MHC Molecules," Nature. 1988; 335(6192):730-733. doi:10.1038/335730a0.

Kwun J, et al., "Thymus Co-Transplantation Promotes Donor-Specific Tolerance in Allogeneic Heart Transplantation—ATC Abstracts." In: Abstract A423. ; 2018. https://atcmeetingabstracts.com/abstract/thymus-co-transplantation-promotes-donor-specific-tolerance-in-allogeneic-heart-transplantation/. Accessed Oct. 9, 2018.

Lund LH, et al., "The Registry of the International Society for Heart and Lung Transplantation: Thirty-first Official Adult Heart Transplant Report—2014; Focus Theme: Retransplantation," J Hear Lung Transplant. 2014; 33(10):996-1008. doi:10.1016/j.healun.2014.08.003.

Lynch HE, et al., "Thymic Involution and Immune Reconstitution," Trends Immunol. 2009; 30(7):366-373. doi:10.1016/j.t.2009.04.003.

MacDonald HR, et al., "T-Cell Receptor VB Use Predicts Reactivity and Tolerance to MIsα-Encoded Antigens," Nature. 1988; 332(6159):40-45. doi:10.1038/332040a0.

Markert ML, et al, "Thymus Transplantation in Complete DiGeorge Syndrome: Immunologic and Safety Evaluations in 12 Patients," Blood. Aug. 1, 2003; 102(3):1121-30.

Markert et al., "Complete DiGeorge syndrome: Development of Rash, Lymphadenopathy, and Oligoclonal T Cells in 5 Cases," J Allergy Clin Immunol. Apr. 2004; 113(4):734-41.

Markert ML, et al., "Review of 54 Patients with Complete DiGeorge Anomaly Enrolled in Protocols For Thymus Transplantation: Outcome of 44 Consecutive Transplants," Blood May 15, 2007; 109(10):4539-4547.

Markert ML, et al., "Use of Allograft Biopsies To Assess Thymopoiesis After Thymus Transplantation," J Immunol. May 1, 2008; 180(9):6354-6364.

Markert ML,et al., "Thymus Transplantation in Complete DiGeorge Anomaly." Immunol Res. 2009; 44(1-3):61-70. doi: 10.1007/s12026-008-8082-5. PubMed PMID: 19066739; PubMed Central PMCID: PMC4951183.

Maron BJ, et al., "American College of Cardiology/European Society of Cardiology Clinical Expert Consensus Document on Hypertrophic Cardiomyopathy," J Am Coll Cardiol. 2003; 42(9):1687-1713. doi: 10.1016/S0735-1097(03)00941-0.

Maron BJ, et al., "Sudden Deaths in Young Competitive Athletes," Circulation. 2009; 119(8):1085-1092. doi:10.1161/CIRCULATIONAHA.108.804617.

Mehra MR, et al., "The 2016 International Society for Heart Lung Transplantation Listing Criteria For Heart Transplantation: A 10-year Update," J Hear Lung Transplant. 2016; 35(1):1-23. doi:10.1016/j.healun.2015.10.023.

Menard MT, et al., Composite "Thymoheart" Transplantation Improves Cardiac Allograft Survival. Am J Transplant. 2004; 4(1):79-86. doi:10.1046/j.1600-6143.2003.00295.x.

Ohzato H, et al., "Induction of Specific Unresponsiveness (tolerance) To Skin Allografts by Intrathymic Donor-Specific Splenocyte Injection in Antilymphocyte Serum-Treated Mice," Transplantation. 1992; 54(6):1090-1095. http://www.ncbi.nlm.nih.gov/pubmed/1465774. Accessed Sep. 18, 2018.

Perico N, et al., "Thymus-Mediated Immune Tolerance to Renal Allograft Is Donor But Not Tissue Specific," J Am Soc Nephrol. 1991; 2(6):1063-1071. http://www.ncbi.nlm.nih.gov/pubmed/1777586. Accessed Sep. 18, 2018.

Posselt AM, et al., "Induction of Donor-Specific Unresponsiveness by Intrathymic Islet Transplantation," Science. 1990;249(4974):1293-1295. http://www.ncbi.nlm.nih.gov/pubmed/2119056. Accessed Sep. 18, 2018.

Remuzzi G, et al., "Kidney Graft Survival in Rats Without Immunosuppressants After Intrathymic Glomerular Transplantation," Lancet (London, England). 1991; 337(8744):750-752. http://www.ncbi.nlm.nih.gov/pubmed/1672390. Accessed Sep. 18, 2018.

Rota IA et al., FOXN1 deficiency nude severe combined immunodeficiency. Orphanet Journal of Rare Diseases. 2017; 12:6.

Sayegh MH, et al., "Thymic Recognition of Class II Major Histocompatibility Complex Allopeptides Induces Donor-Specific Unresponsiveness To Renal Allografts," Transplantation. 1993; 56(2):461-465. http://www.ncbi.nlm.nih.gov/pubmed/7689263. Accessed Sep. 18, 2018.

Spitzweg C, et al., "Expression of Thyroid-Related Genes in Human Thymus," Thyroid. 1999;9(2):133-141. doi:10.1089/thy.1999.9.133.

Sprent J, et al., "T Cell Selection in the Thymus," Immunol Rev. 1988; 101:173-190. http://www.ncbi.nlm.nih.gov/pubmed/3280468. Accessed Sep. 17, 2018.

Taub DD, et al., "Insights Into Thymic Aging and Regeneration," Immunol Rev. 2005; 205(1):72-93. doi:10.1111/i.0105-2896.2005.00275.x.

Waer M, et al., "Induction of Transplantation Tolerance in Mice Across Major Histocompatibility Barrier by Using Allogeneic Thymus Transplantation and Total Lymphoid Irradiation," J Immunol. 1990; 145(2):499-504. http://www.ncbi.nlm.nih.gov/pubmed/2142180. Accessed Sep. 10, 2018.

Yamada K, et al., "Thymic Transplantation in Miniature Swine. I. Development and Function of the "Thymokidney,"" Transplantation. 1999; 68(11):1684-1692. http://www.ncbi.nlm.nih.gov/pubmed/10609944. Accessed Sep. 24, 2018.

(56) References Cited

OTHER PUBLICATIONS

Yamada K, et al., "Thymic Transplantation in Miniature Swine. II. Induction of Tolerance by Transplantation of Composite Thymokidneys To Thymectomized Recipients," J Immunol. 2000; 164(6):3079-3086. http://www.ncbi.nlm.nih.gov/pubmed/10706697. Accessed Sep. 24, 2018.
Zinkernagel RM, et al., "Cytotoxic T Cells Learn Specificity For Self H-2 During Differentiation in the Thymus," Nature. 1978; 271(5642):251-253. http://www.ncbi.nlm.nih.gov/pubmed/304527. Accessed Sep. 17, 2018.
Amatuni, et al., "Newborn Screening for Severe Combined Immunodeficiency and T-cell Lymphopenia in California, 2010-2017", Pediatrics. Feb. 2019;143(2).
Albuquerque, et al., "Human FOXN1-Deficiency Is Associated With αβ Double-Negative and FoxP3+ T-Cell Expansions That Are Distinctly Modulated Upon Thymic Transplantation." PLoS One, 2012; 7(5):e37042.
Chinn, et al., "Induction Of Tolerance To Parental Parathyroid Grafts Using Allogeneic Thymus Tissue In Patients With DiGeorge Anomaly", J Allergy Clin Immunol. Jun. 2011;127(6):1351-5.
Chinn, et al., "Thymus Transplantation Restores The Repertoires of Forkhead Box Protein 3 (FoxP3)+ and FoxP3-T Cells In Complete DiGeorge Anomaly." Clin Exp Immunol. Jul. 2013;173(1):140-9.
Heimall, et al., "Diagnosis of 22q11.2 Deletion Syndrome and Artemis Deficiency In Two Children With T-B-NK+ Immunodeficiency. " J Clin Immunol. Oct. 2012; 32(5):1141-4.
Lee, et al., "Clinical Course and Outcome Predictors of Critically Ill Infants With Complete DiGeorge Anomaly Following Thymus Transplantation", Pediatr Crit Care Med. Sep. 2014;15(7):e321-6.
Li , et al., 2011, "Thymic Microenvironment Reconstitution After Postnatal Human Thymus Transplantation," Clin Immunology, Apr. 16, 2011, 140(3): 244-259.
Markert, et al., "First Use of Thymus Transplantation Therapy For FOXN1 Deficiency (nude/SCID): A Report of 2 Cases." Blood. Jan. 13, 2011;117(2):688-96.
Rendell, et al., "Complete Thymectomy In Adult Rats With Non-Invasive Endotracheal Intubation," J Vis Exp 2014, (94).
Stone, Jr. et al., "A Case of Atypical, Complete DiGeorge Syndrome Without 22q11 Mutation", Ann Allergy Asthma Immunol. May 2017;118(5):640-642.
Mezrich, et al, "Role of the Thymus and Kidney Graft in the Maintenance of Tolerance to Heart Grafts in Miniature Swine", Transplantation, vol. 79, No. 12, pp. 1663-1673. Jun. 27, 2005.
Mezrich, et al, "The Role of the Thymus in the Maintenance Phase of Tolerance in Miniature Swine", The Journal of Heart and Lung Transplantation, vol. 21, No. 1, (66), pp. 78-79, Jan. 2002.
Miller, Rodney T., "Cytokeralin AE1/AE3," The Focus—Immunohislochemisry, Nov. 2003, 2 pages.
Muniappan, et al., "En-Bloc Heart And Thymus Transplantation In Cynomolgus Monkeys", Transplantation, Jul. 27, 2004, vol. 78, No. 2, 2004, p. 631.
Niimi, et al., "Importance of Thymus to Maintain Operational Tolerance to Fully Allogeneic Cardiac Grafts", Ann Thorac Surg., 2001, 72:735-739.
Ohuchi, et al., "A Novel Technique For En Bloc, Vascularized, Composite Thymic, and Cardiac Co-transplantation", Transplantation, vol. 74, 403-415, No. 3, Aug. 15, 2002.
Palmer S et al. (2018) "Thymic involution and rising disease incidence with age", Proc Natl Acad Sci US A 115:1883-1888 doi:10.1073/pnas.1714478115.
Pham SM, et al., "A Clinical Trial Combining Donor Bone Marrow Infusion and Heart Transplantation: Intermediate-term Results", J Thorac Cardiovasc Surg. Apr. 2000; 119(4 PI 1):673-81.
Pierson RN 3rd, et al., "Prolongation of Primate Cardiac Allograft Survival by Treatment with ANTI-CD40 Ligand CD154) Antibody", Transplantation. Dec. 15, 1999; 68(11):1800-5. 10 pages.
Pilat N., Sabler P, Klaus C, Mahr B, Unger L, Hock K, et al. "Blockade of adhesion molecule lymphocyte function-associated antigen-1 improves long term heart allograft survival in mixed chimeras", J Heart Lung Transplant. Sep. 2018;37(9):1119-1130.
Rajab, et al., "Heart Transplantation Following Donation After Cardiac Death: History, Current Techniques, and Future", The Journal of Thoracic and Cardiovascular Surgery, vol. 161, No. 4, pp. 1337-1340 (2021).
Sahara, H., Weiss, MJ., et al, "Thymectomy Does Not Abrogate Long-Term Acceptance of MHC Class I-Disparate Lung Allografts in Miniature Swine", Transplantation Proceedings, Dec. 2006; 38(10): 3253-3255. 6 pages.
Salvadori M., et al, "Enteric-coated mycophenolate sodium is therapeutically equivalent to mycophenolate mofetil in denovo renal transplant patients." Am J Transplant 2004;4(2):231-6.
Scalea, et al., "Abrogation of Renal Allograft Tolerance in MGH Miniature Swine: The Role of Intra-Graft and Peripheral Factors in Long-Term Tolerance", American Journal of Transplantation 2014; 14: 2001-2010.
Scalea, et al., "An Overview of the Necessary Thymic Contributions to Tolerance in Transplantation", Clinical Immunology 173 (2016) 1-9.
Schmitz R. et al., "Kidney Transplantation Using Alemtuzumab, Belatacept, and Sirolimus: Five-year Follow-up", Am J Transplant. Dec. 2020; 20(12):3609-3619.
Stehlik, J., et al., "The Registry of the International Society for Heart and Lung Transplantation: 29th official adult heartransplant report", 2012. J Heart Lung Transplant 31: 1052-1064.
Summary of FY 2001 Research Report: "An Attempt to Induce Immune Tolerance by Whole Thymus Organ Transplantation after Autologous Thymectomy/Lymphocyte Removal" (Japanese with translation), 2003, 5 pages, https://kaken.nii.ac.jp/grant/KAKENHI-PROJECT-11671153.
Sun DP et al. (2016) Thymic hyperplasia after chemotherapy in adults with mature B cell lymphoma and its influence on thymic output and CD4(+) T cells repopulation Oncoimmunology 5:e1137 417 doi:10.1080/2162402X.2015.1137417.
Tonsho, et al, "Heart En Bloc Thymus Transplantation Permits Long-Term, Acute Rejection-Free Cardiac Allograft Survival in Nonhuman Primates (NHPs)", American Transplant Congress (ATC) Meeting Abstracts, Abstract No. A251, May 2, 2015, 5 pages.
Tonsho, et al, "Heart Transplantation: Challenges Facing the Field", Cold Spring Harb Perspect Med 2014; 4:a015636, pp. 1-22.
Tonsho, et al, "Successful Tolerance Induction of Cardiac Allografts in Nonhuman Primates through Donor Kidney Co-Transplantation", American Transplant Congress (ATC) Meeting Abstracts, Abstract No. 490, 2013, 4 pages.
Von Moos, et al., "Assessment of Organ Quality in Kidney Transplantation by Molecular Analysis and Why II May Not Have Been Achieved, Yet", Frontiers in Immunology, vol. 11, Article 833, May 2020. 12 Pages.
Watanaba, et al., "Intra-bone Bone Marrow Transplantation From hCD47 Transgenic Pigs to Baboons Prolongs Chimerism to >60 Days and Promotes Increased Porcine Lung Transplant Survival", Xenotransplantation, 2020;27:e12552, 15 pages.
Weiss JM, Cufi P, Bismuth J, Eymard B, Fadel E, Berrih-Aknin S, Le Panse R (2013) SDF-1/CXCL 12 recruits B cells and antigen-presenting cells to the thymus of autoimmune myasthenia gravis patients Immunobiology 218:373-381 Doi:10.1016/j.imbio.2012.05.006.
Wickemeyer JL, Sekhsaria S (2014) "Prolonged severe immuno-deficiency following thymectomy and radiation: a case report" J Med Case Rep 8:457 doi: 10.1186/1752-1947-8-457, 6 pages.
Wood, Kathyn J., "The Induction of Tolerance to Alloantigens Using MHC Class I Molecules", Immunology, 1993,6:759-762.
Xie B., et al., :Monoclonal Antibody Treatment to Prolong the Secondary Cardiac Allograft Survival in Alloantigen-primed Mice, Scand J Immunol. May 2010; 71(5):345-52.
Yamada et al., "Tolerance in Xenotransplantation", Curr Opin Organ Transplant 22:522-528 (2017).
Yamada, et al, "Intra-bone Bone Marrow Transplantation in Pig-to-Nonhuman Primates For The Induction of Tolrance Across Xenogeneic Barriers", Methods Mol Biol. (2020), 2110: 151-171, 20 pages.
Yamada, et al, "Both Central And Peripheral Mechanisms Play A Role In Tolerance Induction And In The Prevention Of Cardiac

(56) References Cited

OTHER PUBLICATIONS

Allograft Vasculopathy (Cav) In Recipients Of Heart/Kidney Transplants", Transplantation, Jun. 27, 1998—vol. 65—Issue 12—p. S 183, 3 pages.

Yamada, et al, "Co-transplantation of Vascularized Thymic Grall with Kidney in Pig-to-Nonhuman Primates For The Induction of Tolerance Across Xenogeneic Barriers", Methods Mol Biol. 2020 ; 2110: 151-171.

Yamada, et al, "Repeated Injections of IL-2 Break Renal Allograft Tolerance Induced via Mixed Hemalopoielic Chimerism in Monkeys", American Journal of Transplantation 2015; 15: 3055-3066.

Yamada, et al, "Role of the Thymus in Transplantation Tolerance in Miniature Swine: II. Effect of Steroids and Age on the Induction of Tolerance To Class I Mismatched Renal Allografts", Transplantation, vol. 67—Issue 3, 1999, pp. 158-467.

Yamamoto, et al., "Role of the Thymus in Heletorpic Cardiac Allograft Survival in Miniature Swine: Evidence for the Need of Thymic Emigrants Immediately Post-Transplantation, and Thymic Immigrants for Long Term Tolerance Induction", The Journal of Heart and Lung Transplantation, 273, Jan. 2003, 1 page.

Zaitseva M, Kawamura T, Loomis R, Goldstein H, Blauvelt A, Golding H (2002) Stromal-derived factor 1 expression in the human thymus J Immunol 168:2609-2617 doi:10.4049/jimmunol.168.6.2609.

Zhao, et al., "A Model of Isolated, Vascular Whole Thymus Transplantation in Nude Rats", Transplantation Proceedings, 44, 1394-1398 (2012).

Zhao, et al., "Vascularized Whole Thymus Transplantation in Rowett Nude Rats: Effect of Thymus Allograft Volume on Tolerance Induction", Transplant Immunology 23 (2010) 40-44.

Markert, et al, "Successful formation of a chimeric human thymus allograft following transplantation of cultured postnatal human thymus", The Journal of Immunology, Jan. 15, 1997 (Jan. 15, 1997), p. 998, XP05573897 4, United States Retrieved from the Internet: URL:https://www.jimmunol.org/content/158/2/998.full.pdf.

Rice, H E, et al, "Thymic transplantation for complete DiGeorge syndrome: Medical and surgical considerations", Journal of Pediatric Surgery, W. B. Saunders Company, US, vol. 39, No. 11, Nov. 1, 2004 (Nov. 1, 2004), pp. 1607-1615, XP004707879, ISSN: 0022-3468, DOI: 10.1016/J.JPEDSURG.2004.07.020.

Kwun,Jean et al, "Cultured thymus tissue implementation promotes donor-specific tolerance to allogeneic heart transplants", JCI Insight, Apr. 30, 2020 (Apr. 30, 2020), XP055738728, DOI: 10.1172/jci.insight.129983.

Sharabi Y, et al., "Mixed Chimerism and Permanent Specific Transplantation Tolerance Induced By a Nonlethal Preparative Regimen," J Exp Med (1989), 169(2):493-502.

Manilay, et al., 1998, "Intrathymic Deletion of Alloreactive T Cells in Mixed Bone Marrow Chimeras Prepared With a Nonmyeloablative Conditioning Regimen," Transplantation 66(1):96-102.

Yamada K, et al., 1997, "Role of the Thymus in Transplantation Tolerance in Miniature Swine: I. Requirement of the Thymus For Rapid and Stable Induction of Tolerance to Class I-Mismatched Renal Allografts," J Exp Med 186(4):497-506.

Yamada K, et al., 2003, "Thymic Transplantation in Miniature Swine: III. Induction of Tolerance by Transplantation of Composite Thymokidneys Across Fully Major Histocompatibility Complex-Mismatched Barriers," Transplantation 76(3):530-536.

Nobori S, et al., 2006, "Thymic Rejuvenation and the Induction of Tolerance by Adult Thymic Grafts," Proc Natl Acad Sci U S A 103(50):19081-19086.

Davies et al., "Thymus Transplantation for Complete DiGeorge Syndrome: European Experience", J Allergy Clin Immunol. Dec. 2017;140(6):1660-1670.

Collard HR, et al., Possible Extrathymic Development of Nonfunctional T Cells in a Patient With Complete DiGeorge Syndrome. Clin Immunol. May 1999;91(2):156-62.

Markert, et al., "Postnatal Thymus Transplantation With Immunosuppression As Treatment For DiGeorge Syndrome," Blood Oct. 15, 2004; 104(8):2574-2581.

Markert, et al., "Transplantation of Thymus Tissue in Complete DiGeorge Syndrome," N Engl J Med. Oct. 14, 1999; 341(16):1180-1189.

Markert, et al., "The human Thymic Microenvironment During Organ Culture." Clin Immunol Immunopathol. Jan. 1997;82(1):26-36.

Markert, et al., "Factors Affecting Success of Thymus Transplantation For Complete DiGeorge Anomaly", Am J Transplant. Aug. 2008;8(8):1729-36.

Markert, et al., "Successful Formation of a Chimeric Human Thymus Allograft Following Transplantation of Cultured Postnatal Human Thymus." J Immunol. Jan. 15, 1997;158(2):998-1005.

Markert, M. Louise, 2014, "Thymus Transplantation." Sullivan KE & Stiehm ER (Eds) (Academic Press), Chapter 60, pp. 1059-1067.

Markert, et al. "Effect of Highly Active Antiretroviral Therapy and Thymic Transplantation on Immunoreconstitution in HIV Infection", AIDS Res Hum Retroviruses. Mar. 20, 2000;16(5):403-13.

Markert, et al., "Thymus Transplantation," Clin Immunology, May 2010, 135(2): 236-246.

Markert ML, "Perspective: Research Highlights at the Duke University Center For AIDS Research. Immunoreconstitution in HIV Infection: The Role of the Thymus", AIDS Res Hum Retroviruses. Jun. 10, 1996;12(9):751-5.

Markert, et al. "Complete DiGeorge Syndrome: Persistence of Profound Immunodeficiency", J Pediatr. Jan. 1998;132(1):15-21.

Markert, et al., "Thymopoiesis in HIV-Infected Adults After Highly Active Antiretroviral Therapy", AIDS Res Hum Retroviruses. Nov. 20, 2001;17(17):1635-43.

Yin, et al., "Disseminated Mycobacterium Kansasii Disease In Complete DiGeorge Syndrome", J Clin Immunol. Jul. 2015;35(5):435-8.

Selim, et al., "The Cutaneous Manifestations of Atypical Complete DiGeorge Syndrome: A Histopathologic and Immunohistochemical Study." J Cutan Pathol. Apr. 2008;35(4):380-5.

Boehm, et al., 2014, "Thymic Development and Selection of T Lymphocytes." Heidelberg: Springer-Verlag. vol. 373, pp. 1-132.

Isakovic, et al., 1965, "Immunologic Tolerance in Thymectomized, Irradiated Rats Grafted with Thymus from Tolerant Donors," Science 148(3675):1333-1335.

Neufeld, M. et al., 1981, "Two Types of Autoimmune Addison's Disease Associated With Different Polyglandular Autoimmune (PGA) Syndromes," Medicine 60: 355-362.

Hong, et al., 1979, "Transplantation of Cultured Thymic Fragments. II. Results in Nude Mice," J Exp Med., 149(2):398-415.

Li, et al., 2009, "Characterization of Cultured Thymus Tissue Used For Transplantation With Emphasis On Promiscuous Expression Of Thyroid Tissue-specific Genes," Immunol Res. 2009; 44 (1-3):71-83.

Haynes, et al., The Role Of The Thymus In Immune Reconstitution In Aging, Bone Marrow Transplantation, and HIV-1 Infection. Annu Rev Immunol. 2000;18:529-60.

Rice, et al., "Thymic Transplantation For Complete DiGeorge Syndrome: Medical and Surgical Considerations", J Pediatr Surg. Nov. 2004; 39(11):1607-15.

Parker, W. et al., "Specificity and Function of 'Natural' Antibodies In Immunodeficient Subjects: Clues to B Cell Lineage and Development," 1997, J Clin Immunol., 17:311-321.

Heron, I., "A Technique For Accessory Cervical Heart Transplantation In Rabbits and Tats," 1971 Acta Pathol Microbiol Scand A 79(4):366-372).

Ahonen, P., 1985, "Autoimmune Polyendocrinopathy—Candidosis—Ectodermal Dystrophy (APECED): Autosomal Recessive Inheritance," Clinical Genetics, 27: 535-542.

Ahonen, P., et al., 1987, "Adrenal and Steroidal Cell Antibodies In Patients With Autoimmune Polyglandular Disease Type I and Risk Of Adrenocortical and Ovarian Failure," J. Clin. Endocrinology and Metabolism, 64: 494-500.

Ahonen, P., et al., 1988, "The Expression of Autoimmune Polyglandular Disease Type I Appears Associated With Several HLA-A Antigens But Not With HLA-DR", J. Clin. Endocrinology and Metabolism, 66, 1152-1157.

(56) References Cited

OTHER PUBLICATIONS

Ahonen, P., et al., 1990, "Clinical Variation Of Autoimmune Polyendocrinopathy-Candidiasis-Ectodermal Dystrophy (APECED) In A Series of 68 Patients," New Engl. J. Med. 322: 1829-1836.

Arulanantham, K., et al., 1979, "Evidence for Defective Immunoregulation in the Syndrome of Familial Candidiasis Endocrinopathy," New Eng. J. Med. 300:164-168.

Blizzard, R. M. et al., 1963, "Studies of the Adrenal Antigens and Antibodies in Addison's Disease," J. Clin. Invest. 42: 1653-1660.

Krohn, K., et al., 1992, "Identification By Molecular Cloning Of An Autoantigen Associated With Addison's Disease As Steroid 17α-hydroxylase," Lancet 339:770-773.

Perheentupa J., 2002, "APS-I/APECED: the Clinical Disease and Therapy," Endocrinol. Metab. Clin. North Am. 31:295-320.

Davis, CM, et al., "Normalization Of The Peripheral Blood T Cell Receptor V Beta Repertoire After Cultured Postnatal Human Thymic Transplantation in DiGeorge Syndrome." J Clin Immunol. Mar. 1997;17(2):167-75.

Schoenecker, et al., 2000, "Exposure To Topical Bovine Thrombin During Surgery Elicits A Response Against The Xenogeneic Carbohydrate Galactose α1-3Galactose," J Clin Immunol., 20:434-444.

Uibo R., et al., 1994, "Autoantibodies To Cytochrome P450 Enzymes P450scc, P450c17, and P450c21 In Autoimmune Polyglandular Disease Types I and II and In Isolated Addison's Sisease," J. Clin. Endocrinol. Metab. 78: 323-328.

Zlotogora, J., et al., 1992, "Polyglandular Autoimmune Syndrome Type I Among Iranian Jews," J. Med. Genet, 29, 824-826.

Schmid, et al., 1994,"Successful Heterotopic Heart Transplantation In Rat," Microsurgery 15(4):279-281.

Curcio, et al., "Robotic-Assisted Thoracoscopic Surgery Thymectomy," Journal of Visualized Surgery, Nov. 7, 2017 (Nov. 7, 2017), vol. 3, Iss. 162, pp. 1-4.

DeWolf, et al., "A New Window into the Human Alloresponse," Transplantation, Aug. 31, 2016 (Aug. 31, 2016), vol. 100, Iss. 9, pp. 1639-1649.

Furudate, et al., "Sequential Therapy with Nivolumab Followed by Ipilimumab Induces Complete Response in Metastatic Melanoma of the Lung but with Severe Hepatotoxicities," Case Reports in Oncology, Oct. 17, 2016 (Oct. 17, 2016), vol. 9, No. 3, pp. 644-649.

Zachary, et al., "HLA Mismatching Strategies for Solid Organ Transplantation—A Balancing Act," Frontiers in Immunology, Dec. 7, 2016 (Dec. 7, 2016), vol. 7, No. 575, pp. 1-14.

Gebel, et al., "HLA Antibody Detection With Solid Phase Assays: Great Expectations or Expectations Too Great?," American Journal of Transplantation, Aug. 1, 2014 (Aug. 1, 2014 ), vol. 14, No. 9, pp. 1964-1975.

Shichkin, et al., "Effect of Cryopreservation On Viability and Growth Efficiency of Stromal-epithelial Cells Derived From Neonatal Human Thymus," Cryobiology, Jun. 28, 2017 (Jun. 28, 2017), vol. 78, pp. 70-79.

CFR Title 21; 1271, "Human Cells, Tissues, and Cellular and Tissue-Based Products; Establishment Registration and Listing." Agency: Food and Drug Adminstration, HHS. Fed. Reg. vol. 69, No. 17, Jan. 27, 2004, pp. 3823-3826.

Li, B. et al., "Thymic Microenvironment Reconstitution After Postnatal Human Thymus Transplantation.". Clin Immunol, Apr. 16, 2011, vol. 140, No. 3, Author's manuscript from PubMed: pp. 1-27p. 2 last para., p. 3 third para., p. 5 first-second para., p. 6 third para., Citation is not enclosed due to copyright restrictions.

Markert M. L. et al., "Factors Affecting Success of Thymus Transplantation for Complete DiGeorge Anomaly," Am J Transplant, Jun. 28, 2008, vol. 8, No. 8, pp. 1729-1736.

Khubutia, M. Sh., et al., "Immunological Tolerance in Organ Transplantation," Transplantology, 2017; 9(3):211-225. DOI:10.23873/2074-0506-2017-9-3-211-225. 37 pages with translation.

Curico, Carlo et al., "Robotic-assisted Thoracoscopic Surgery Thymectomy," Journal of Visualized Sugery, (Nov. 7, 2017), vol. 3, No. 162, doi: 10.21037/jovs.2017.10.01, pp. 1-4.

Onischenko NA et al., "Donor Bone Marow Cells As Regulators of Immune Tolerance Induction in the Recipient's Body During Allogeneic Organ Transplantation," Bulletin of Transplantology and Artificial Organs. T.XI. N Apr. 2009, pp. 97-102, (15 pages with translation). file:///C:/Users/i_a_b/Desktop/276-590-1-SM.pdf.

Zachary A. A. et al, "HLA Mismatching Strategies for Solid Organ Transplantation—A Balancing Act," Front Immunol, Dec. 7, 2016, vol. 7, Article 575: pp. 1-14.

A

B

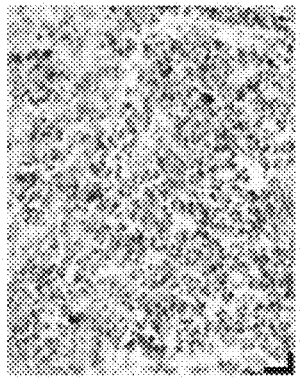
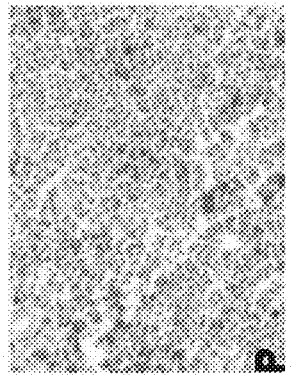
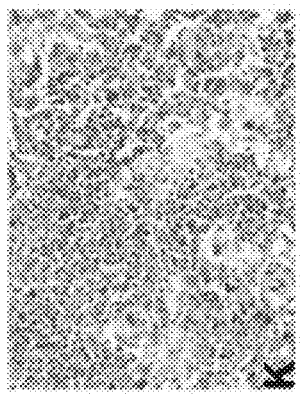
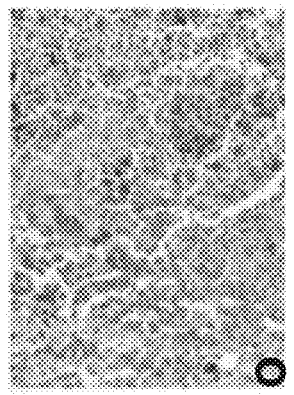
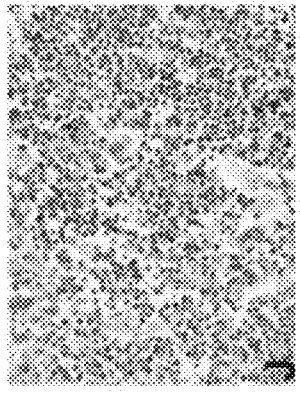
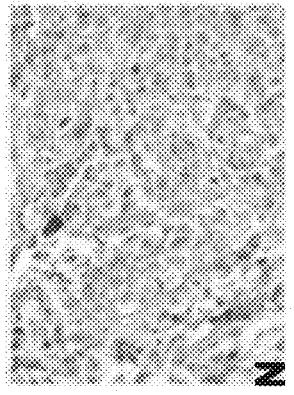
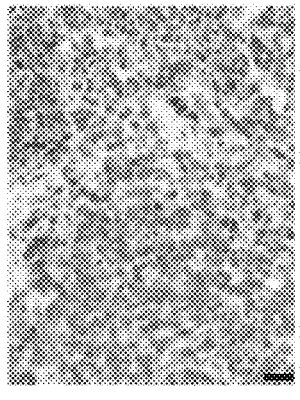
FIG. 33I, FIG. 33J, FIG. 33K, FIG. 33L, FIG. 33M, FIG. 33N, FIG. 33O, FIG. 33P

CULTURED THYMUS TISSUE TRANSPLANTATION PROMOTES DONOR-SPECIFIC TOLERANCE TO ALLOGENEIC SOLID ORGAN TRANSPLANTS

CROSS REFERENCE TO RELATED APPLICATION

This application is a divisional of U.S. application Ser. No. 16/283,007, filed Feb. 22, 2019 which claims the benefit to and priority of U.S. Provisional Application No. 62/634,377, filed Feb. 23, 2018, and is a continuation application of PCT/US19/19137 filed Feb. 22, 2019, the subject matter of which is incorporated herein in its entirety by reference.

BACKGROUND

Field of Invention

Methods and compositions for promoting donor-specific tolerance to allogeneic solid organ transplants in a recipient receiving an allogeneic solid organ transplant from a donor.

Background of the Invention

Organ transplantation requires the preparation and harvesting of a human solid organ from a donor and transplantation into the recipient. The major problem in solid organ transplantation is that the recipient is not tolerant of the donor. The recipient T cells will reject the organ and the recipient B cells will develop antibodies to the organ causing its eventual failure. The holy grail of solid organ transplantation is development of tolerance to the transplanted human organ by the recipient. More than 36,000 organ transplants are estimated to be performed per year in the U.S., and many more in in Europe, and other major countries. It is further estimated that there are more than 120,000 patients on waiting lists in the U.S. for organ transplants. Demand for healthy organs significantly exceeds the supply of suitable organs. In 2018, approximately 10,000 donors were identified. See https://optn.transplant.hrsa.gov.

Transplant rejection is a substantial challenge in solid organ transplantation. Transplant rejection by both T cells and B cells can lead to significant complications in organ function or even to transplant failure. The 5-year graft survival, for example, for heart transplants is 77.7%, for kidney transplants is 78.6%, for liver transplants is 72.8%, and for lung transplants is 53.4%. Typically, this problem has been addressed, in part, through the matching of donors and recipients for major histocompatibility complex (MHC) antigens and by avoiding recipients with antibodies to the recipient tissue types. In addition, the use of immunosuppressive regimens to manage the immunological response underlying transplant rejection has improved. However, tolerance has not been achieved and the mean survival for many organs is only 10 years.

Preservation of organ viability prior to and during the implantation procedure is a second significant challenge. The removal, storage and transplantation of an organ may profoundly affect the internal structure and function of the organ and can influence significantly the degree to which the return of normal organ function is delayed or prevented after transplantation is completed.

The time period in which solid human organs may be effectively preserved varies by organ, with kidneys ranging from 24-36 hours, pancreas from 12-18 hours, liver from 8-12 hour and heart and lung from 4-6 hours. See https://unos.org/transplantation/matching-organs.

Organ injury occurs primarily as a result of ischemia and hypothermia, but may also be related to reperfusion of the organ ex vivo or during implantation.

Techniques for organ preservation, including ex vivo perfusion, are known in the art and serve to minimize organ damage and promote optimal graft survival and function.

The principal solid organs which have been the subject of transplantation procedures, include kidney, liver, heart, and lungs. Success in transplanting these solid organs has been achieved with varying degrees of success. The principal variability resides in the techniques that are used to interfere with immune-mediated graft rejection. Experience has shown that there is no one single immunosuppressive agent or technique that is useful in all settings involving solid organ transplantation. The limiting factor usually resides in the toxicity associated with each individual immunosuppressive agent. The toxicity associated with a given immunosuppressive agent may frequently hinder the normal functioning of the transplanted solid organ or of other organs such as the kidneys which can fail when calcineurin inhibitors are used to prevent rejection.

The toxicity drawbacks associated with known immunosuppressive agents normally used to prevent graft rejection in solid organ transplants presents a need to find new methods for preventing graft rejection of solid organ transplants.

The ability to discriminate between self and non-self antigens is central to the immune response. This discrimination results in self-tolerance. Autoimmunity develops when there has been a loss of self-tolerance. An unmet need exists in transplantation procedures to induce tolerance to solid organ transplants.

SUMMARY OF THE INVENTION

Achieving donor-specific immune tolerance remains the ultimate immunologic goal in transplantation. Most of the current approaches focus on controlling peripheral mature donor-reactive T cells by depletion (e.g. alemtuzumab, Thymoglobulin® (anti-thymocyte globulin), etc.) or suppression (e.g. calcineurin inhibitors, basiliximab, etc.) without targeting the production of alloreactive T cells in thymus. However, even with the dramatic advancement of immunosuppressive drugs and new immunomodulatory regimens, transplant tolerance has not yet been consistently achieved.

The present inventor has shown that tolerance to solid organ transplants may be achieved through the implantation of allogeneic cultured postnatal thymus tissue-derived product (referred to herein also as "CTT" or as "RVT-802"), in a thymectomized recipient, to shorten the time period of use of post-transplantation immunosuppressive agents to prevent rejection of the transplanted organ. The removal of the recipient's thymus and substitution of an allogeneic cultured postnatal thymus tissue-derived product results in reconstitution of the solid organ recipient's immune system and tolerance to the recipient's self as well as to the transplanted allogeneic solid organ.

Tolerance induction by surgical insertion of allogeneic cultured postnatal thymus tissue-derived product is similar to tolerance induction via donor dendritic cells ("DC") in hematopoietic stem cell transplantation (Sharabi Y & Sachs D H, 1989, "Mixed chimerism and permanent specific transplantation tolerance induced by a nonlethal preparative regimen," *J Exp Med* 169(2):493-502; Manilay J O, Pearson D A, Sergio J J, Swenson K G, & Sykes M, 1998, "Intrathymic deletion of alloreactive T cells in mixed bone marrow chimeras prepared with a nonmyeloablative conditioning regimen," Transplantation 66(1):96-102.). A series of studies from Transplantation Biology Research Center (TBRC, Boston, MA) showed the crucial role of thymus in tolerance induction (Yamada K, et al., 1997, "Role of the thymus in transplantation tolerance in miniature swine. I. Requirement of the thymus for rapid and stable induction of tolerance to class I-mismatched renal allografts," *J Exp Med* 186(4):497-506.) and tested thymus transplantation with tolerance induction in a large animal model (Yamada K, et al., 2000, "Thymic transplantation in miniature swine. II. Induction of tolerance by transplantation of composite thymokidneys to thymectomized recipients," *J Immunol* 164(6):3079-3086; 5; Yamada K, et al., 2003, "Thymic transplantation in miniature swine: III. Induction of tolerance by transplantation of composite thymokidneys across fully major histocompatibility complex-mismatched barriers," Transplantation 76(3):530-536; Nobori S, et al., 2006, "Thymic rejuvenation and the induction of tolerance by adult thymic grafts," *Proc Natl Acad Sci USA* 103(50): 19081-19086. In their series of studies, this group successfully used Class II matched/Class I mismatched donor (thymus and kidney or heart) as thymus composite tissues (thymokidney and thymoheart) with 12 days of cyclosporine ("CsA") for transplant tolerance induction. They claimed that non-vascularized thymus did not induce tolerance in their model. More precisely, however, non-vascularized thymus that was not cultured did not engraft long-term. As they indicated, the failure of engraftment of the uncultured thymus may have been due to ischemic injury in addition to alloimmunity (Yamada K, et al., 2000). This elegant concept of generating vascularized thymus prior to transplantation to induce tolerance, would be difficult to translate to the clinic without using xenotransplantation. (This section cites Kwan J et al Cultured Thymus Transplantation Promotes Donor-specific Tolerance to Allogeneic Heart Transplants, to be submitted for publication 2019.)

The limitation of non-vascularized thymus transplantation can be overcome with a culture system as well as T cell depletion. Experimental transplantation of allogeneic cultured postnatal thymus tissue-derived product (CTT) that retains TECs has been successfully applied to treat pediatric patients with congenital athymia (Markert M L, Devlin B H, McCarthy E A, 2010, "Thymus transplantation," *Clin Immunol.,* 135(2): 236-46; Markert M L, et al., 2004, "Postnatal thymus transplantation with immunosuppression as treatment for DiGeorge syndrome," *Blood* 104(8):2574-2581; Markert M L, et al., 1999, "Transplantation of thymus tissue in complete DiGeorge syndrome," *N Engl J Med* 341(16): 1180-1189 27).

In this reference, DiGeorge Syndrome is defined as a condition in which there are variable defects in the heart, thymus and parathyroid gland. Approximately 1% of infants with DiGeorge syndrome have athymia and hence no T cells to fight infection. These infants are said to have complete DiGeorge syndrome. There are 4 subgroups of children who meet the criteria of complete DiGeorge syndrome, 22q11.2 deletion syndrome, CHARGE, infants of diabetic mothers, and infants with no syndromic or genetic defects. In all four groups, the infants with athymia represent a very tiny group, possibly 1% of the total children carrying the diagnosis, such as the diagnosis of 22q11.2 deletion syndrome.

Thymopoiesis has been documented by allograft biopsies and the presence of recipient naive T cells in the periphery (Markert M L, 2010; Markert M L, et al., 2008, "Use of allograft biopsies to assess thymopoiesis after thymus transplantation," *J Immunol* 180(9):6354-6364; Markert M L, et al., 2007, "Review of 54 patients with complete DiGeorge anomaly enrolled in protocols for thymus transplantation: outcome of 44 consecutive transplants," *Blood* 109(10): 4539-454728). Studies of children treated with investigational CTT show tolerance to donor MHC by mixed lymphocyte reactions (Chinn I K, Devlin B H, Li Y J, & Markert M L, 2008, "Long-term tolerance to allogeneic thymus transplants in complete DiGeorge anomaly," *Clin Immunol* 126(3):277-281). In addition, the infants with congenital athymia, after CTT transplantation, are able to control infections such as Epstein Barr virus (Markert M L, 2014, Thymus Transplantation. *Stiehm's Immune Deficiencies*, eds Sullivan K E & Stiehm E R (Academic Press), 1st Ed, pp 1059-1067; Isakovic K, Smith S B, & Waksman B H, 1965, "Immunologic Tolerance in Thymectomized, Irradiated Rats Grafted with Thymus from Tolerant Donors," *Science* 148 (3675):1333-1335). Based on these data in humans with congenital athymia, it was determined that allogeneic cultured postnatal thymus tissue-derived product expressing the MHC of a solid organ donor after surgical insertion in the recipient will develop tolerance to both self and to the donor, while producing functional T cells that will protect the recipient from infection. *Thymus Gland and Education of Thymocytes.* (This section cites Kwan J et al Cultured Thymus Transplantation Promotes Donor-specific Tolerance to Allogeneic Heart Transplants, to be submitted for publication 2019).

The thymus gland normally is located on top of the heart. The thymus provides an essential microenvironment for T cell development and is critical to the establishment and maintenance of the adaptive immune system (Boehm T and Takahama Y, 2014, *Thymic Development and Selection of T Lymphocytes.* Heidelberg: Springer-Verlag). During postnatal development, the thymus educates hematopoietic stem cells migrating from the bone marrow to the thymus gland. The progenitor stem cells colonize the thymus thereby forming thymocytes. The thymocytes thereafter undergo a series of maturation steps. This is evidenced by the expression of a number of observable cell surface markers appearing on the thymocytes.

T cells are critical for the protection of the body from infections. T cells that develop in a normally functioning thymus develop a diverse set of T cell receptors (generally proteins on the surface of the cell), which enable the mature T cell to fight a wide variety of infections. During this education process the developing T cells are instructed by the thymus not to attack the body's normal proteins, such as insulin or parathyroid hormone (which regulate glucose and calcium levels in the blood). These instructions are carried out under the influence of the autoimmune regulator gene ("AIRE gene").

Briefly, the education process occurs in the normally functioning thymus gland. Thymocytes in the thymus gland, formed from bone marrow stem cells, are taught by thymus epithelial cells ("TECs") and dendritic cells ("DCs") located within the thymus to not attack recipient major histocompatibility complex (MHC) proteins (antigens) such as HLA-A, HLA-B, HLA-C, HLA-DRB1, HLA-DQB1, HLA-DQA1, HLA-DPB1, HLA-DPA1 antigens. The HLA antigens have 2 proteins that hold a self-peptide in a groove. The self-peptide could be from a thyroid protein or an insulin peptide or almost any other protein expressed in the body. Thymocytes developing in the thymus form a T cell receptor (TCR) composed of two proteins that cross the membrane. The TCR is expressed on the cell surface of the T cells. Each T cell expresses many copies of its unique TCR. If the TCR binds too tightly to the self peptide:MHC on a dendritic cell, the dendritic cells provides a signal to make the T cell undergo apoptosis and die. This mechanism prevents the development of autoimmunity to self. The TEC can also provide a signal to thymocytes that they are binding too tightly. Lastly the DC can grab bits of membrane from the TEC and present the TEC self peptide:MHC to the developing thymocyte. If the thymocytes bind too tightly, the DC sends a signal so that the thymocyte undergoes apoptosis and dies. By these mechanisms, T cells that leave the thymus are not self-reactive. The T cells that leave the thymus are very variable and can recognize infections but they do not attack proteins of the body.

The two major constituents of thymus are epithelium and thymocytes that are produced in the thymus in the following manner. Cells derived from bone marrow stem cells, common lymphoid progenitors ("CLPs"), migrate to the thymus. The CLPs enter the thymus in response to signals (chemokines) produced by the thymus epithelium and endothelium. In the thymus the CLPs differentiate into thymocytes and proliferate. Thymocytes develop a unique T-cell receptor ("TCR") that is expressed on the cell surface. Thymocytes also begin to express the T cell molecules CD3, CD4 and CD8. A vast diversity of T cells develop rendering the cells capable of responding to infections throughout the life of the recipient. Mixed lymphocyte reactions show tolerance of the recipient T cells in children who are treated with cultured thymus tissue (RVT-802) to thymus donor MHC.

Self-reactive recipient thymocytes are deleted prior to exit from the thymus. This occurs by interaction of recipient thymocytes and recipient DCs that migrate to the thymus. Apoptosis is induced in recipient thymocytes that bind too tightly to the DCs as a measure to protect the body from autoimmune disease. After completion of this process, the thymocytes exit the thymus. The new circulating T cells, i.e., "naïve" T cells, express the markers CD45RA and CD62L. Flow cytometry and spectra typing have shown development of a diverse T cell repertoire. These recipient T cells have diverse TCR repertoires and proliferate normally in response to mitogens. They protect the recipient from infection without having autoreactivity to self.

Allogeneic Cultured Postnatal Thymus Tissue-Derived Product.

Allogeneic cultured postnatal thymus tissue-derived product has been shown to be useful for the treatment of T cell immunodeficiency (primary immune deficiency) resulting from congenital athymia. T cell immunodeficiency due to athymia is associated with congenital disorders which prevent the development of a functional thymus, such as complete DiGeorge Anomaly (cDGA) associated with 22q11.2 deletion and CHARGE (coloboma, heart defect, choanal atresia, growth or mental retardation, genital hypoplasia and ear anomalies or deafness) syndrome associated with mutations in the chd7 (chromodomain-helicase-DNA-binding protein 7) gene and in athymic patients with forkhead box protein N1 (FOXN1) deficiency. Congenital athymia is a rare fatal condition and currently has no drug treatment options utilizing regulatory approved drug products. If left untreated and no therapeutic reconstitution of the child's immune system occurs, the primary immunodeficiency due to congenital athymia is fatal, with almost all infants dying before the age of two years, most often by severe infections.

Allogeneic cultured postnatal thymus tissue-derived product is a tissue-engineered product. Based on disclosures in this specification and Examples, CTT is expected to be useful for the development of tolerance in a recipient receiving a transplanted solid organ.

As described more fully in this specification and Examples, the surgical administration of allogeneic, cultured postnatal thymus tissue-derived product (e.g., "RVT-802") in athymic patients leads to a cascade of events resulting in the development of a functional immune system.

Following surgical placement of allogeneic, cultured postnatal thymus tissue-derived product (e.g., RVT-802) in the recipient, T cells are educated by donor TECs and recipient DCs. Donor TECs in conjunction with recipient DCs enable tolerance to the implanted donor thymus tissue, which is implanted as cultured thymus tissue slices. This is the same tolerance induction as in a normal thymus. The recipient TECs in conjunction with recipient DCs lead to tolerance to self as described in this specification.

This complex process has been shown clinically to lead to >70% survival in patients with congenital athymia receiving allogeneic, cultured postnatal thymus tissue derived product (e.g., RVT-802) due to the recipient's capacity to fight infections (Markert M L, Devlin B H, Alexieff M J, Li J, McCarthy E A, Gupton S E, et al., 2007, "Review of 54 patients with complete DiGeorge anomaly enrolled in protocols for thymus transplantation: outcome of 44 consecutive transplants," *Blood*, 109(10): 4539-47; Markert M L, Devlin B H, McCarthy E A. Thymus transplantation. 2010, *Clin. Immunol.*, 135(2): 236-46). The recipients are able to control viral infections such as Epstein-Barr virus that would have been fatal prior to CTT. (Chinn I K, Devlin B H, Li Y J, & Markert M L, 2008).

Overview of Tolerance Induction in Solid Organ Transplant in Combination with Transplantation of CTT In accordance with the description, figures, examples and claims of the present specification, the inventor has demonstrated that CTT induces donor-specific tolerance in a rat heart transplantation model. The experiments reported herein used comparable CTT transplantation methods that have been used clinically in subjects with congenital athymia, such as subjects afflicted by cDGA. cDGA infants have essentially no naïve T cells prior to surgical placement of CTT. Following surgical placement of CTT, the infants developed naïve T cells approximately 6 months after the surgical procedure. (Markert M L, et al., 2004, "Postnatal thymus transplantation with immunosuppression as treatment for DiGeorge syndrome," *Blood* 104(8):2574-2581; Markert M L, Devlin B H, & McCarthy E A, 2010, "Thymus transplantation," *Clin Immunol* 135(2):236-246). The studies of tolerance induction in a rat model were based on the results of investigations of transplantation of allogeneic postnatal cultured thymus tissue-derived product (CTT) from 1993 to 2017 in athymic infants with complete DiGeorge anomaly. Favorable results were obtained in the reported studies of surgical placement of CTT in infants having congenital athymia. The published results showed an overall survival rate of 71% (61/86) (median 11.7 years, range 1.2 to 25 years) in this otherwise fatal condition (Markert, M L, et al., 2010). Biopsies of the transplanted cultured thymus tissue have demonstrated thymopoiesis on immunohistochemistry (Markert, M L, et al., 2008). Flow cytometry and spectratyping have shown development of a diverse T cell repertoire. Mixed lymphocyte reactions show tolerance of the recipient T cells to thymus donor antigen presenting cells (Chinn I K, Devlin B H, Li Y J, & Markert M L, 2008).

Importantly, the recipients of CTT are able to control viral infections such as Epstein-Barr virus that would have been fatal prior to CTT (Markert, M L, 2014, *Thymus Transplan-* tation. *Stiehm's Immune Deficiencies*, eds Sullivan K E & Stiehm E R (Academic Press), 1st Ed, pp 1059-1067). Based on these human data showing tolerance to unmatched thymus MHC antigens, transplantation of CTT in a rat model was evaluated using the same methods used clinically, for its ability to induce donor-specific tolerance in a rat heart transplantation model. These studies showed that transplanting unmatched hearts along with donor CTT expressing the heart donor's MHC class I and class II antigens (with initial T cell depletion by anti CD5 and immunosuppression with cyclosporine) induces tolerance to the antigens of the donor heart while preserving alloreactivity toward other MHC antigens.

The present invention substantiates donor thymus co-transplantation with solid organs as a method of tolerance induction with regard to the transplanted solid organ in the recipient. The patient group that would most benefit from the procedure is infants needing heart transplants. Since postnatal thymic tissue is present and could be removed from deceased infants, and the recipient thymus is routinely removed from infants undergoing heart transplantation, no additional procedure aside from cultured thymus tissue transplantation (CTT) would be needed to transfer this approach to the clinic.

Overview of Preparation of Alogeneic, Cultured Postnatal Thymus-Tissue Derived Product Allogeneic, cultured postnatal thymus-tissue derived product is prepared, cultured and stored for up to 21 days, and, on the day of implantation, placed in individual sterile cups for transport to the operating room, as described in more detail herein.

The CTT (cultured thymus tissue) is aseptically processed and cultured under current Good Manufacturing Practices ("cGMP"), for example, cGMPs established by the U.S. Food & Drug Administration ("FDA"), to produce partially T cell-depleted thymus tissue slices. CTT is differentiated from native thymus by a conditioning process described in detail below. CTT effects the normal positive and negative selection process of developing T cells in the thymus after implantation, enabling the T cells to be tolerant to both the donor thymus and the donor solid organ transplant plus recipient tissues. In addition, these T cells can recognize foreign antigens in the context of recipient major histocompatibility (MIC) proteins so as to fight infection.

The route of administration is by surgical implantation of CTT, in the manner described below. A single administration is typically 1,000 to 20,000 mm$^2$ of CTT surface area per recipient body surface area ("BSA") in m$^2$. The surface area is the total of all the surface areas of all cultured tissue slices. The individual CTT slices are implanted in a single administration surgical procedure.

Surgical implantation of allogeneic cultured postnatal thymus tissue-derived product in athymic patients leads to a cascade of events resulting in the development of a functional immune system. (Markert M L, 2007; Markert M L, et al., 2010; Markert M L, Devlin B H, McCarthy E A. Chapter 84 *Thymic reconstitution*. 2013. In: Fleisher T A, Shearer W T, Schroeder H W, Frew A J, Weyand C M, editors. Clinical Immunology (Fourth Edition). London; pp. 1032-8).

Recipient CLPs of the bone marrow migrate to the donor thymus graft. The donor thymus graft provides a microenvironment in which the recipient thymocytes develop a broad repertoire of TCRs capable of recognizing pathogens.

Migration of recipient DCs to the donor thymus depletes self-reactive recipient thymocytes that would attack the recipient's tissues after the new T cells leave the thymus and enter the circulation. Genetically-recipient naïve T cells emerge in the circulation approximately 5-12 months after administration. These recipient T cells have diverse TCR repertoires and proliferate normally in response to mitogens. They protect the recipient from infection without having autoreactivity to self.

Recipient bone marrow CLPs migrate to the thymus allograft where they develop into recipient T cells. Negative selection by recipient DCs that have migrated to the donor thymus results in tolerance to the recipient MHC antigens. Immunmohistochemical evidence of thymopoiesis is observed in biopsies of the transplanted cultured thymus tissue taken within approximately 2-3 months of transplantation. The thymopoiesis reflects the ability of the T cells to defend against and control infection, and prevent autoimmune disease.

Naïve T cells are detected in the circulation 5-12 months post-transplantation, resulting in the ability to defend against and control infection, and the prevention of autoimmune disease.

Implantation of cultured thymus tissue was first shown by the inventor to be beneficial in treating primary immune deficiency resulting from congenital athymia associated with conditions such as complete DiGeorge anomaly (cDGA) or forkhead box protein N1 (FOXN1) deficiency. The inventor herein discovered that replacement of defective thymus tissue with normal thymus tissue after culture (e.g. CTT and RVT-802) may also obviate the lack of tolerance observed in recipients of transplanted solid organs.

The non-clinical and clinical work underlying the treatment of congenital athymia through placement of cultured thymus tissue led to the realization that placement of CTT (e.g., RVT-802) in patients may permit the development of tolerance to a transplanted solid organ. Specifically, placement of CTT will reconstitute an immune system and induce tolerance to the donor organ if the subject is first thymectomized and immunosuppressed prior to the implantation of the CTT that expresses the MHC of the donor organ.

Measurement of the expression and distribution of certain markers associated with the cellular components of the thymus establish a phenotype following ex vivo. The culturing conditions described in this specification and Examples support the observation of in vivo thymopoiesis following placement of CTT in an athymic subject.

Importantly, after the surgical placement of CTT in an athymic recipient, the development of naïve T cells and the presence of a broad range of TCR-variable regions provides clear evidence that culturing of thymus tissue can foster the development of a functional endogenous T cell population. In addition, the expression of key regulatory and structural genes was noted in thymus tissue during culturing. Circulating naïve (CD45RA+CD62L+) T cells can be first detected 3-5 months after surgical insertion of CTT. These observations have been noted in the treatment of patients with complete DiGeorge Anomaly (Markert M L, 2010; Markert M L. 2013).

The nonclinical data described in the literature for thymus tissue implantation aligns with the robust clinical efficacy of transplanting allogeneic cultured postnatal thymus tissue and supports its use in humans. (Markert M L, Watson T J, Kaplan I, Hale L P, Haynes B F, 1997, "The human thymic microenvironment during organ culture," *Clin Immunol Immunopathol.* January; 82(1):2 6-36; Hong R, Schulte-Wissermann H, Jarrett-Toth E, Horowitz S D, Manning D D, 1979, "Transplantation of cultured thymic fragments. II. Results in nude mice," *J Exp Med.*, 149(2): 398-415. Li B, Li J, Hsieh C S, Hale L P, Li Y J, Devlin B H, Markert M L, 2009, "Characterization of cultured thymus tissue used for transplantation with emphasis on promiscuous expression of thyroid tissue-specific genes," *Immunol Res.* 2009; 44 (1-3):71-83; Li B, Li J, Devlin B H, Markert M L, 2011, "Thymic microenvironment reconstitution after postnatal human thymus transplantation," *Clin Immunol., September;* 140(3): 244-59).

Complete DiGeorge Anomaly patients have defects in three glands that develop in the neck in the young embryo, the heart, the thymus and the parathyroid glands. Normally the heart and thymus descend into the chest and the parathyroid glands that regulate calcium levels, remain in the neck. Treatment of cDGA subjects with CTT led to the survival rates at two years of age of 75% compared to a survival rate of 6% in untreated subjects (unpublished data). In the literature, children generally die within two years in the absence of treatment. (Markert, et al., 2010). Of note, the CTT implantation does not affect the problems of the heart and the parathyroid gland that must be managed separately.

A first aspect of the present disclosure provides the surgical placement of allogeneic cultured postnatal thymus tissue-derived product in a recipient to induce tolerance to a solid organ transplant in an immunologically normal recipient. Such methods comprise, consist of, or consist essentially of removal of the thymus gland in an immunocompetent recipient followed by depleting the recipient's T cells with an induction immunosuppressive regimen, comprising one or more immunosuppressive agent such as with one or more antibody and/or one or more calcineurin inhibitor. The induction immunosuppressive regimen is administered in a therapeutically effective amount to deplete mature T cells in the subject and/or to suppress the recipient's T cells from rejecting the transplanted solid organ. A suitable solid human organ and a thymus gland from a deceased donor is obtained and the solid organ is transplanted into the recipient. A maintenance immunosuppressive regimen is administered for a period of time to suppress transplant rejection. The thymus gland from the deceased donor is subjected to a conditioning regimen for a period up to 21 days to aseptically process the donor thymus tissue in a thymus organ medium to produce partially T-cell depleted donor thymus tissue slices thereby comprising the allogeneic cultured postnatal thymus tissue-derived product. The partially T-cell depleted donor thymus tissue slices show areas positive for keratin AE1/AE3 scattered throughout the tissue, the presence of at least one Hassall body, CK14 staining scattered throughout the tissue and presence of intact nuclei. The allogeneic cultured postnatal thymus tissue-derived product is then surgically placed in the recipient, typically in the quadriceps muscle of the thigh. The allogeneic cultured postnatal thymus tissue-derived product enables the recipient to develop naïve T cells after implantation. All new T cells that develop are genetically recipient and are tolerant to both the recipient and to the donor. The dosage of thymus tissue slices is about 1,000-20,000 mm$^2$ of thymus tissue surface area/recipient body surface area in m$^2$. Following implantation, the allogeneic cultured postnatal thymus tissue-derived product induces thymopoiesis and tolerance in the subject.

Taking as an example a heart transplant, the donor would be a deceased donor. The thymus would be removed from the donor at the same time that the heart is removed. Heart transplantation is performed immediately with induction immunosuppression to decrease T cell numbers and suppress the remaining recipient T cells preventing them from attacking the donor heart. The donor thymus is processed to form human allogeneic cultured postnatal thymus tissue-derived product that can be used for implantation to induce tolerance after a period of at least 12 to about 21 days of conditioning. As a precaution, approximately half of the allogeneic cultured postnatal thymus tissue-derived product can be cryopreserved after conditioning, so that if there was a problem with later rejection of the heart necessitating the administration of high doses of steroids or other immunosuppressive agents to treat the rejection, and whereby the very high doses of steroid damage the allogeneic cultured postnatal thymus tissue-derived product, the cryopreserved allogeneic cultured postnatal thymus tissue-derived product would be available to implant after the rejection episode was controlled.

Importantly, after implantation of allogeneic cultured postnatal thymus tissue-derived product, immune tolerance is maintained even in the presence of infections. With other approaches such as co-stimulatory blockade, viral infections can led to loss of tolerance, because approximately a third of CD8 T cells have alloreactivity. When the immune system is activated to fight an infection, the alloreactive CD8 T cells start to reject the solid organ transplant. In contrast, when using thymus tissue processed into allogeneic cultured postnatal thymus tissue-derived product to induce tolerance, all potentially alloreactive T cells against the donor are deleted through the process of negative selection.

In an embodiment, the donor thymus tissue matches the HLA alleles in the donor organ that are not in the recipient. All new T cells that develop are genetically recipient and are tolerant to both the recipient and to the donor.

A second aspect of the present disclosure provides A method for promoting donor-specific tolerance to an allogeneic solid organ transplant obtained from a deceased donor, in a recipient in need of a solid organ transplant, the method comprising the steps of:
  (a) removal of the thymus of the recipient;
  (b) treating the recipient with an induction immunosuppressive regimen comprising one or more immunosuppressive agent to deplete the recipient's T cells and/or to suppress the recipient's T cells from rejecting the transplanted solid organ;
  (c) providing both a suitable solid human organ and a thymus gland from a deceased donor;
  (d) transplanting the solid human organ into the recipient;
  (e) treating the recipient with a maintenance immunosuppressive regimen;
  (f) providing an allogeneic cultured postnatal thymus tissue-derived product, wherein the allogeneic cultured postnatal thymus tissue-derived product is obtained from suitable thymus tissue of the solid organ donor; wherein the donor thymus tissue is subjected to a conditioning regimen for a period up to 21 days to produce allogeneic cultured postnatal thymus tissue-derived product; further wherein the conditioning regimen for the donor thymus tissue comprises aseptically processing the donor thymus tissue in a thymus organ medium to produce partially T-cell depleted donor thymus tissue slices; wherein the partially T-cell depleted donor thymus tissue slices show areas positive for cytokeratin (CK) (using antibody AE1/AE3) scattered throughout the tissue, the presence of at least one Hassall body, CK14 staining scattered throughout the tissue and presence of intact nuclei; and
  (g) implanting the allogeneic cultured postnatal thymus tissue-derived product into the recipient after 12 to 21 days of conditioning regimen, wherein the dosage of thymus tissue slices is about 1,000-20,000 mm$^2$ of thymus tissue surface area/recipient body surface area in m², and further wherein the implanted allogeneic cultured postnatal thymus tissue-derived product induces thymopoiesis and tolerance in the recipient.

In an embodiment, a method of promoting donor-specific tolerance to an allogeneic heart transplant in a recipient in need of a deceased donor heart is provided. The method comprises the following steps:
  (a) obtaining a suitable human heart from a deceased donor for transplantation;
  (b) removing the deceased donor thymus at the same time as the heart is obtained for conditioning into allogeneic cultured postnatal thymus tissue-derived product; wherein the donor thymus matches the HLA alleles in the donor transplanted organ;
  (c) treating the recipient with an induction immunosuppressive regimen comprising one or more immunosuppressive agents to deplete and/or suppress the recipient's T cells wherein the one or more immunosuppressive agents comprises glucocorticoids administered at the induction of anesthesia and after reperfusion;
  (d) transplanting the heart into the recipient;
  (e) treating the recipient with a maintenance immunosuppressive regimen comprising one or more immunosuppressive agents selected from the group consisting of a calcineurin inhibitor, an inosine monophosphate dehydrogenase inhibitor and an anti-thymocyte globulin for a period of time sufficient to prevent or suppress transplant rejection of the heart;
  (f) between day 12 and 21 providing an allogeneic cultured postnatal thymus tissue-derived product, wherein the allogeneic cultured postnatal thymus tissue-derived product is obtained from the donor thymus tissue, wherein the donor thymus tissue is subjected to a conditioning regimen for a period of from about 12 to about 21 days to produce allogeneic cultured postnatal thymus tissue-derived product; further wherein the conditioning regimen for the donor thymus tissue comprises aseptically processing the donor thymus tissue in a thymus organ medium to produce partially T-cell depleted donor thymus tissue slices; wherein the partially T-cell depleted donor thymus tissue slices show areas positive for keratin AE1/AE3 scattered throughout the tissue, the presence of at least one Hassall body, CK14 staining scattered throughout the tissue and presence of intact nuclei;
  (g) implanting a portion of the allogeneic cultured postnatal thymus tissue-derived product into the recipient, wherein the dosage of thymus tissue slices is about 1,000-20,000 mm² of thymus tissue surface area/recipient body surface area in m², and further wherein the implanted allogeneic cultured postnatal thymus tissue-derived product induces thymopoiesis and tolerance in the recipient; and
  (h) cryopreserving a portion of the allogeneic cultured postnatal thymus tissue-derived product to be used in the recipient in the event that there is an early rejection episode requiring high doses of steroids that would damage the portion of allogeneic cultured postnatal thymus tissue-derived product that was implanted in step (g).

In an embodiment, a method of promoting donor-specific tolerance to an allogeneic heart transplant in a recipient in need of a deceased donor heart is provided. The method comprises the following steps:
  (a) obtaining a suitable solid human heart from a deceased donor for transplantation;
  (b) removing the deceased donor thymus at the same time as the heart is obtained for conditioning into allogeneic cultured postnatal thymus tissue-derived product; wherein the donor thymus matches the HLA alleles in the donor transplanted organ;
  (c) treating the recipient with an induction immunosuppressive regimen comprising one or more immunosuppressive agents to deplete and/or suppress the recipient's T cells wherein the one or more immunosuppressive agents comprises glucocorticoids administered at the induction of anesthesia and after reperfusion;
  (d) surgically removing the heart and thymus of the recipient;
  (e) transplanting the donor human heart into the recipient;
  (f) treating the recipient with a maintenance immunosuppressive regimen comprising one or more immunosuppressive agents selected from the group consisting of a calcineurin inhibitor, an inosine monophosphate dehydrogenase inhibitor and an anti-thymocyte globulin for a period of time sufficient to prevent or suppress transplant rejection of the heart;
wherein, if the post-operative condition of the recipient is too unstable to allow weaning of the glucocorticoids and safely implanting the allogeneic cultured postnatal thymus tissue-derived product in the recipient, the allogeneic cultured postnatal thymus tissue-derived product is cryopreserved to be implanted at a later time when the recipient is stable, wherein the donor thymus tissue is subjected to a conditioning regimen for a period of from about 12 to about 21 days to produce allogeneic cultured postnatal thymus tissue-derived product; further wherein the conditioning regimen for the donor thymus tissue comprises aseptically processing the donor thymus tissue in a thymus organ medium to produce partially T-cell depleted donor thymus tissue slices; wherein the partially T-cell depleted donor thymus tissue slices show areas positive for keratin AE1/AE3 scattered throughout the tissue, the presence of at least one Hassall body, CK14 staining scattered throughout the tissue and presence of intact nuclei;
  (h) implanting a portion of the allogeneic cultured postnatal thymus tissue-derived product into the recipient after the patient is stable, wherein the dosage of thymus tissue slices is about 1,000-20,000 mm² of thymus tissue surface area/recipient body surface area in m², and further wherein the implanted allogeneic cultured postnatal thymus tissue-derived product induces thymopoiesis and tolerance in the recipient; and
  (i) cryopreserving a portion of the allogeneic cultured postnatal thymus tissue-derived product to be used in the recipient in the event that there is a rejection episode requiring high doses of steroids that would damage the portion of allogeneic cultured postnatal thymus tissue-derived product that was implanted in step (h).

A third aspect of the present disclosure provides a method for promoting donor-specific tolerance to an allogeneic solid organ transplant obtained from a living human donor, in a human recipient in need of a solid organ transplant, the method comprising the steps of:
  (a) removal of the thymus of the recipient;
  (b) treating the recipient with an induction immunosuppressive regimen comprising one or more immunosuppressive agent to deplete the recipient's T cells and/or to suppress the recipient's T cells from rejecting the transplanted solid organ;

(c) providing a suitable solid organ from a living human donor;
(d) transplanting the solid organ into the recipient;
(e) treating the recipient with a maintenance immunosuppressive regimen;
(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product was processed from thymus tissue from a thymus donor expressing HLA alleles matched to HLA alleles in the recipient that are not present in the solid organ transplant; wherein the donor thymus tissue was subjected to a conditioning regimen for a period up to 12 days; further wherein the conditioning regimen for the donor thymus tissue comprises aseptically processing the donor thymus tissue in a thymus organ medium to produce partially T-cell depleted thymus tissue slices, wherein the thymus tissue slices show areas positive for keratin AE1/AE3 scattered throughout the tissue, the presence of at least one Hassall body, CK14 staining scattered throughout the tissue and presence of intact nuclei upon completion of the conditioning regimen;
(g) thawing the cryopreserved allogeneic cultured postnatal thymus tissue-derived product; and
(h) implanting the thawed cryopreserved allogeneic cultured postnatal thymus tissue-derived product into the recipient, wherein the dosage of the cryopreserved allogeneic cultured postnatal thymus tissue-derived product is about 1,000-20,000 mm$^2$ of thymus tissue surface area/recipient body surface area in m$^2$, and further wherein the implanted allogeneic cultured postnatal thymus tissue-derived product induces thymopoiesis and tolerance in the recipient.

A fourth aspect of the present disclosure provides a method for promoting donor-specific tolerance to an allogeneic solid organ transplant obtained from a deceased human donor, in a human recipient in need of a solid organ transplant, the method comprising the steps of:
(a) removal of the thymus of the recipient;
(b) treating the recipient with an induction immunosuppressive regimen comprising one or more immunosuppressive agent to deplete the recipient's T cells and/or to suppress the recipient's T cells from rejecting the transplanted solid organ;
(c) providing a suitable solid organ from a living human donor;
(d) transplanting the solid organ into the recipient;
(e) treating the recipient with a maintenance immunosuppressive regimen;
(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product is processed from thymus tissue from a thymus donor expressing HLA alleles matched to HLA alleles in the recipient that are not present in the solid organ transplant; wherein the donor thymus tissue was subjected to a conditioning regimen for a period up to 12 days; further wherein the conditioning regimen for the donor thymus tissue comprises aseptically processing the donor thymus tissue in a thymus organ medium to produce partially T-cell depleted thymus tissue slices, wherein the thymus tissue slices show areas positive for keratin AE1/AE3 scattered throughout the tissue, the presence of at least one Hassall body, CK14 staining scattered throughout the tissue and presence of intact nuclei upon completion of the conditioning regimen;
(g) thawing the cryopreserved allogeneic cultured postnatal thymus tissue-derived product; and
(h) implanting the thawed cryopreserved allogeneic cultured postnatal thymus tissue-derived product into the recipient, wherein the dosage of the cryopreserved allogeneic cultured postnatal thymus tissue-derived product is about 1,000-20,000 mm$^2$ of thymus tissue surface area/recipient body surface area in m$^2$, and further wherein the implanted allogeneic cultured postnatal thymus tissue-derived product induces thymopoiesis and tolerance in the recipient.

In an embodiment of the second to the fourth aspect of the present disclosure, the allogeneic cultured postnatal thymus tissue-derived product of claim 63, wherein the thymus, on the day of harvest, demonstrates that >50% of areas are positive for keratin in a lacy staining pattern, that Hassall bodies are present, that CK14 stains in a lacy pattern, and that >90% of nuclei are intact.

A fifth aspect of the present disclosure provides an allogeneic cultured postnatal thymus tissue-derived product for implantation into a subject undergoing a solid organ transplant prepared by obtaining suitable thymus tissue from a donor wherein the donor thymus tissue is subjected to a conditioning regimen for a period up to 21 days; further wherein the conditioning regimen for the donor thymus tissue comprises aseptically processing the donor thymus tissue in a thymus organ medium to produce partially T-cell depleted donor thymus tissue slices; wherein the donor thymus tissue slices show, between days 5 and 9 post-harvest, areas positive for keratin AE1/AE3 scattered throughout the tissue, the presence of at least one Hassall body, CK14 staining scattered throughout the tissue and presence of intact nuclei; recovering the partially T-cell depleted donor thymus tissue slices as allogeneic cultured postnatal thymus tissue-derived product.

In an embodiment, the thymus, on the day of harvest, demonstrates that >50% of areas are positive for keratin in a lacy staining pattern, that Hassall bodies are present, that CK14 stains in a lacy pattern, and that >90% of nuclei are intact.

In an embodiment of the fifth aspect of the present invention, the allogeneic cultured postnatal thymus tissue-derived product is cryopreserved.

In an embodiment, the cryopreserved allogeneic cultured postnatal thymus tissue-derived product is maintained in liquid nitrogen for future use.

In another embodiment, the cryopreserved allogeneic cultured postnatal thymus tissue-derived product is maintained in a cryopreserved tissue bank.

In an embodiment, the allogeneic cultured postnatal thymus tissue-derived product is prepared from suitable thymus tissue from a donor comprising HLA alleles matched to HLA alleles in a proposed recipient that are not present in the solid organ transplant.

In an embodiment the HLA alleles are: HLA-A, HLA-B, HLA-C, HLA-DRB1, HLA-DQB1, HLA-DRB3, HLA-DRB4, HLA-DRB5, HLA-DQA1, HLA-DPB1, HLA-DPA1.

A sixth aspect of the present disclosure is a cryopreserved allogeneic cultured postnatal thymus tissue-derived product, prepared by method comprising the steps of:

(a) obtaining suitable thymus tissue from a donor;
(b) typing HLA alleles: HLA-A, HLA-B, HLA-C, HLA-DRB1, HLA-DQB1, HLA-DRB3, HLA-DRB4, HLA-DRB5, HLA-DQA1, HLA-DPB1, HLA-DPA1;
(c) subjecting the thymus tissue to a conditioning regimen for a period up to 12 days; wherein the conditioning regimen for the donor thymus tissue comprises aseptically processing the donor thymus tissue in a thymus organ medium to produce partially T-cell depleted donor thymus tissue slices; further wherein the donor thymus tissue slices show, on days 5 to 9, areas positive for keratin AE1/AE3 scattered throughout the tissue, the presence of at least one Hassall body, CK14 staining scattered throughout the tissue and presence of intact nuclei upon completion of the conditioning regimen;
(d) harvesting the partially T-cell depleted donor thymus tissue slices as allogeneic cultured postnatal thymus tissue-derived product;
(e) cryopreserving the allogeneic cultured postnatal thymus tissue-derived product in liquid nitrogen; and
(f) maintaining the cryopreserved allogeneic cultured postnatal thymus tissue-derived product in liquid nitrogen in a cryopreserved allogeneic cultured postnatal thymus tissue-derived product bank.

In an embodiment, the thymus, on the day of harvest, demonstrates that >50% of areas are positive for keratin in a lacy staining pattern, that Hassall bodies are present, that CK14 stains in a lacy pattern, and that >90% of nuclei are intact.

In an embodiment, the cryopreserved allogeneic cultured postnatal thymus tissue-derived product in liquid nitrogen is held for future use by the recipient.

A seventh aspect of the present disclosure provides a method of preparing the donor thymus for transplanting into a recipient subject. Such methods comprise, consist of, or consist essentially of culturing the donor thymus for up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, or up to about 21 days, and then surgically placing the cultured thymus tissue into the recipient, as further described herein. A culture period between about 6 and about 12 days results in good function. For successful transplantation of cryopreserved thymus tissue, the tissue is typically cultured for about 6 to about 12 days, and then cryopreserved.

An eighth aspect of the present invention provides an allogeneic cultured postnatal thymus tissue-derived product (CTT; RVT-802) for implantation into a subject undergoing a solid organ transplant manufactured by the method of subjecting thymus tissue from a suitable donor to a conditioning regimen for a period up to 21 days; wherein the conditioning regimen for the allogeneic cultured postnatal thymus tissue-derived product comprises aseptically processing the donor thymus tissue in a thymus organ medium to produce partially T-cell depleted thymus tissue slices, wherein the thymus tissue slices show areas positive for keratin AE1/AE3 scattered throughout the tissue, the presence of at least one Hassall body, CK14 staining scattered throughout the tissue and presence of intact nuclei.

In an embodiment of the eight aspect, the donor thymus, on the day of harvest, demonstrates that >50% of areas are positive for keratin in a lacy staining pattern, that Hassall bodies are present, that CK14 stains in a lacy pattern, and that >90% of nuclei are intact.

In an embodiment of the first to the fourth aspects of the present disclosure, the recipient's thymus is obtained by surgery.

In an embodiment of the first to the fourth aspects of the present disclosure, the recipient's thymus is obtained by robotic surgery.

In an embodiment of the first to the fourth aspects of the present disclosure, the recipient's thymus is obtained by thorascopic surgery.

In an embodiment of the first to the fourth aspects of the present disclosure, the solid organ is a portion of a whole organ.

In an embodiment, the method of the first to fourth aspects further comprises the step of cryopreserving peripheral blood mononuclear cells from the deceased donor for future use in a mixed lymphocyte reaction to demonstrate cellular tolerance.

In an embodiment, the mixed lymphocyte reaction to demonstrate cellular tolerance is performed using peripheral blood mononuclear cells from the recipient and cryopreserved peripheral blood mononuclear cells from the donor following the implantation of allogeneic cultured postnatal thymus tissue-derived product in accordance the implantation procedure of CTT in this specification In an embodiment, the mixed lymphocyte reaction to demonstrate cellular tolerance is performed with peripheral blood mononuclear cells from the recipient and cryopreserved peripheral blood mononuclear cells from the donor about 6 to 12 months following the implantation of allogeneic cultured postnatal thymus tissue-derived product.

In an embodiment, the mixed lymphocyte reaction to demonstrate cellular tolerance is performed with peripheral blood mononuclear cells from the recipient and cryopreserved peripheral blood mononuclear cells from the donor after naïve T cells constitute about 10% of total T cells in the recipient.

In an embodiment of the first to fourth aspects, the implanted allogeneic cultured postnatal thymus tissue-derived product induces thymopoiesis in the subject within 12 months following the implantation of allogeneic cultured postnatal thymus tissue-derived product.

In an embodiment of the first to fourth aspects, the development of tolerance is determined by a mixed lymphocyte reaction performed with cryopreserved peripheral blood mononuclear cells from the deceased donor and naïve T cells from the recipient.

In an embodiment of the first to fourth aspects, humoral tolerance is determined by the development of humoral immunity and the absence of donor reactive antibodies.

In an embodiment of the first to fourth aspects of the present disclosure, the solid organ transplant is a heart transplant, a kidney transplant, a liver transplant, a lung transplant, a heart/lung transplant, a pancreas transplant, an intestine transplant, a stomach transplant, an abdominal wall transplant, a craniofacial transplant, a scalp transplant, a penile transplant, a uterus transplant, a unilateral or bilateral upper limb transplant, a unilateral vascularized composite allograft, or combination thereof.

In an embodiment of the first to fourth aspects of the present disclosure, the method further comprises evaluating the recipient for HLA class I or HLA class II panel reactive antibodies ("PRA") score prior to transplanting the solid organ.

In an embodiment, the solid organ transplant is a heart transplant.

In an embodiment, the solid organ transplant is a pediatric heart transplant.

In an embodiment, the solid organ transplant is an adult heart transplant.

In an embodiment of the first to fourth aspects of the present disclosure, the method further comprises evaluating the recipient for HLA class I or HLA class II panel reactive antibodies ("PRA") score prior to transplanting the solid organ.

In an embodiment, recipients with HLA antibodies are cross-matched with potential donors.

In an embodiment, recipients with HLA antibodies are virtually cross-matched with UNET.

In a further embodiment, if a PRA score of >20% virtual cross-match is recorded, the method will further comprise the step of performing plasmapheresis in the operating room at the time of solid organ transplant in the recipient.

In a further embodiment, if a PRA score of >70% virtual cross-match is recorded, the method will further comprise the step of performing an actual prospective donor crossmatch and performing plasmapheresis in the operating room at the time of solid organ transplant in the recipient. Typically, transplants are not performed under these circumstance because of poor success rates.

In an embodiment of the first to fourth aspects of the present disclosure, the method further comprises the step of evaluating recipients with HLA antibodies by cross-matching virtually with UNET.

In an embodiment of the first to fourth aspects of the present disclosure, the method further comprises performing plasmapheresis in the operating room at the time of solid organ transplant in the recipient if the HLA panel reactive antibodies have a score >20%.

In an embodiment of the first to fourth aspects of the present disclosure, the method further comprises performing an actual prospective donor cross-match and performing plasmapheresis in the operating room at the time of solid organ transplant in the recipient if the HLA panel reactive antibodies have a score >70%.

In an embodiment, the solid organ is HLA-matched in for instance for living related donors and recipient for kidney, partial liver and partial intestine transplants.

In another embodiment, the solid organ is HLA-mismatched.

In an embodiment, the solid organ is HLA matched. In another embodiment, the HLA match is determined by typing HLA alleles: HLA-A, HLA-B, HLA-C, HLA-DRB1, HLA-DQB1, HLA-DRB3, HLA-DRB4, HLA-DRB5, HLA-DQA1, HLA-DPB1, HLA-DPA1 in the donor and the recipient.

In an embodiment, the solid organ transplants are ABO compatible.

In another embodiment, the solid organ is HLA-mismatched. In an embodiment, HLA-mismatched is determined by typing HLA-A, HLA-B, HLA-C, HLA-DRB1, HLA-DQB1, HLA-DQA1, HLA-DPB1, HLA-DPA1 in the donor and the recipient.

In an embodiment, the cultured thymus tissue slices are surgically implanted into the quadriceps thigh muscle of the subject.

In an embodiment, the cultured thymus tissue slices are surgically implanted into the body of the subject in an area other than the quadriceps.

In an embodiment, a portion of the allogeneic cultured postnatal thymus tissue-derived product is surgically implanted into the quadriceps thigh muscle of the recipient.

In another embodiment, wherein the remaining portion of the allogeneic cultured postnatal thymus tissue-derived product is cryopreserved in liquid nitrogen for future transplantation.

In an embodiment, the conditioning regiment is for a period of about 12 days to about 21 days.

In an embodiment, the conditioning period of the donor thymus tissue is about 5 days to about 21 days, or about 5 days, or about 6 days, or about 7 days, or about 8 days, or about 9 days, or about 10 days, or about 11 days, or about 12 days, or about 13 days, or about 14 days, or about 15 days, or about 16 days, or about 17 days, or about 18 days, or about 19 days, or about 20 days, or about 21 days.

It will be appreciated by the person of ordinary skill in the art that there are numerous potential induction immunosuppressive regimens and maintenance immunosuppressive regimens known in the art, and that a suitable induction and maintenance immunosuppressive agent may be selected by the person of skill in the art without undue burden. The following illustrative induction immunosuppressive regimens and maintenance immunosuppressive regimens are exemplary of the practice of the methods of the first to the fourth aspects of the invention and support the inventions as claimed.

In an embodiment, of the first to fourth aspects of the disclosure, the induction immunosuppressive regiment comprises an induction immunosuppressive agent selected from the group of glucocorticoid, anti-thymocyte globulin (rabbit), anti-thymocyte globulin (equine), and alemtuzimab.

In another embodiment, the ATG is antithymocyte globulin (rabbit).

In an embodiment, the induction immunosuppressive regimen comprises administration of a glucocorticoid. In an embodiment, the glucocorticoid comprises methylprednisolone. In another embodiment, the glucocorticoid is methylprednisolone sodium succinate. In a further embodiment, methylprednisolone sodium succinate is administered intravenously at no greater than 4 mg/kg/day.

In an embodiment, the induction immunosuppressive regimen comprises rabbit-derived anti-thymocyte globulin. In another embodiment, the rabbit-derived anti-thymocyte globulin is administered intravenously in a dose of about 1.5 mg/kg. In a further embodiment, the anti-thymocyte globulin is administered daily for four days. In another embodiment the ATG is equine derived ATG.

In an embodiment, the induction immunosuppressive regimen comprises basiliximab. In another embodiment, the basiliximab is administered at a dose of 10 mg intravenously for recipients less than 35 kg in body weight. In another embodiment, the basiliximab is administered at a dose of 20 mg intravenously for recipients more than 35 kg in body weight.

In an embodiment of the first to the fourth aspects of the present disclosure, the second immunosuppressive regimen comprises one or more immunosuppressive agent selected from the group consisting of a glucocorticoid, calcineurin inhibitor, an inosine monophosphate dehydrogenase inhibitor, azathioprine, and anti-thymocyte globulin ("ATG").

In an embodiment, the immunosuppressive agent of the maintenance immunosuppressive regiment is anti-thymocyte globulin (ATG).

In an embodiment, the ATG is administered intravenously at a dose of about 1.5 mg/kg for a period of 3-14 days starting with administration in the operating room.

In an embodiment, the anti-thymocyte globulin is administered daily for 3-14 days at about 15 mg/kg/day by intravenous administration.

In an embodiment, the first immunosuppressive regimen comprises alemtuzumab.

In an embodiment, the alemtuzumab is administered at a dose of about 0.25 mg/kg for 4 days intravenously for recipients less than 35 kg in body weight. In another, embodiment the alemtuzumab is administered at a dose of about 3 to 20 mg for 4 days intravenously for recipients more than 35 kg in body weight.

In an embodiment, the second immunosuppressive regimen comprises one or more immunosuppressive agent selected from the group consisting of a calcineurin inhibitor, and inosine monophosphate dehydrogenase inhibitor, or azathioprine.

In an embodiment, the immunosuppressive agent of the maintenance immunosuppressive regimen the immunosuppressive agent is a calcineurin inhibitor. In an embodiment, the immunosuppressive agent of the maintenance immunosuppressive regimen the immunosuppressive agent is an inosine monophosphate dehydrogenase inhibitor.

In an embodiment, the immunosuppressive regimen comprises an inosine monophosphate dehydrogenase inhibitor, for example, mycophenolate mofetil. In an embodiment, mycophenolate mofetil is administered intravenously in a dose of about 15 to about 25 mg/kg. In an embodiment, the mycophenolate mofetil is administered intravenously two to three times a day.

In another embodiment, inosine monophosphate dehydrogenase inhibitor is mycophenolic acid. In another embodiment, the mycophenolic acid is administered at a dose of about 25 to about 50 mg/kg in 2 or 3 divided doses.

In an embodiment, the mycophenolic acid is administered at a dose of about for children about 400 mg/m²/dose twice daily with a maximum dose 720 mg, or BSA 1.19 to 1.59 m² about 540 mg twice daily, or for BSA >1.58 m² about 720 mg twice daily.

In an embodiment, the mycophenolate mofetil is administered for children at a dose of about 15 to about 25 mg/kg/dose twice a day or for adults about 1500 mg orally or intravenously twice daily and adjusted for a WBC of >3500.

In an embodiment of the first to fourth aspects of the present disclosure, the second immunosuppressive regimen may further comprise a glucocorticoid selected from the group consisting of methylprednisolone, prednisone and prednisolone. In an embodiment, the dose of glucocorticoid is kept below 4 mg/kg/day.

In an embodiment, the glucocorticoid is administered in a tapered dosage reduction, as described elsewhere in the present disclosure.

In another embodiment of the first to fourth aspects of the present disclosure, the calcineurin inhibitor is tacrolimus. In another embodiment, the calcineurin inhibitor is cyclosporine A.

In another embodiment of the first to fourth aspects of the present disclosure, the administration of the second immunosuppressant regimen is weaned after naïve T cells reach 10% of total T cells. In yet another embodiment, the second immunosuppressant regimen is weaned after transplantation of allogeneic cultured postnatal thymus tissue-derived product.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the principles disclosed herein, and the advantages thereof, reference is made to the following descriptions taken in conjunction with the accompanying drawings, in which:

FIG. 6E and FIG. 6F are predominantly epithelial cells. Condensation of the epithelium of the subcapsular cortex occurs as the thymocytes are depleted with time. Similar condensation occurs in medullary areas of the thymus. Photo by Laura P. Hale, MD, PhD, Department of Pathology, Duke University.

FIG. 11A. Day 0; FIG. 11B. day 5; FIG. 11C. day 9; FIG. 11D. Day 12; and FIG. 11E. day 21. The structure of the thymic epithelial network remains intact as the culture progresses. Bar represents 400 μm. Photo by Laura P. Hale, MD, PhD, Department of Pathology, Duke University.

FIG. 12A depicts the cortex at day 9 after exposure to forced degradation conditions. FIG. 12B depicts the cortex at day 21 after exposure to forced degradation conditions. In FIG. 12A the smear of blue is DNA released from cells. The majority of cells show evidence of degradation although small foci of cells with intact nuclei can be identified. Photo by Laura P. Hale, MD, PhD, Department of Pathology, Duke University.

FIG. 17C is a photograph of CTT transplanted under the kidney capsule of an LW rat. FIG. 17D is a photograph of a thymus graft harvested at 6 months after transplantation. Arrows indicate the CTT under the kidney capsule.

FIG. 18A shows a comparison of medullary differentiation in H&E stained fresh thymus tissue (top frame) and CTT cultured for 5 days (bottom frame), as described in Example 5. FIG. 18B shows the typical lacey pattern observable in CTT cultured for 5 days (bottom frame) when stained for cytokeratin compared with fresh thymus tissue (top frame), as described in Example 5. FIG. 18C shows fresh thymus tissue (top frame) and CTT depleted of T cells (bottom frame) when stained for Ki-67. FIG. 18D shows fresh thymus tissue stained for CD3 (top frame) and CTT thymus tissue cultured for 5 days and then stained for CD3 (bottom frame). The brown stain noted in the CD3 stained CTT (FIG. 18D, bottom frame), likely represents some viable cells plus the detritus of dead T cells that have not washed out of the tissue.

FIG. 19A shows a comparison of medullary differentiation in H&E stained fresh thymus tissue (top frame) and CTT cultured for 5 days (bottom frame), as described in Example 5. FIG. 19B shows the typical lacey pattern observable in CTT cultured for 5 days (bottom frame) when stained for cytokeratin compared with fresh thymus tissue (top frame), as described in Example 5. FIG. 19C shows fresh thymus tissue (top frame) and CTT depleted of T cells (bottom frame) when stained for Ki-67. FIG. 19D shows fresh thymus tissue stained for DC3 (top frame) and CTT thymus tissue cultured for 5 days and then stained for CD3 (bottom frame). The brown stain noted in the CD3 stained CTT (FIG. 19D, bottom frame), likely represents some viable cells plus the detritus of dead T cells that have not washed out of the tissue.

In FIG. 30A, after immunosuppression was removed and the BN heart transplanted, the BN heart was quickly rejected and thus is very large because of all the inflammation. The LW heart is normal sized for the heart pumping blood through the body. The DA heart is small as it was placed in the abdomen and didn't need to pump blood. In FIG. 30B, the rat is immunodeficient and cannot reject either the BN or DA heart after immunosuppression is removed. This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.

FIG. 31A depicts quantification of inflammatory cells in the primary abdominal DA cardiac allograft. The syngeneic control shows that LW rats do not reject LW hearts. The DA control shows that LW rats do reject DA hearts. The CTT group does not reject the DA heart because of tolerance. The group without CTT doesn't reject the DA heart because of immunodeficiency from lack of a thymus. FIG. 31B depicts quantification of inflammatory cells in secondary cervical BN cardiac allografts. The syngeneic control shows that LW rats do not reject LW hearts. The BN control shows that LW rats do reject BN hearts. The CTT group rejects the BN heart because it is immunocompetent. The group without CTT doesn't reject the BN heart because of immunodeficiency from lack of a thymus.

FIG. 32A shows representative histogram plots for post-transplant donor-specific alloantibody (anti-DA and anti-BN antibodies) measured by T cell flow crossmatch. The upper left panel of FIG. 32A (DA control) shows the development of anti-DA antibody (thick line) in a normal LW rat after receiving a heterotopic abdominal DA heart transplant. The upper middle panel of FIG. 32A shows lack of anti DA antibody in the LW rats that received CTTT; this indicates tolerance. The upper right panel shows no response by the LW rats without CTTT; this reflects the immunodeficiency of the rats after thymectomy and T cell depletion without receipt of a donor thymus. The lower left panel of FIG. 32A shows normal anti BN antibody formed by a normal LW rat receiving a cervical BN heart. The lower middle panel of FIG. 32A shows a normal response of the LW rats with CTTT against BN after receiving a cervical BN heart transplant, showing immunocompetence and ability to reject $3^{rd}$ party. The lower right panel of FIG. 32A shows that there is no response of the LW rats without CTTT against BN after having received a cervical BN heart transplant, showing immune-incompetence and lack of ability to reject $3^{rd}$ party. FIG. 32B shows levels of anti-DA antibody after primary DA heart transplantation. The LW rats with CTTT from an LW×DA thymus donor do not make anti-DA antibody after a DA heart transplant because they are tolerant to DA. The LW rats without CTTT do not make anti-DA antibody after DA heart transplantation because they are immunodeficient. FIG. 32C shows levels of anti-BN antibody after secondary cervical BN heart transplantation. The LW rats with CTTT from an LW×DA donor make antibodies against BN showing immunocompetence against $3^{rd}$ party. The LW rats without CTTT do not make antibodies against BN showing immunoincompetence. This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.

FIG. 33P shows Ki-67 staining of proliferating T cells at the same time points. Staining with Ki-67 is absent by day 6 (FIG. 33N), as the T cells have mainly died. This figure shows the ability to cryopreserve non-human primate thymus similarly to how cultured thymus tissue will be cryopreserved for patients.

DETAILED DESCRIPTION OF THE INVENTION

Figure 1:
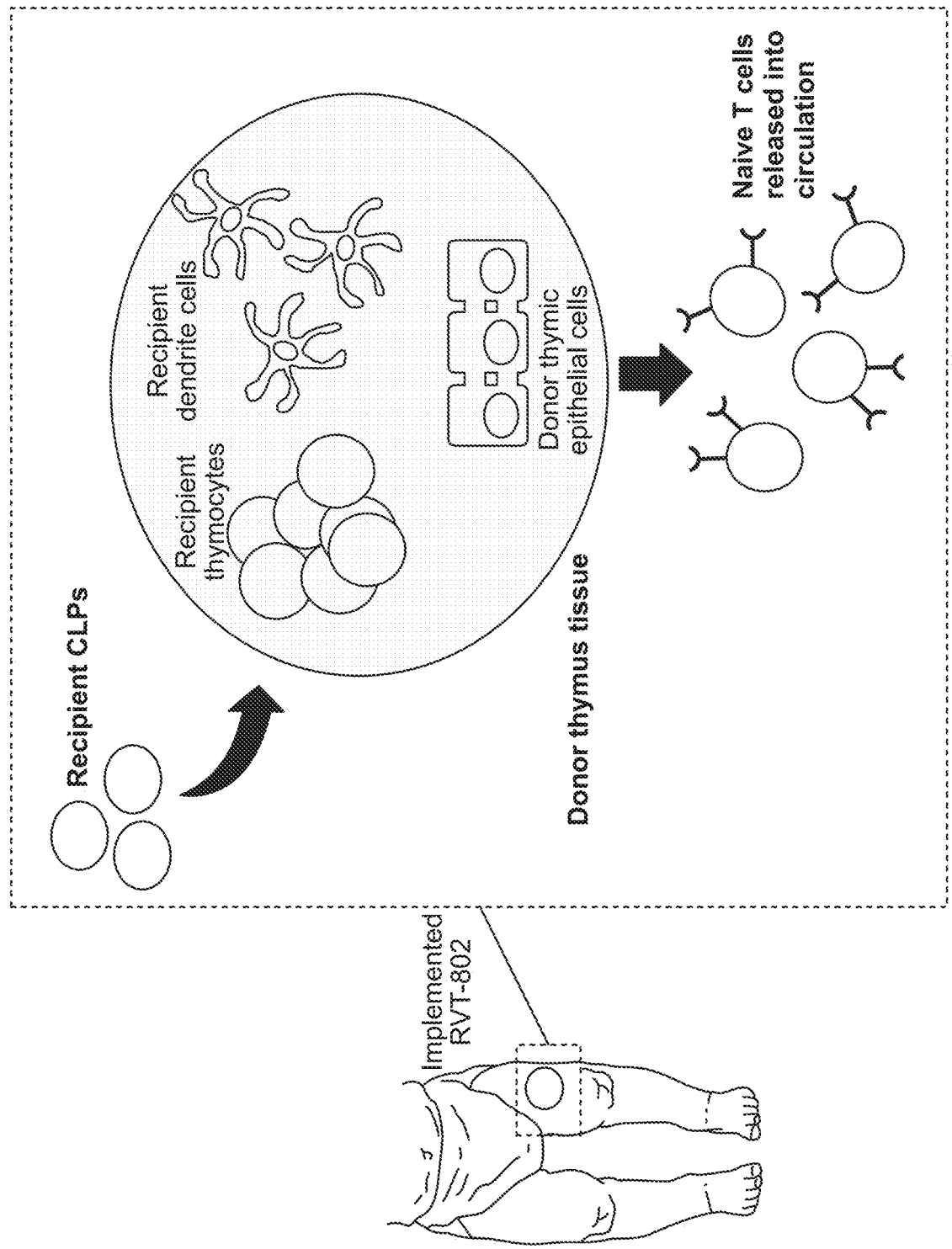
FIG. 1 shows a schematic of the mechanism of action of allogeneic, cultured postnatal thymus tissue-derived product (e.g., CTT, RVT-802) following administration for immune reconstitution in congenital athymia.
Figure 2:
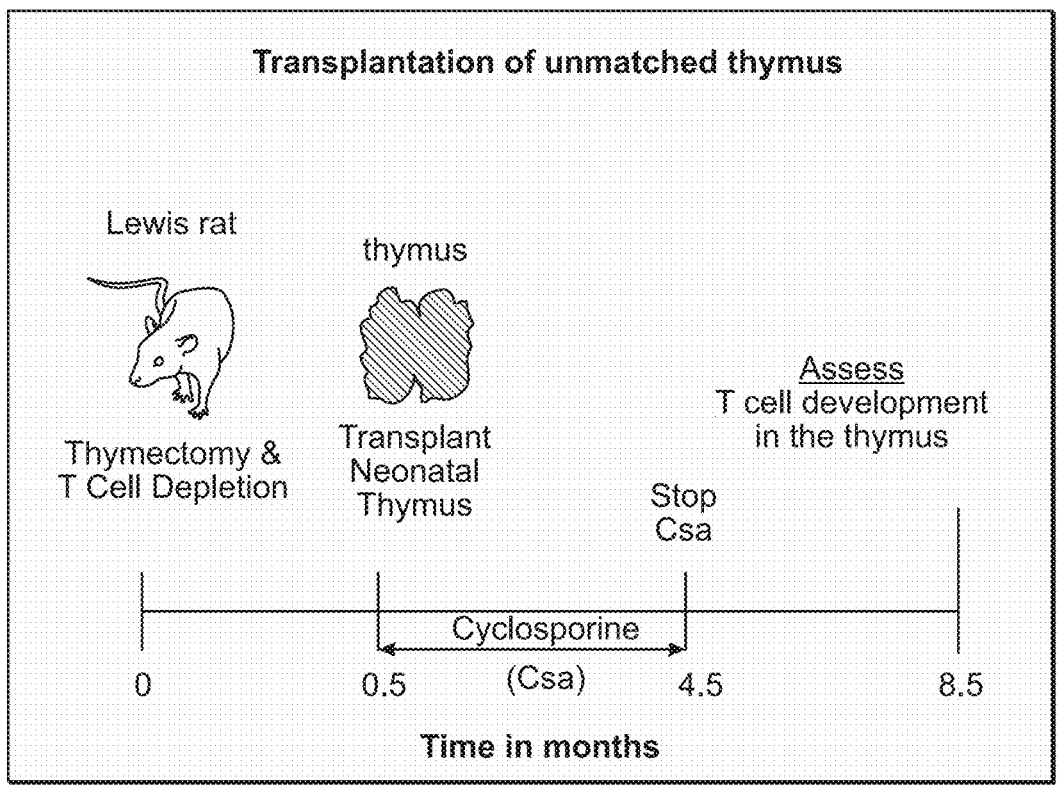
FIG. 2 shows a schematic of the steps for reconstituting the immune system in a rat, as described elsewhere in Example 5, by removing the thymus in an immunologically normal Lewis rat, administering an antibody to kill the recipient rat's T cells, implanting cultured neonatal thymus tissue from a donor rat into the recipient rat, administering an immunosuppressive agent for about 4 months and evaluating T cell development in the recipient rat. Of note, all rats in the treatment group had over 10% naïve T cells prior to stopping the cyclosporine.
Figure 3:
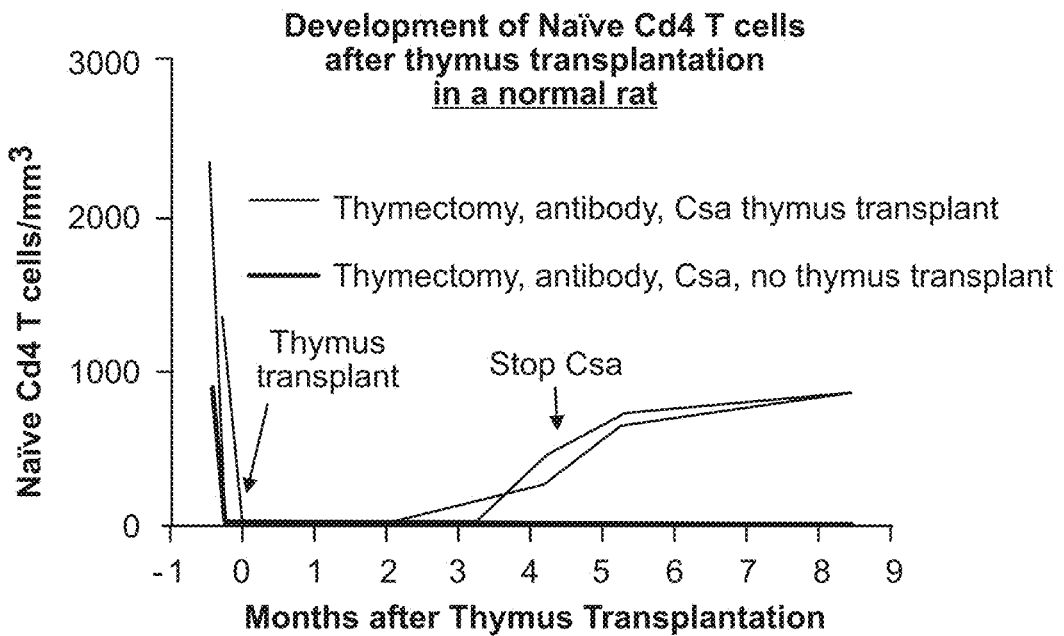
FIG. 3 shows the development of naïve T cells in two experimental recipient rats of Example 5 (rising lines on right) versus two controls rat not receiving a thymus tissue implant (thick lines at baseline).
Figure 4:
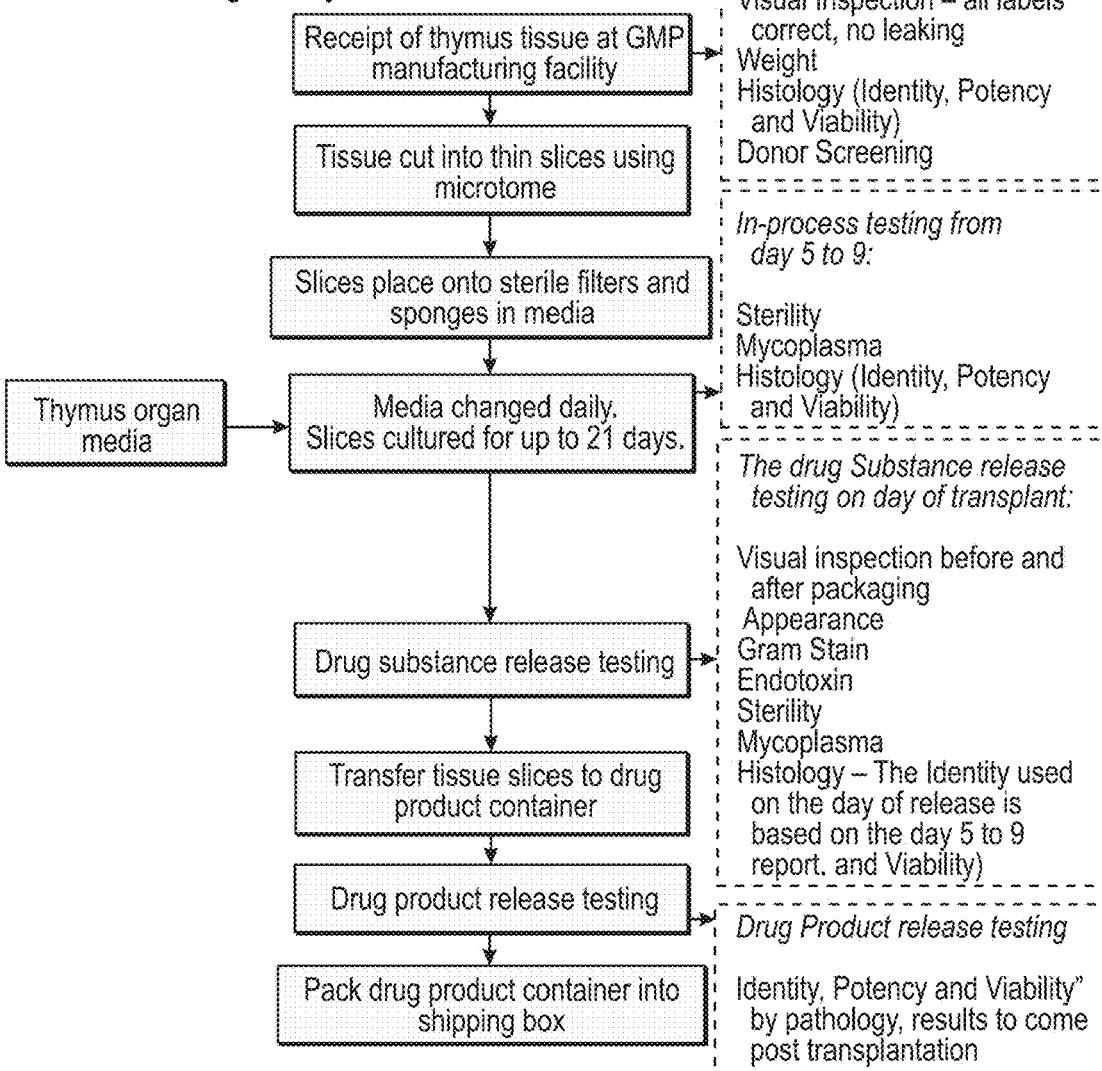
FIG. 4 shows a schematic of the manufacturing process for harvesting a thymus from a donor, culturing thin slices of the donor thymus tissue for up to 21 days and implanting the cultured thymus tissue in the quadriceps muscle of the recipient.

The titles, headings and subheadings provided herein should not be interpreted as limiting the various aspects of the disclosure. Accordingly, the terms defined below are more fully defined by reference to the specification in its entirety. All references cited herein are incorporated by reference in their entirety.

Unless otherwise defined, scientific and technical terms used herein shall have the meanings that are commonly understood by those of ordinary skill in the art. Further, unless otherwise required by context, singular terms shall include pluralities and plural terms shall include the singular. In this application, the use of "or" means "and/or" unless stated otherwise. In the context of a multiple dependent claim, the use of "or" refers back to more than one preceding independent or dependent claim in the alternative only.

It is further noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

The instant invention is most clearly understood with reference to the following definitions:

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of +/−10%. As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

As used herein, the term "animal" includes, but is not limited to, humans and non-human vertebrates such as wild, domestic, and farm animals. The animal can also be referred to as a "subject."

As used here, "biocompatible" refers to any material, which, when implanted in a mammal, does not provoke an adverse response in the mammal.

"Chronic transplant rejection" generally occurs in humans within several months to years after engraftment, even in the presence of successful immunosuppression of acute rejection. Fibrosis is a common factor in chronic rejection of all types of organ transplants.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, un-recited elements or method steps. Additionally, a term that is used in conjunction with the term "comprising" is also understood to be able to be used in conjunction with the term "consisting of" or "consisting essentially of."

As used herein, a "graft" refers to a tissue or organ that is implanted into an individual, typically to replace, correct or otherwise overcome a defect. The tissue or organ may consist of cells that originate from the same individual; this graft is referred to herein by the following interchangeable terms: "autograft", "autologous transplant", "autologous implant" and "autologous graft". A graft from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein, the term "HLA matched" refers to a donor recipient pair in which none of the HLA antigens are mismatched between the donor and recipient. HLA matching in the methods of the invention comprise: HLA alleles: HLA-A, HLA-B, HLA-C, HLA-DRB1, HLA-DQB1, HLA-DQA1, HLA-DPB1, HLA-DPA1.

As used herein, the term "HLA mismatched" refers to matching in a donor and recipient HLA antigens, typically with respect to HLA-A, HLA-B, HLA-C, HLA-DRB1, HLA-DQB1, HLA-DQA1, HLA-DPB1, HLA-DPA1 wherein an HLA mismatch between the donor and recipient occurs. In some cases, one haplotype is matched and the other is mismatched. This situation is frequently found with organs from living or deceased donors. An HLA mismatch in donor-recipient pairs results in an increased risk of graft rejection relative to HLA-matched pairs.

As background to the foregoing definitions, HLA antigens correspond to "human leukocyte antigens," which are protein molecules expressed on the surface of cells that confer a unique antigenic identity to these cells. They are also known as "major histocompatibility complex antigens." Thus the MHC or HLA antigens are target molecules that are recognized by T-cells as being "self" or "non-self" If the HLA antigens are derived from the same source of hematopoietic stem cells as the immune effector cells they are considered "self." If, the HLA antigens are derived from another source of hematopoietic reconstituting cells, they are considered "non-self."

Two main classes of HLA antigens are recognized: HLA class I and HLA class II. HLA class I antigens (A, B, and C in humans) render each cell recognizable as "self." HLA class II antigens (DRB1, DPB1, DPA1, DQB1, and DQA1 in humans) are involved in reactions between lymphocytes and antigen presenting cells. Both classes of HLA antigens have been implicated as targets of rejection of transplanted organs.

HLA genes are clustered on human chromosome position 6p21. This cluster of genes encodes the six classical transplantation HLA genes. The segment of 6p21 also encodes genes encoding proteins having important roles in the regulation of the immune system and other fundamental molecular and cellular processes. The complete cluster measures roughly 3.6 Mb, with at least 224 gene loci. As a result of the clustering certain "haplotypes" occur (the set of alleles present on a single chromosome). The haplotypes inherited from one parent tend to be inherited as a group. The set of alleles inherited from each parent forms a haplotype, in which some alleles tend to be associated together. HLA matching is used to identify the recipient's haplotypes and help in identifying suitable matching donors. Certain haplotypes are more prevalent than others and they vary in frequency in different racial and ethnic groups.

As used herein, the phrase "in need thereof" means that the subject has been identified as having a need for the particular method or treatment. In some embodiments, the identification can be by any means of diagnosis. In any of the methods and treatments described herein, the subject can be in need thereof.

As used herein, the phrase "integer from X to Y" means any integer that includes the endpoints. For example, the phrase "integer from X to Y" means 1, 2, 3, 4, or 5.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein the term "organ" refers to a solid vascularized organ that performs a specific function or group of functions within an organism. The term organ includes, but is not limited to heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus.

As used herein, the terms "prevent", "preventing" and "prevention" refer to the administration of therapy to an individual who may ultimately manifest at least one symptom of a disease, disorder, or condition, but who has not yet done so, to reduce the chance that the individual will develop the symptom of the disease, disorder, or condition over a given period of time. Such a reduction may be reflected, for example, in a delayed onset of the at least one symptom of the disease, disorder, or condition in the patient.

As used herein, the terms "subject," "individual" or "patient," used interchangeably, means any animal, including mammals, such as mice, rats, other rodents, rabbits, dogs, cats, swine, cattle, sheep, horses, or primates, such as humans.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

The term "tissue" as used herein refers to any type of tissue in human or animals, and includes, but is not limited to, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

"Tissue bank" in the context of the present disclosure refers to long-term storage of cryopreserved allogeneic cultured postnatal thymus tissue-derived product stored under liquid nitrogen. General guidance for establishment of a repository for allogeneic cultured postnatal thymus tissue-derived product may be drawn from Guidance for Industry. Current Good Tissue Practice (CGTP) and Additional Requirements for Manufacturers of Human Cells, Tissues, and Cellular and Tissue-Based Products (HCT/Ps) available at https://www.fda.gov/downloads/BiologicsBloodVaccines/GuidanceComplianceRegulatoryInfor mation/Guidances/Tissue/UCM285223.pdf.

"Tissue engineer(ing)(-ed)" refers to the process of generating tissues ex vivo for use in tissue replacement or reconstruction. Tissue engineering is an example of "regenerative medicine" which encompasses approaches to the repair or replacement of tissues and organs by incorporation of cells, genes or other biological building blocks, along with bioengineered materials and technologies.

The term "transplant rejection" encompasses both acute and chronic transplant rejection. "Acute rejection" is the rejection by the immune system of a tissue transplant recipient when the transplanted tissue is immunologically foreign. Acute rejection is characterized by infiltration of the transplant tissue by immune cells of the recipient, which carry out their effector function and destroy the transplant tissue. The onset of acute rejection is rapid and generally occurs in humans within a few weeks after transplant surgery. Generally, acute rejection can be inhibited or suppressed with immunosuppressive drugs such as rapamycin, cyclosporin A, anti-CD40L monoclonal antibody and the like.

As used herein, the terms "treat," "treated," or "treating" mean both therapeutic treatment and prophylactic measures wherein the object is to slow down (lessen) an undesired physiological condition, disorder or disease, or obtain beneficial or desired clinical results. For example, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease.

As described herein, any concentration range, percentage range, ratio range or integer range is to be understood to include the value of any integer within the recited range and, when appropriate, fractions thereof (such as one tenth and one hundredth of an integer), unless otherwise indicated. Ranges are approximate and may vary by more than an integer.

Units, prefixes, and symbols are denoted in their Systéme International de Unites (SI) accepted form. Numeric ranges are inclusive of the numbers defining the range. Measured values are understood to be approximate, taking into account significant digits and the error associated with the measurement.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

Harvesting of Donor Thymus Tissue.

Donor thymus tissue may be obtained during post-natal heart operations with the informed consent of the donor's family. The removal of some thymus may be necessary to reveal the operative site. Thus, a portion of the thymus may be removed during the heart operation in post-natal heart surgeries, due to the nature of the surgical procedure.

During postnatal heart surgeries a portion of the thymus tissue may be discarded during the surgical procedure. For all heart surgeries, whether or not the thymus is being screened for transplantation, the surgeon places the thymus tissue that has been removed into a sterile container.

Thymus tissue donors for thymus tissue transplantation in infants with complete DiGeorge syndrome have been infants under nine months of age. The drug substance allogeneic cultured postnatal thymus tissue-derived product is manufactured by processing and culturing the discarded thymus tissue as described herein.

Consent for use of the thymus in cultured thymus tissue transplantation may be obtained before or after the thymus is harvested. However, consent allowing blood to be obtained from the infant prior to undergoing bypass is necessary and is always obtained prior to the surgery. This blood sample is used for donor screening.

The discarded thymus tissue is placed into a sterile container. Routine testing is done on the donor and donor's birth mother in accordance with FDA guidelines for tissue transplantation. Tissue type matching is not required in the surgical procedures described herein, but such tissue type matching can be performed in certain situations.

Tissue may be processed immediately or stored refrigerated overnight for next day processing. If the thymus tissue is to be stored overnight, the tissue is aseptically added to thymus organ medium ("TOM" medium described below) sufficient to completely cover the thymus tissue in the original container. The container with the thymus is placed in refrigerator until ready to process the next day.

Overview of Conditioning of Thymus Tissue

The conditioning regimen depletes the donor thymocytes from the cultured thymus tissue slices. Based on in vitro data (immunohistochemistry) a culture period between 12 and 21 days preserves the epithelial network as assessed using cytokeratin antibodies. The culturing is preferably done at 37° C. in a 5% $CO_2$ incubator.

For successful culture, the thymus tissue is preferably sliced and put on Millipore® cellulose or equivalent filters and placed on surgical sponges in tissue culture dishes. The medium comprises the thymus organ medium (TOM) and is changed daily.

The thymus on receipt is assessed by pathology. The test for identity must show >50% of areas positive for keratin in lacy staining pattern. The test for potency must show Hassall bodies; it must also show CK14 staining in lacy pattern. The test for viability must show >90% intact nuclei observed in sections. The lot release for the tissue is done on one day between day 5 and day 9 (inclusive) and is performed by pathology. For identity, areas on tissue between days 5 and 9 must be positive for keratin, AE1/AE3. For potency, the cultured thymus tissue between days 5 and 9 must show cytokeratin CK14 staining scattered throughout, and there must be at least one Hassall body identified. For viability, the cultured thymus tissue between days 5 and 9 must show intact nuclei.

In an embodiment, the thymus tissue slices are conditioned for about 12 days and then cryopreserved. In another embodiment all of the thymus tissue slices are conditioned for about 12 days, then about half are implanted in the recipient and the remaining thymus tissue slices are cryopreserved for future use.

Within 24 hours of harvest, the thymus is cut into thin slices. The slices are held in culture for 12-21 days. This culturing process, as described in detail below, depletes viable donor T cells and ultimately enables the surgically implanted tissue slice to reconstitute the athymic subject's immune system, albeit at potentially lower, but immunologically effective T cell levels.

The culturing process, as outlined below, significantly modifies the biological characteristics of the donor thymus tissue and constituent cells contained therein in the following manner to optimize the effective therapeutic properties of the CTT slices.

The culturing process assures that a defined composition of the cultured cells/tissue having the pre-requisite biological characteristics is obtained in a manner suitable for surgical implantation into a subject to enable reconstitution of the subject's immune system.

The culturing process results in a loss of thymocytes and relative enrichment of thymic epithelial cells and other stromal cells in the donor thymus tissue slices.

The culturing process further results in depletion of thymocytes and maintenance of TECs to enable reconstitution of the recipient's immune system and allows tolerance to develop in the recipient to HLA antigens in the donor thymus.

Overall, the manufacturing process is designed to deplete thymocytes from the donor thymus tissue and to preserve the functional architecture of the thymic stroma (thymic epithelial cells and fibroblasts).

In an embodiment, processed donor thymus tissue is an engineered thymus tissue product capable of inducing tolerance to the thymus tissue types (HLA antigens) in a subject in need thereof following a surgical implantation procedure.

To keep the sliced thymus tissue viable, the thymus sections are placed on Millipore® cellulose filters and surgical sponges inserted into medium-containing tissue culture dishes. The culture medium in each tissue culture dish is replaced daily from the day of harvest from the donor to the day of implantation (day 12 to day 21).

The culturing of donor thymus tissue depletes thymocytes in such processed tissue which minimizes the risk of graft versus host disease ("GvHD"), which could be highly problematic in profoundly immunodeficient subjects following a thymectomy.

During the first few days in culture, many thymocytes "fall out" of the tissue slices into the culture medium and are discarded during media changes. As culturing continues during the culturing period, donor thymocytes continue to die but their cellular remnants are retained within the CTT slices.

Without being bound by theory, the presence of these non-viable thymocytes and their remnants that lack nuclei are hypothesized to be important for the intended function of the tissue-engineered product, because they help to preserve the open pockets in the three-dimensional network of thymic epithelial cells that is necessary for the entry of recipient bone marrow stem cells post-treatment. The importance of having "space" for the entering bone marrow stem cells is supported by experience with patient DIG003 in Markert, 1999 (See list of reference infra). The patient described in the foregoing reference had been given a very large dose of steroids (40 mg/kg/day×3 days of methylprednisolone) 35 days after CTT transplantation, which led to apoptosis of the thymocytes and condensation of the epithelium. No naïve T cells ever developed, and the patient succumbed to infection. At autopsy, the inserted thymus was a mass of viable cuboidal epithelium with no space between the epithelial cells for thymocytes to enter.

During the culturing period, HLA typing is performed to see if the patient (recipient) and donor tissue share any HLA alleles. Anti-HLA antibody testing is performed in the recipient to determine if the recipient has any antibodies against HLA antigens in the thymus. If the recipient has antibodies targeting the donor's MHC, another thymus would be sought. The donor and the mother of the donor are checked for infection per the FDA guidance document "Guidance for Industry. Eligibility Determination for Donors of Human Cells, Tissues and Cellular and Tissue-Based Products (HCT/Ps)" and more recent Guidance documents. The tissue is processed aseptically under the Code of Federal Regulations (CFR) 1271 subpart D "Current Good Tissue Practice."

Following review of the batch records and QC testing the tissue is released from manufacturing and provided to the surgical team for transplantation, the tissue is surgically implanted into the recipient, as described previously.

Cultured thymus tissue is produced in a process more completely described below and in the Examples set forth in this specification.

In summary, the culturing process of the harvested thymus tissue significantly modifies the biological characteristics of the donor tissue and constituent cells contained therein in the following manners: loss of donor thymocytes and enrichment of thymic epithelial cells and other stromal cells, and depletion of donor thymocytes modifies the physiologic functions of the tissue (e.g., secretion of cytokines and growth factors) as well as its structural properties.

During the first few days in culture, many thymocytes "fall out" of the tissue slices into the culture medium and are discarded during media changes.

Manipulations that occur during the manufacturing process result in changes in the gross and histologic appearance of the resulting cells contained in the finished product as compared with the source or starting material obtained from the donor.

Figure 15:
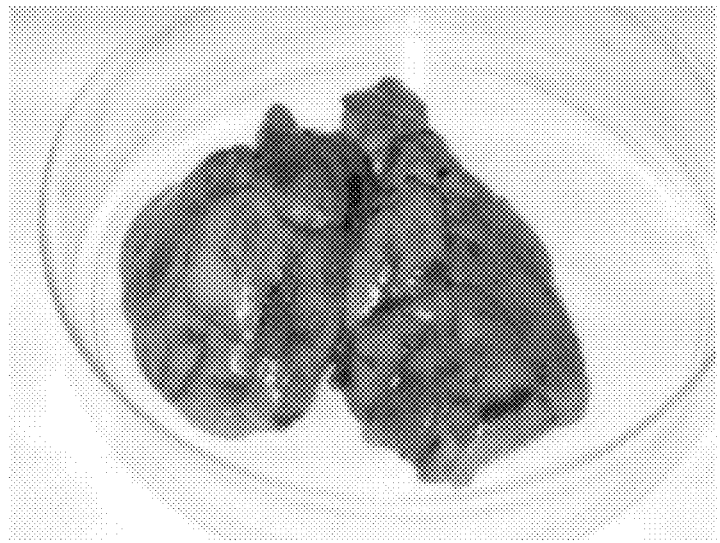
FIG. 15 is a photograph of freshly harvested thymus tissue.
Figure 16:
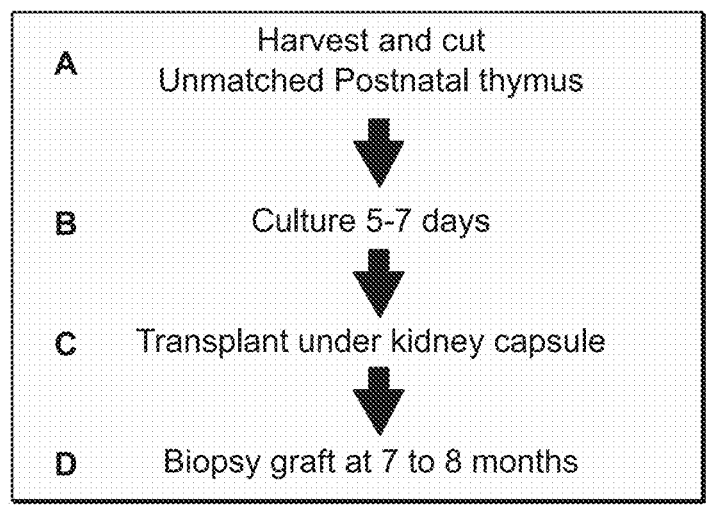
FIG. 16 is a schematic describing the harvesting, culturing, transplantation and biopsy of the transplantation of CTT under the rat kidney capsule, as presented in Example 5.

Thymus tissue during the first few days of culturing appears red due to residual blood on and within the tissue. See, e.g., FIG. 15.

Between days 5 to 9 viable tissue is observed minus the blood contamination that was evident on day 1.

During the remaining days of culturing the depth of the tissue decreases as thymocytes are depleted. The decrease in density of thymocytes in the tissue is documented by immunohistochemistry and described in detail below.

On day 0 following harvesting of the discarded thymus tissue the tissue is densely populated with viable thymocytes embedded in a stroma that contains thymic epithelial cells and fibroblasts. AE1/AE3 and CK14 staining confirm the presence of cytokeratin (CK)-positive thymic epithelial cells, which are characteristic of normal thymus. The thymic epithelial cells form a lacy three-dimensional network with delicate processes that surround neighboring thymocytes.

During the culturing process, slices of thymus are cultured, as described below. Numerous thymocytes are washed out of the tissue, especially over the first 3 days. This depletion can be identified histologically as early as day 2 by H&E stains that show decreased thymocyte density, particularly in medullary areas. The majority of the thymocytes that remain in the tissue show nuclear changes consistent with apoptosis and/or necrosis or demonstrate karyolysis (complete loss of nuclei). Many of these dead thymocytes and their cellular remnants remain present throughout the thymus tissue and are believed to prevent total collapse of the space between epithelial cells.

Some epithelial condensation can be seen in external areas, such as in the subcapsular cortex where loss of thymocytes has led the epithelial cell network to collapse. These condensed subcapsular cortical epithelial cells can form linear arrays several cell layers thick, which may add to the mechanical strength of the slices. Some medullary epithelium may also condense to form patches of contiguous epithelial cells.

Death of thymocytes continues as the culture progresses, with retention of necrotic thymocyte debris within the tissue. Further condensation of medullary and subcapsular cortical epithelium is minimal between approximately days 7 and 19 of culture.

Areas with epithelial architecture similar to normal thymus can still be observed late in culture for each thymus using the AE1/AE3 stains. For tissues cultured longer, the epithelial architecture of cortex and medulla can still be readily discerned; for instance, Hassall bodies remain in the medullary areas. The degree of thymocyte depletion, however, results in a substantially different overall histologic appearance on H&E compared to that of normal thymus at time points later than day 0.

Detailed Culturing of Thymus Tissue.

The general procedure in preparing allogeneic cultured thymus tissue-derived product is that thymus tissue for infants with complete DiGeorge syndrome is obtained as discarded tissue from infants under the age of 9 months undergoing cardiac surgery, as described previously. For solid organ transplantation, discarded thymus will be obtained from individuals up to 50 years of age. Use of the thymus tissue will depend on whether it meets criteria for use as set forth in this specification.

The thymus tissue is aseptically processed and cultured under cGMP conditions to produce partially T cell-depleted thymus tissue slices.

The manufacture of cultured thymus tissue (CTT) consists of the following general steps: receipt and processing of incoming thymus tissue, slicing, culturing, media changes, dose calculation, packaging and transporting the thymus to the operating room. In addition, incoming thymus tissue is tested for acceptability and in-process and release testing is conducted on thymus tissue slices.

In an embodiment, the thymus tissue slicing process entails using sterile, single-use scissors and forceps to cut off a piece of thymus tissue. The operator removes the capsule of the thymus with forceps and scissors and places the capsule in the lid of the plate for disposal later.

The piece of thymus tissue is placed in the single-use tissue slicer using forceps. The top of the slicer (e.g., Stadie-Riggs hand microtome (Thomas Scientific, Swedesboro, NJ)), is placed onto the middle portion of the slicer and tightened in place. The operator runs the blade through the tissue piece to cut off a slice. The slices are approximately 0.5 to 1 mm thick. After cutting each slice, the top of the slicer is removed and the tissue slice is transferred onto pre-wetted sterilized Millipore® cellulose filters using forceps. The filters are pre-wetted with TOM. Approximately 50-90% of the filter space is filled without overlap of the tissue slices.

Typically, three in-process pieces are cut off of the tissue at the beginning of slicing, all of which are roughly 3×3 mm. One is sent for histology, and two are retained. Thymocytes flow freely into the medium as the thymus is sliced.

In an embodiment, the filter and thymus slices are transferred to a gelatin surgical sponge saturated with TOM in a tissue culture dish. Two filters are placed per sponge and 2 sponges are used per tissue culture dish. The process of slicing pieces of thymus is repeated until the required number of slices has been prepared. Culture dishes are labeled with an operation number, dish number, and ISBT barcode label. Completed dishes are placed in a humidified incubator at 37° C. with 5% $CO_2$.

The tissue engineered drug substance comprises thymus tissue slices after they have been placed in a culture dish in media and cultured for 12 to 21 day, as described below. The tissue-engineered drug product comprises the thymus tissue slices after transfer into a drug product container. No other processing is conducted to create the drug product from the drug substance; the only processing of drug substance to create drug product is transfer of slices into the leak proof container and corresponding media change.

The culturing of thymus tissue slices is more specifically set forth in the following paragraphs.

In an embodiment, thymus tissue is obtained from the operating room as discarded tissue from infants aged 9 months and under undergoing cardiac surgery. The tissue is then placed in a sterile specimen cup with a screw-cap top by the surgical team and transported to a GMP facility under ambient conditions for processing. The sterile specimen container in which the thymus is received is labeled, including a barcode, with the donor's name and medical record number. The donor screening group gives the thymus a unique identifier (thymuses are numbered consecutively) and a unique medical record number. For manufacturing, each tissue has an operation number, and a unique label. All identifiers are recorded on a "Confidential Thymus Donor Form" that is maintained separately from the batch record and kept confidential.

In an embodiment, the drug substance container closure system may be a cell culture dish with lid. One slice of thymus tissue is placed on a filter and two filters are placed on each gelatin sponge in thymus organ media in the dish. Four slices are placed in each culture dish and the dishes are stored in the incubator, with daily media changes, until ready for release.

In an embodiment, the culture dishes can be obtained from Corning. The dishes may be sterile, non-pyrogenic Falcon® 100 mm polystyrene cell culture dishes (product #353003). The dishes are cleaned by vacuum-gas plasma treatment and sterilized by gamma irradiation. The dimensions of the dish are 89.43 mm O.D.×19.18 mm.

In an exemplary embodiment, the Surgifoam® sponge (a water-insoluble, malleable, porcine gelati absorbable sponge) may be manufactured by Ethicon and it meets the requirements for Absorbable Gelatin Sponge, USP. A suitable sponge is a sterile, water-insoluble, malleable, porcine gelatin absorbable sponge that is intended for hemostatic use. An illustrative example of the mixed cellulose esters filter is manufactured by Millipore® (product #SMWP 02500). The 25 mm hydrophilic membrane has a 5.0 μm pore size. It is made of biologically inert mixtures of cellulose acetate and cellulose nitrate. The filter is sterilized by ethylene oxide prior to use.

After release and acceptance of the donor thymus into the processing laboratory, the thymus is cut into thin slices, which are placed on sterile filter papers that are put on the surgical sponges in sterile culture dishes. If the tissue is not processed immediately, it is stored in thymus organ media (TOM), as described below, at 2-8° C. for up to 24 hours after harvest from the donor before processing is initiated. TOM consists of Ham's F-12 culture media, HEPES buffer, L-glutamine and heat-inactivated fetal bovine serum (FBS).

In an embodiment, processing occurs in an ISO 5 space of a biological safety cabinet (BSC) in an ISO 7 manufacturing clean room. Only one lot of thymus tissue from a single thymus is processed in the BSC at any time. The BSC is cleaned before use. The thymus is tested for appearance by visual inspection and weighed. The thymus is then placed in a 150-mm tissue culture dish in TOM. The capsule of the thymus is removed with sterile, single-use forceps and scissors. Tissue pieces are taken for testing and as retained samples. The incoming thymus tissue is tested for identity by histology. Donor eligibility is also confirmed. Processing continues prior to receipt of histologic results and all donor screening results.

The acceptance criteria for donor screening is that all donor eligibility requirements must be met. Donor screening is required per 21 CFR 1271 to protect the safety of the thymus tissue transplant recipient. This screening minimizes the risk of disease transmission from donor to recipient.

Using sterile, single-use scissors and forceps, a piece of tissue is cut off. The piece of tissue is placed in the single-use tissue slicer using forceps. As previously described, the top of the slicer is placed onto the middle portion of the slicer and tightened in place. The operator runs the blade through the tissue piece to cut off a slice. The slices are approximately 0.5 to 1 mm thick. After cutting each slice, the top of the slicer is removed and the tissue slice is transferred onto pre-wetted sterilized Millipore® cellulose filters using forceps. The filters are pre-wetted with TOM. Approximately 50-90% of the filter space is filled without overlap of the tissue slices. The filter and thymus slices are transferred to a gelatin surgical sponge saturated with TOM in a tissue culture dish.

Thymus Organ Media (TOM)

The medium is made with ingredients approved for use in humans which are unlikely to cause allergic reactions, whenever such reagents are available.

All reagents must be tracked such that all ingredients can be identified after transplantation if any problems develop.

Fetal Bovine Serum (FBS) must be manufactured using US material because of the concern of Creutzfeldt-Jakob Disease. Information on each lot must be sent to the FDA prior to use.

Although normal adults have natural antibodies to FBS (antibodies to galactose-alpha-1, 3 galactose (Gal-α-1-3Gal)), which are tested for as IgM isohemagglutinins, immunodeficient children with DiGeorge syndrome do not have these antibodies 4.4. (Parker W, Yu P B, Holzknecht Z E, Lundberg K, Buckley R H, Platt J L., 1997, "Specificity and function of 'natural' antibodies in immunodeficient subjects: Clues to B cell lineage and development," *J Clin Immunol.* 17: 311-321).

Medium must be tested for bacterial, fungal, and mycoplasmal contamination prior to use.

In an embodiment, the following materials are used to prepare TOM:

HAMS F12 medium, Gibco™ #11765-054 (or case 11765-062), 500 ml bottles or equivalent source.

HEPES, Gibco™ #15630-080 or equivalent, 1M solution, 100 ml bottles. Final concentration 25 mM.

L-Glutamine, Gibco™ #25030-081 or equivalent source, (stock 200 mM).

Fetal Bovine Serum, Gibco™, #16140 (Heat Inactivated) or #10082-147 (heat inactivated, certified).

In an embodiment FBS that is HI may be used in the following manner:

FBS must be heat inactivated at 56° C. for 30 min.

To decrease the likelihood of contamination of the medium, medium must be divided into aliquots and no aliquot should be used more than once.

Aliquots of remaining FBS may be stored frozen (−20° C.) in 25 ml aliquots for research use.

In an embodiment, TOM may be prepared in the following manner.

Thaw fetal bovine serum overnight in the refrigerator, or at 37° C. with frequent gentle swirling.

If non-Heat inactivated fetal bovine serum is used, heat inactivate at 56° C. for 30 minutes.

Put all media components together into 4 liter flask if making 4 liters at a time, stir for 3-5 minutes with stir bar on magnetic stir plate on medium speed (no frothing).

Sterilize using the 0.2 micron filter units.

In an embodiment, sterilization of the TOM preparation may be performed in the following manner. Dispense 1 liter TOM into one liter flask. Measure 80 ml TOM in a disposable sterile cylinder. Pour the 80 ml TOM into a 150 ml Corning filter sterilization unit. Attach house vacuum to filter and filter sterilize per manufacturer's directions. Remove the filter unit from the container and discard. Cap the collection bottle with the sterile cap (provided with the unit). Label with TOM Lot No. Test one aliquot for bacterial culture with anaerobes; fungal culture, other; and *Mycoplasma* culture. Test one aliquot for endotoxin. Store all TOM aliquots in the −20° C. freezer upright.

TOM media may be released for use if: LAL result must equal to or less than 2 EU/ml for samples diluted 20 fold for testing or 1 EU/ml for samples diluted 10 fold for testing; all culture results must be negative for growth.

A BSC must be used for the filtering and dispensing the medium.

TOM is tested for sterility and endotoxin before release. TOM is not released for culturing a donor thymus until after the 14-day sterility testing acceptance criterion has been met. Once prepared, TOM is stored at −20° C. until thawed, at which point it may be stored for use in the refrigerator for up to two weeks.

In an embodiment, the 14-day sterility testing, may, for example, be conducted using the BacT/ALERT® culture system. The BacT/ALERT® (BioMerieux, Durham, NC) is a commercially available culture system that can be used to test samples using an automated microbial detection system.

All in-process and drug substance cultures are incubated for 14 days or reported immediately if the product becomes positive. For positive tests, the organism(s) are identified and their antibiotic sensitivities determined. Culture bottles containing medium for aerobic growth and bottles containing medium for anaerobic growth are inoculated with samples to be tested on day 1, day 7 and the day of release. All bottles are incubated for 14 days at 35-37° C.

FBS may be obtained from GIBCO™ brand, Life Technologies. The FBS is prepared by an aseptic, validated process. FBS meets USDA requirements for abattoir-sourced animals, traceability and country of origin. All fetal blood is collected from fetuses derived from healthy dams that have passed pre- and post-mortem certified veterinary inspection. All FBS are traceable by date and location of collection. FBS collected and processed in the United States is from USDA approved and inspected slaughter establishments. The United States is recognized by the USDA as being free of foot and mouth disease and rinderpest. To qualify the supplier, FBS is tested for pH, osmolality, endotoxin, total protein and identity before use Completed dishes are placed in a humidified incubator at 37° C. with 5% $CO_2$. Each lot of thymus tissue is stored in a separate incubator. After the thymus slices have been placed in the incubator, particle sampling and personnel monitoring is conducted.

Thymus slices are cultured for up to 21 days, and during culture the medium is changed daily. These thymus slices are considered the drug substance. During the culture period, many thymocytes are washed out of the thymus tissue slices or the thymocytes undergo apoptosis while preserving the thymic stroma. All manufacturing steps are conducted using sterile, disposable equipment and supplies. Media is aspirated by pipette from the culture dish and pooled into a sterile collection container for in-process testing. Ten (10) mL of fresh thymus organ media is then gently dispensed to each culture dish in a rinsing manner over the tissue slices. After the media change is completed, samples are taken from the pooled media for sterility and histology, if needed. Particle sampling and personnel monitoring are completed and line clearance is performed.

The medium is changed daily.

The slices are cultured for up to 21 days.

In-process testing is conducted to provide insight into the process and product quality and to help ensure the safety and quality of the final drug product.

In-Process Testing

Samples are collected for sterility in-process testing on day 1 and day 7. Samples are collected for *mycoplasma* in-process testing on day 7. Samples are collected for in-process histology testing between days 5 and 9. The dose is determined on the day prior to release. Gram stain, BacT, *mycoplasma* and endotoxin are tested on the day of release.

The Gram stain is a bacteriological laboratory technique used to differentiate bacterial species into two groups, Gram-positive and Gram-negative. Gram stain is tested on pooled spent culture medium from the culture dishes. The method uses a staining technique to determine the classification based on the physical properties of the cell wall. This method is used to make a preliminary morphologic identification or to establish whether there are significant numbers of bacteria in a clinical specimen. Staining is conducted either manually or using an automated stainer. It has been demonstrated that the two different staining methods showed no qualitative differences that would impact culture results.

Histology testing performed on days 5-9 includes: (1) determination that areas positive for keratin AE1/AE3 are scattered throughout tissue on days 5-9; (2) at least 1 Hassall body is microscopically identified; (3) CK14 staining of the tissue slices is scattered throughout the thymus tissue; and (4) intact nuclei are microscopically observed.

The presence of Hassall bodies and intact nuclei as well as successful CK14 staining are indicative of normal healthy thymus tissue that has been cultured.

Culture time is an important process parameter. As noted, culturing is performed for up to 21 days.

Testing of thymus samples at days 5, 9, 12 and 21 in culture is conducted to confirm whether histology results generated between days 5 and 9 in culture are representative of histology testing results generated between days 12 and 21 in culture. Based on the observations made by the pathologist for the samples discussed in the Examples, the histologic appearance of the tissue slices at day 5 reflects what is observed at each of the later time points (day 9, 12 and 21). This corroborates performing release testing between days 5 and 9.

Histologic examination of any one slice corroborates the conclusion regarding acceptability of the entire lot. The relevant characteristics of any one slice from a thymus reflect those of the entire thymus, supporting the continued use of a single slice of tissue for histology testing.

Figure 12A:
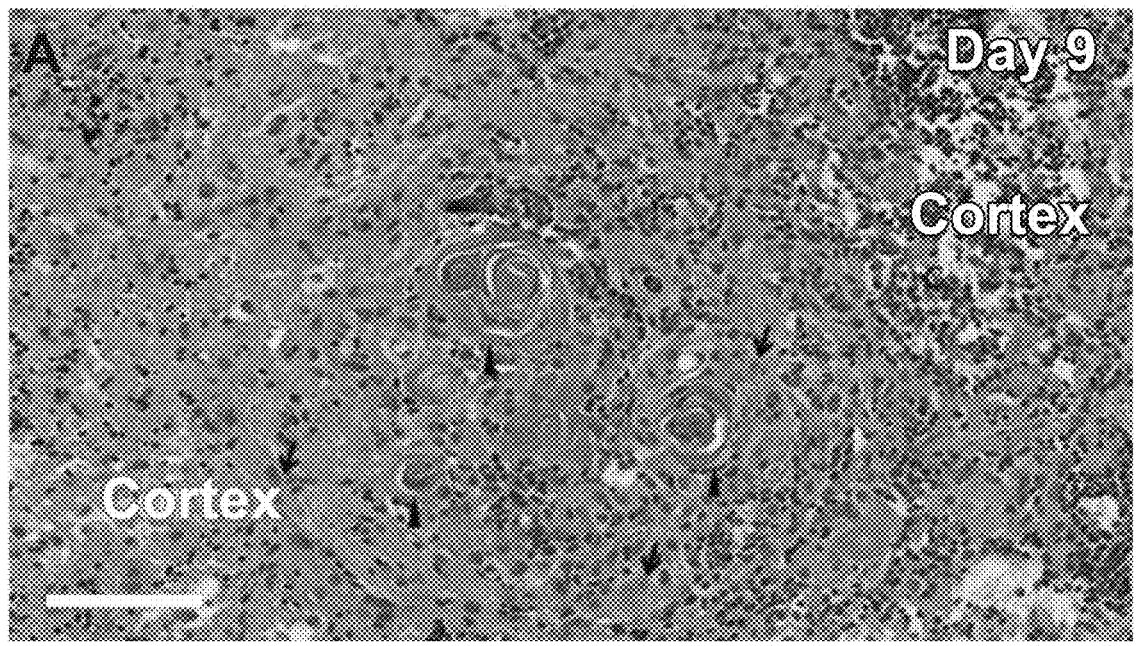
FIGS. 12A and 12B depict the histology of thymus tissue slides after exposure to forced degradation conditions of 10×PBS.
Figure 12B:
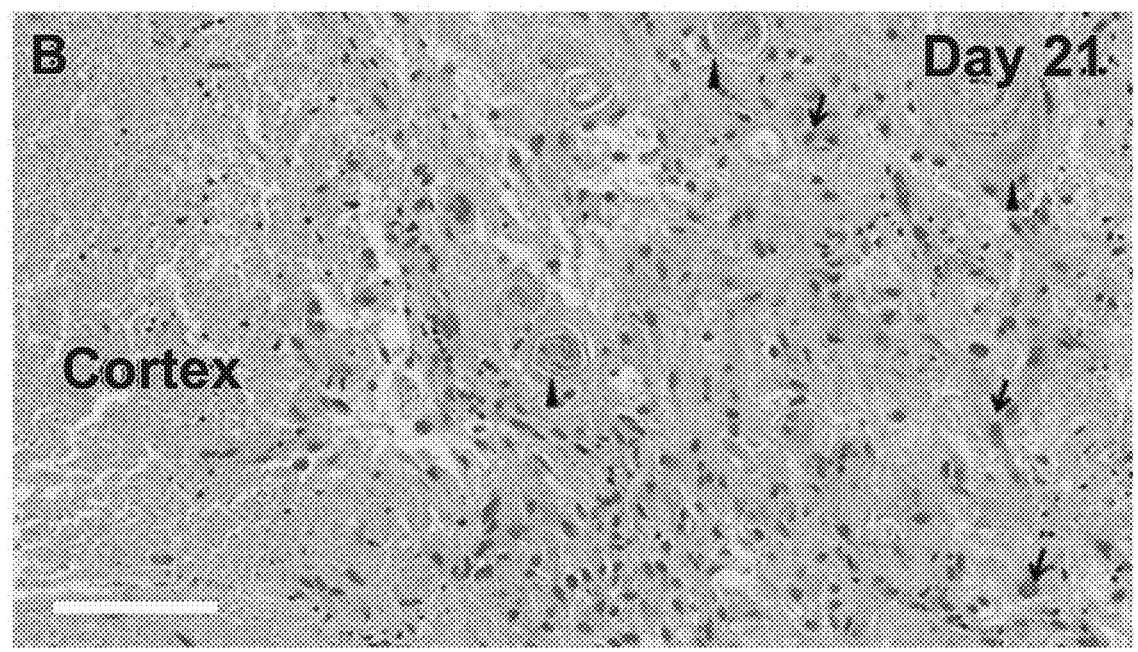
Figure 13:
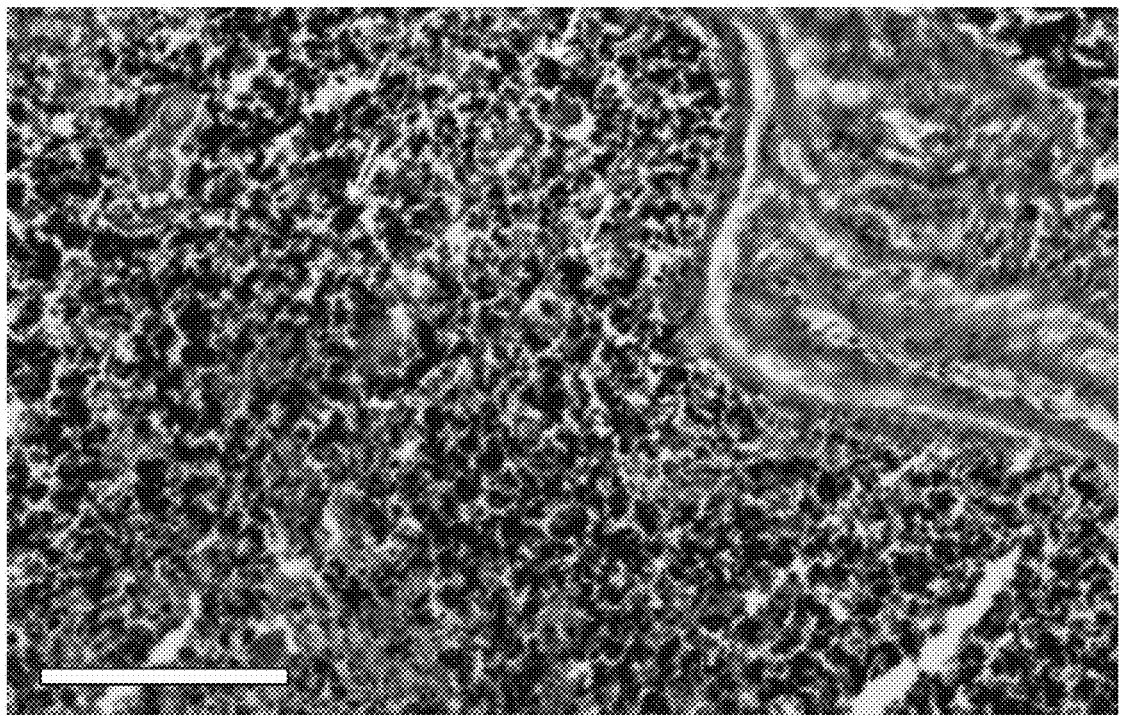
FIG. 13 depicts H&E stained histology sections for clinical sample MLM247. This is Day 0 of culture. The bar is 200 um. This is a frozen section from day 0. Because this was frozen, the tissue looks different from paraffin embedded formalin fixed tissue on day 0. Photo by Laura P. Hale, MD, PhD, Department of Pathology, Duke University.
Figure 14:
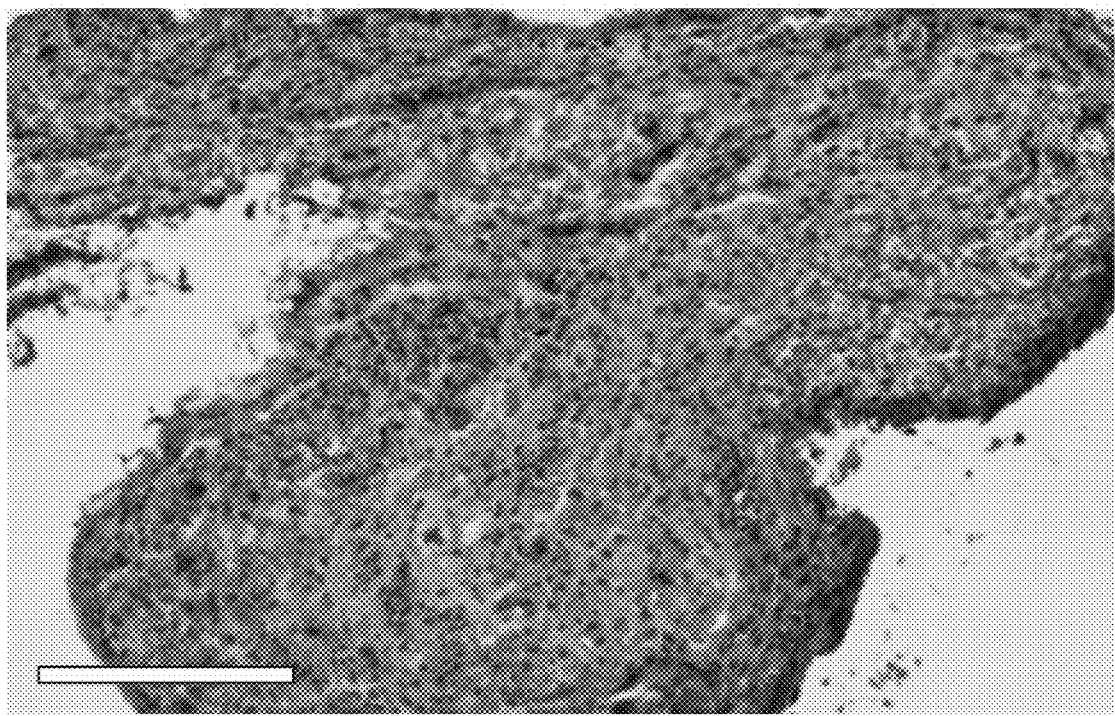
FIG. 14. Frozen section, H&E stained histology sections for clinical sample MLM219. This is a frozen section so the tissue looks different from paraffin embedded formalin fixed tissue that was cultured and presented above. Nevertheless, the important histologic characteristics of thymocyte depletion and robust viability of TEC are well represented. Photo by Laura P. Hale, MD, PhD, Department of Pathology, Duke University.

Forced degradation testing indicated as indicated in FIGS. 12A and 12B demonstrated that the cultured thymus tissue product is not easily degraded and is most sensitive to freeze/thaw as well as changes in osmolarity. Other conditions tested during forced degradation showed little to no effect on the cultured thymus tissue product.

Control of Cultured Thymus Product Drug Substance

Acceptance criteria for incoming thymus tissue product include the tests identified in Table 1 below.

TABLE 1

Incoming Thymus Tissue

Process Step: Incoming Thymus Tissue

| Attribute | Day of Test | Test Parameter | Acceptance Criteria |
| --- | --- | --- | --- |
| Safety | Day 0 | Donor Screening | Donor eligibility requirements are met per 21 CFR 1271 |
| Identity | Day 0 | Visual Inspection | Container intact Label accurate Pink to dark red, black marks may be present |
|  | Day 0 | Histology | >50% of areas positive for keratin in lacy staining pattern Hassall bodies identified CK14 staining in lacy pattern >90% intact nuclei observed in sections |
| Quality | Day 0 | Weight | ≥3 grams |

Abbreviations: CK, cytokeratin; EU, endotoxin unit; USP, United States Pharmacopeia. A thymus tissue is processed prior to obtaining all donor screening results.

Generally, the acceptance criterion for weight is greater than or equal to 3 grams. This is the minimal thymus weight that is accepted to ensure sufficient material is available for proper dosing of the final product. The acceptance criterion is based on experience in processing thymus tissue.

Acceptance criteria for in-process testing is identified in Table 2 below.

TABLE 2

In-process Testing:

Process Step: Drug Substance In-Process Testing

| Attribute | Day of Test | Test Parameter | Acceptance Criteria |
| --- | --- | --- | --- |
| Safety | Day 1 | Sterility | No growth |
| Safety | Day 7 | Sterility | No growth |
|  | Day 7 | Mycoplasma | Negative for the presence of mycoplasma |
| Potency | Days 5-9 | Histology | Areas positive for keratin AE1/AE3 scattered throughout tissue on days 5-9 At least 1 Hassall body identified CK14 staining scattered throughout tissue Intact nuclei observed |

Acceptance criteria for cultured thymus tissue drug substance testing is identified in Table 3 below.

TABLE 3

Cultured Thymus Tissue Drug Substance Testing

Process Step: Drug Substance Release Testing

| Attribute | Day of Test | Test Parameter | Acceptance Criteria |
| --- | --- | --- | --- |
| Appearance | Day of release | Visual inspection | No evidence of tampering or damage to containers Yellow to brown slices of tissue with varying thickness and shape |

TABLE 3-continued

Cultured Thymus Tissue Drug Substance Testing

Process Step: Drug Substance Release Testing

| Attribute | Day of Test | Test Parameter | Acceptance Criteria |
|---|---|---|---|
| Identity | Days 5-9 | Histology | Thymus tissue identity is confirmed by histology on day 1 and at midpoint (days 5-9). |
| | Day of release | Barcode | A barcode is used for tracking of the tissue throughout the processing and the barcode is confirmed at release. |
| Strength | Day before release | Dose | 1000-20,000 mm$^2$ of thymus tissue/recipient body surface area in m$^2$ |
| Safety | Day of release | Endotoxin (USP <85>) | <5 EU/kg body weight/hr |
| | Day of release | Sterility | No growth |
| | Day of release | Mycoplasma | Negative for the presence of mycoplasma |
| | Day of release | Gram stain | Negative |

The acceptance criterion for identity is that thymus tissue identity is confirmed by histology on day 1 and at the midpoint (days 5-9). A barcode is used for tracking of the tissue throughout the processing and the barcode is confirmed at release to verify the correct identity of the product.

Histology by Immunochemistry

The histology method is a standard method used by hospitals for all tissue types, as is known by a person of skill in the art.

Samples of the product are fixed in 1000 formalin and transported to the laboratory. Containers are labeled with a coded identifier instead of the patient's name to protect patient privacy, along a medical record number. Upon arrival in pathology, the specimens are assigned a unique pathology accession number, and barcoded. The subsequent blocks, slides, and paperwork are all barcoded with this pathology accession number.

After the specimen is received in the lab, the formalin-fixed tissue is grossly examined, and a written gross description of the material is prepared that will become part of the final report. The formalin-fixed tissue is then processed and embedded into a paraffin block by standard methodology on an automated processor. Sections are cut from the paraffin block and the following stains are performed by ASCP-certified histotechnologists:

Hematoxylin & eosin.
Cytokeratin AE1/AE3 immunohistochemistry.
Cytokeratin 14 immunohistochemistry.
CD3 immunohistochemistry.
Ki-67 immunohistochemistry.

During performance of the foregoing immunohistochemistry tests, appropriate control slides are also tested and reviewed. All control slides and internal controls demonstrate the expected immunoreactive patterns. The incoming thymus sample also serves as a control for tissue slices that have been in culture for 5-9 days, when samples are tested as part of potency testing. The incoming thymus sample appears as a typical thymus sample and then changes occur to the tissue slices while they are cultured and then tested after 5-9 days in culture. After 5-9 days in culture, the sample must show areas positive for keratin AE1/AE3 scattered throughout the tissue, the presence of at least one Hassall body, CK14 staining scattered throughout the tissue and presence of intact nuclei.

Slides are interpreted by a pathologist certified in Anatomic Pathology, with additional experience in the histologic evaluation of thymic tissue. The final report is issued by the pathologist and the report documents the results.

Acceptance criteria for cultured thymus tissue drug substance testing is identified in Table 4 below.

TABLE 4

Cultured Thymus Tissue Drug Substance Release Testing

Process Step: Drug Product Release Testing

| Identity | Day of release | Visual inspection | No evidence of tampering or damage to containers Yellow to brown slices of tissue with varying thickness and shape, adhered to round white filter paper |
|---|---|---|---|
| | Days 5-9 | Histology | Thymus tissue identity is confirmed by histology on day 1 and at midpoint (days 5-9). |
| | Day of release | Barcode | A barcode is used for tracking of the tissue throughout the processing and the barcode is confirmed at release. |

The cultured thymus tissue must be free of microorganisms. In the sterility test performed on day 1 and day 7, there should be no growth of microorganisms. *Mycoplasma* should be negative upon testing on day 7. The sterility test should be gram stain negative.

Product sterility is maintained using appropriate controls including aseptic technique; employing a training program and verifying the qualification of operators; utilizing appropriate clean room qualification procedures; employing establish clean media fill procedures and utilizing ready-to-use sterilized apparatus or apparatus sterilized utilizing validated sterilization cycles.

The containers of processed thymus tissue are visually examined for damage. Tissue slices normally exhibit a yellow to reddish brown appearance with varying thickness and shape.

Thymus tissue identity is confirmed by histology on day 1 and at midpoint (days 5-9).

A barcode is used for tracking of the tissue throughout the processing and the barcode is confirmed at release.

The dosage (area) is 1,000-20,000 mm$^2$ of thymus tissue/recipient body surface area in m2. Dose is controlled by the surface area of slices released to the operating room as appropriate for the patient's body surface area.

The acceptable dose range is defined as 1,000-20,000 mm$^2$ of thymus tissue per recipient body surface area (BSA) in m$^2$. The area of the thymus tissue is determined by photograph using software analysis (PAX-it Image Analysis Software). BSA is determined using the patient's height in cm and weight in kg. The DuBois and DuBois formula is used to calculate the BSA:

$$BSA = 0.007184 \times [\text{height (cm)}]^{0.725} \times [\text{weight (kg)}]^{0.425}.$$

The cultured thymus tissue is tested for endotoxin. The specification is ≤5 EU/kg body weight/hr.

Endotoxin testing may be performed, for example, by using the Endosafe PTS system. The cartridges used with the Endosafe PTS use a chromogenic kinetic Limulus Amebocyte Lysate (LAL) test. Each cartridge contains precise amounts of LAL reagent, chromogenic substrate and control standard endotoxin. Test sample is pipetted into four sample reservoirs. The instrument draws and mixes the sample with LAL reagent in two channels (sample channels) and with the LAL reagent and positive product control in the other two (spike channels). The sample is incubated then combined with the chromogenic substrate. After mixing, the optical density of the wells is measured and compared to a standard curve archived in the instrument. The instrument measures the reaction time in each channel. The archived standard curve specific for each batch of cartridges is constructed using the log of the reaction time versus the log of the endotoxin standard concentration. The sample and spike values are calculated by interpolation off the standard curve using the reaction time. This testing meets the requirements of United States Pharmacopeia (USP).

Testing for *mycoplasma* may be performed in the following manner. A sample of the pooled media is removed from the plates on day 7 and tested before product release.

In the event of a positive culture during manufacturing, the lot will be discarded and will not be administered. In the event of a positive culture after clinical product administration, the patient's attending physician and sponsor will treat the patient appropriately. A positive culture requires that the species of the contaminating organism be identified and its antibiotic sensitivity determined. The attending physician will institute antibiotic therapy for the thymus recipient, if indicated.

The drug product undergoes similar visual inspections and histology testing before use.

After the thymus tissue slices have been cultured for up to 21 days, the slices are transferred into drug product containers for transport to the operating room. Once received in the operating room, the slices are inserted into the thigh muscle of the recipient patient The container should be intact with no visible damage and the thymus tissue slices should appear as yellow to reddish-brown slices of tissue with varying thickness and shape. The tissue slices are visually examined to confirm that these acceptance criteria are met.

Cryopreservation and Thawing of Allogeneic Cultured Post-Natal Thymus Tissue Derived Product Cryopreservation of the allogeneic cultured post-natal thymus tissue derived product may be performed in the following manner.

A cryopreserved allogeneic cultured postnatal thymus tissue-derived product, prepared by method comprising the steps of:
 (a) obtaining suitable thymus tissue from a donor;
 (b) typing HLA alleles: HLA-A, HLA-B, HLA-C, HLA-DRB1, HLA-DQB1, HLA-DRB3, HLA-DRB4, HLA-DRB5, HLA-DQA1, HLA-DPB1, HLA-DPA1;
 (c) subjecting the thymus tissue to a conditioning regimen for a period up to 12 days; wherein the conditioning regimen for the donor thymus tissue comprises aseptically processing the donor thymus tissue in a thymus organ medium to produce partially T-cell depleted donor thymus tissue slices; further wherein the donor thymus tissue slices show, on days 5 to 9, areas positive for keratin AE1/AE3 scattered throughout the tissue, the presence of at least one Hassall body, CK14 staining scattered throughout the tissue and presence of intact nuclei upon completion of the conditioning regimen;
 (d) harvesting the partially T-cell depleted donor thymus tissue slices as allogeneic cultured postnatal thymus tissue-derived product;
 (e) cryopreserving the allogeneic cultured postnatal thymus tissue-derived product in liquid nitrogen; and
 (f) maintaining the cryopreserved allogeneic cultured postnatal thymus tissue-derived product in liquid nitrogen in a cryopreserved allogeneic cultured postnatal thymus tissue-derived product bank. In an embodiment, the cryopreserved allogeneic cultured postnatal thymus tissue-derived product of claim 66, wherein the thymus, on the day of harvest, demonstrates that >50% of areas are positive for keratin in a lacy staining pattern, that Hassall bodies are present, that CK14 stains in a lacy pattern, and that >90% of nuclei are intact.

In an embodiment, the donor thymus is sliced and divided into roughly two equal portions, putting each slice with its cellulose filter in a separate cryovial (Nunc tube). The filter is folded in half to insert it into the tube. About 1 to about 1.5 ml of freezing medium [sterile filtered 90% heat inactivated fetal bovine serum (FBS) and 10% dimethyl sulfoxide (DMSO)] at room temperature is added to cover the tissue. The sterile cap of the cryovial is replaced on the tube. Put all the tubes in a Biocision Cool Cell® (freezing container) or equivalent container which is at room temperature. Any empty slots in the CoolCell® should be filled with tubes that have 1 ml of freezing media. The tubes are placed overnight in a −80° C. freezer. Alternatively place each tissue plus filter in a 5 ml CryoELITE® tissue vial (Wheaton). Put 3 to 5 ml of freezing medium at room temperature to cover the tissue. Put in a Styrofoam™ (closed-cell extruded polystyrene foam) box and put in −80° freezer overnight. The vials are then transferred to the vapor phase of a liquid nitrogen freezer. Alternatively a controlled rate freezer can be used to bring the temperature of the cryovials to liquid nitrogen temperature.

To recover the tissue, remove the cryovial or the CryoELITE® tissue vial from the liquid nitrogen freezer. Thaw the thymic pieces in the vial rapidly with a swirling motion in a 37° C. water bath. The tube is sprayed with 70% ethanol and then is placed in the Biological Safety Cabinet (BSC). The thymic tissue and filter are removed from either the Nunc cryovial or the CryoELITE® tissue vial using forceps. The tissue and filter are placed in a 50 ml conical tube containing 20 ml of 4° C. TOM. Up to 5 filters can be placed in each 50 ml conical tube that contains 20 ml of 4° C. TOM. Immediately transfer the 5 filters with tissue to a fresh conical tube with 20 ml of 4° C. TOM media and put at 4° C. for 15 minutes. Repeat the wash 3 times. Keeping the tissue at 4° C., transfer each piece to its own 120 ml Starplex® container (polypropylene container) with 5 mls 4° TOM. All containers are brought to the surgical suite in a temperature-controlled container with a cold pack in it. The Starplex containers (polypropylene containers) with the tissue are brought into the operating room. The tissue on the filters are transferred to the sterile field into a tissue culture dish with approximately 2 ml of sterile saline. The scrub nurse removes the tissue from the filter paper by scrapping or pulling with forceps. The scrub nurse places the tissue, in an amorphous pile, back on the filter paper. The tissue culture dish with approximately 4 filters and the tissue is transferred to the operative site where the surgeon can easily access the tissue. The tissue is placed in the quadriceps muscles similarly to the procedure with CTT (RVT-802). The Cryo-CTT resembles the CTT in that it is partially T-cell depleted, the thymus tissue slices show areas positive for keratin AE1/AE3 scattered throughout the tissue, slices contain at least one Hassall body, CK14 staining is scattered throughout the tissue and presence of intact nuclei.

Transplantation of CTT

In an embodiment, unmatched thymus tissue slices from the donor are cultured for 12-21 days. On the day of the solid organ transplantation steroids are usually given at the induction of anesthesia. For heart or lung transplants, the thymus of the recipient is surgically removed at the time of the solid organ transplant. For other organ transplants the thymectomy may be done prior to the day of transplantation or on that day. The thymectomy method would be surgical, thoroscopic or robotic. At the end of the surgery after reperfusion, the recipient is given more steroids prior to receiving equine anti-thymocyte globulin (e.g., rabbit anti-thymocyte globulin) over 3 to 7 days to kill most of the residual T cells (and NK cells) in the recipient or alemtuzumab over 4 days to kill the T, B and NK cells. Administration of an immunosuppressant (such as cyclosporine or tacrolimus) and mycophenylate is then started until T cells develop and show greater than 10% naïve T cells. It may take 6 to 12 months for the naïve T cells to increase to this number. Cultured thymus tissue is processed for the thymus of the donor of the solid organ. Half of the CTT can be implanted into the quadricepts muscle between 12 and 21 days. The other half of the thymus will be cryopreserved for future use of the recipient. The immunosuppressive regimens will suppress any remaining T cells until naïve T cells are released by the cultured thymus tissue slices implanted in the recipient and the recipient meets criteria for weaning off the maintenance immunosuppression regimen. (Over 10% naïve T cells are needed to wean the immunosuppression.)

Thymectomy Protocol

The patient is taken to the operating room and is placed under general anesthesia by endotracheal tube.

The chest and abdomen are prepped and draped in a sterile fashion.

The patient undergoes a full sternotomy through a skin incision of approximately 4 cm.

Both pleural spaces are entered to guarantee a complete resection.

The phrenic nerves are visualized on both sides and care is taken to not compromise them.

The thymus is identified and carefully dissected away from the pleural investment of the lung, starting with the inferior horns and extending to the superior horns.

A complete thymectomy is performed.

Hemostasis is attained within the mediastinum.

Chest tube placement. One chest tube is always inserted (into the mediastinum). If a single pleural space is entered during the operation, the chest tube is continued from the mediastinum into that pleural space. If both pleural spaces are entered, a second chest tube is used in a similar fashion from the mediastinum to the other pleural space.

Drain size. #15 Blake® drains (tube for draining) are used for infants up to 2 years of age. #19 Blake® drains (tube for draining) are used for children 2 years and older.

Sternum closure: In neonates or infants, 0-Ti-Cron™ sutures (polyester sutures) are used to close the sternum. At about 1-2 year of age, #1 sternal wires are used. At about 2-5 years of age, #4 sternal wires are used.

The fascia, subcutaneous tissue and skin are closed with running absorbable suture.

A skin wound vac is placed on the sternum.

The patient is extubated in the operating room.

A sponge, instrument and needle counts are taken and must be correct at the end of the case.

Surgical Implantation of Allogeneic Cultured Postnatal Thymus Tissue-Derived Product.

Allogeneic cultured postnatal thymus tissue-derived product should be implanted in accordance with the following instructions. Implantation of thymus tissue into the thigh requires a healthy bed of muscle tissue.

Preparation for Implantation Procedure

The maximum and minimum dosage of planned transplanted allogeneic cultured postnatal thymus tissue-derived product should be calculated for each individual patient. Properly identify the intended recipient prior to administration.

Under sterile conditions within a laminar flow hood, the tissue slices on the filter papers that are on surgical sponges in medium are removed from the tissue culture dishes and placed in 120 ml sterile cups with 20 ml medium, packaged to maintain sterility, and delivered to the operating room or packaged for shipment. Tissue slices are not removed from the individual containers until ready to be used. Verify the product expiration date and time.

Always handle allogeneic cultured postnatal thymus tissue-derived product (tissue slices) using strict sterile technique. Inspect each container for leaks or evidence of damage. Do not use if there is evidence of contamination. Outside the sterile field, unpack allogeneic cultured postnatal thymus tissue-derived product containers from the shipping box. Remove racks containing polypropylene containers from the outer bag. When ready, a team member outside the sterile field, but adjacent to the sterile prep table, will open and remove the cap from each container, one at a time. Each open container is then held by the team member outside the sterile field extending his/her arm over the sterile field without touching the sterile field.

The sterile field team member will use a pair of forceps to remove the individual tissue slice with its filter paper from the container and place it in a sterile tissue culture dish containing approximately 2 ml preservative-free saline on the sterile prep table. Four tissue slices with the filter papers taken from four containers are placed in one sterile tissue culture dish that is on the sterile field in front of the sterile field team member. Using sterile forceps, the sterile field team member then peels the tissue slice away from the filter paper using two pairs of forceps, one of which holds the filter in place while the other pulls the tissue or scraps the tissue into a pile. The tissue removed from each filter paper is than put on that filter paper in a pile in the middle of the filter paper. The sterile tissue culture dish is then transferred to the sterile field. The next set of four allogeneic cultured postnatal thymus tissue-derived product containers will then be processed the same way while the surgeon is implanting the first 4 slices. When the surgeon finishes implanting the first four slices, the next dish with 4 pieces of tissue is put in the surgical field and the initial tissue culture dish is returned to the sterile field in front of the sterile field team member for loading the $3^{rd}$ set of four tissue slices. Continue this cycle until all the desired tissue is implanted. All of the tissue slices are not transferred at the beginning to avoid contamination from the air in the operating room.

Surgical Procedure

Step 1. Skin opening.

After induction of general anesthesia, make a vertical skin incision (typically ~5 cm in length) over one of the anterior thigh compartment. Note: The size of the incision and the use of one or both legs for the implantation procedure is determined by the size of the patient, planned amount of transplanted tissue, and his/her muscle mass. If all or most of the tissue can be implanted in one leg, then only one leg should be used.

Step 2. Open the fascia to expose the anterior compartment muscles.

Step 3. Muscle spreading and implantation.

Separate the muscle using a tonsil clamp or similar instrument along the natural furrows of the quadriceps muscle. The allogeneic cultured postnatal thymus tissue-derived product individual thymus slices should be implanted without cutting muscle tissue. Place individual tissue slices in "pockets" approximately 1 cm apart and approximately 1 cm in depth within the quadriceps muscle along the natural furrows. Depending on the size of the patient, the surgeon may place approximately 6-7 slices into 6 to 7 pockets along each furrow. Individual allogeneic cultured postnatal thymus tissue-derived product slices may be cut in half prior to implantation depending on the mass of tissue on each filter. A thick slice of tissue that had fully covered the filter paper should be cut in half for optimal vascularization of each tissue. Implant as much required tissue within each anterior compartment up to the maximum planned dose.

Step 4. Muscle closure.

Close the muscle with a single suture over the site where the thymus tissue was implanted to prevent muscle reopening and graft coming out of muscle. Ensure that the implanted tissue is entirely covered by muscle tissue with no exposed thymus tissue prior to closing the incision.

Step 5. Repeat Steps 3-4 for each allogeneic cultured postnatal thymus tissue-derived product tissue slice up to the maximum intended dose.

Step 6. Incision closing.

Confirm hemostasis. Close the skin incision with two layers of absorbable sutures and apply standard dressing such as wound closure strips or skin glue. Leave the fascia open to allow room for the muscle compartment swelling. An occlusive dressing may be used to prevent contamination.

Post-Operative Surgical Medical Management.

Use mild analgesics as needed. Monitor for signs of infection or dehiscence.

If the donor is a living related donor as for lung, kidney, intestine, or partial liver, a portion of that solid organ donors' thymus may be adequate for culture and implantation. The pathology criteria listed above for the day of harvest and for days 5 to 9 would need to be met.

Cryopreserved-cultured thymus tissue may be available from a 3$^{rd}$ party donor. However, the 3$^{rd}$ party donor must express all the recipient HLA alleles that are not expressed by the solid organ donor. This includes HLA-A, HLA-B, HLA-C, HLA-DRB1, HLA-DQB1, HLA-DQA1, HLA-DPB1, HLA-DPA1. Mismatching in HLA-DP alleles is acceptable if the mismatch is "permissive." In other alleles minor mismatching is allowed, e.g., HLA-A*01:02 into a recipient carrying HLA-A*01:01, in other words, the second field (after the colon) can be different, the first field (before the colon) must be identical.

Human Heart Transplant Procedures

Eligibility of a subject is determined based on a number of criteria including: Poor 12 to 24 month prognosis without cardiac transplantation despite current maximum supportive therapies; congenital or acquired heart disease with failure to thrive as defined by UNOS criteria; symptoms of advanced heart failure in the setting of congenital or acquired heart disease refractory to medical therapy; abnormal hemodynamics or increasing pulmonary vascular resistance; inoperable structural heart disease; symptomatic arrhythmias not amenable to medication or device therapy or poor exercise tolerance.

A number of absolute and relative contraindications to heart transplant surgery are assessed, including, for example, reversible renal dysfunction unless the subject is a candidate for heart/kidney transplant; irreversible liver disease unless candidate for heart/liver transplant; irreversible pulmonary dysfunction, use of non-conventional mechanical ventilator support (i.e. high frequency ventilator, maximal settings of CMV) or fixed pulmonary hypertension (TPG>15) unless the subject is a candidate for a heart-lung transplant; Diabetes mellitus with microvascular disease; or active, uncontrolled seizure disorder.

Other contraindications may include other diseases limiting long term survival and rehabilitation following a heart transplant; substance abuse, morbid obesity, malignancies; active psychiatric disorder; and other reasons such as documented medical non-compliance.

Relative contraindications include active infections; cognitive dysfunction; inadequate vascular access and significant allosensitization.

Donor and recipient histocompatibility management is also considered. Patients are evaluated for panel reactive antibodies ("PRA") for pre-formed HLA antibodies that the recipient may have formed in response to a "sensitizing event" such as prior transfusions or major surgeries using bypass/blood products or homograft materials.

An assessment is made of the recipient's presensitization history, for example, previous blood transfusions; number, dates; previous surgeries; previous pregnancies; immunization history and IVIG administration (with dates).

Patients with an excessively high HLA class I or class II PRA or those undergoing repeat transplant may be candidates for desensitization strategies. Specific strategies will be individualized to the potential recipient and may include use of plasmapheresis, IVIG, rituximab and/or bortezomib. Significant antibodies are those that remain present after a 1:16 dilution.

Pre-sensitized patients may require an actual prospective cross-match with potential donors. Patients with a history of HLA antibodies will undergo virtual cross-match in UNET at the time a transplant is being considered.

Pre-sensitized patients may require an actual prospective cross-match with potential donors via the following general guidelines. All patients with a history of HLA antibodies will undergo virtual cross-match in UNET at the time an offer is being considered.

If the cPRA <20%: virtual cross-match in UNET, no additional measures are needed; proceed with routine retrospective donor cross-match and routine immunosuppression.

If cPRA >20%: virtual cross-match in UNET, recipient receives plasmapheresis in the operating room ("OR") at the time of transplant.

If cPRA >70%: virtual cross-match, consider obtaining an actual prospective donor cross-match if time allows; administer plasmapheresis in the OR. Consider placement of a pheresis catheter in the OR for post-op continuation of pheresis.

Ongoing antibody reduction interventions are determined by donor cross-match, DSA's and clinical course.

For all pre-sensitized patients, blood will be sent for donor-specific antibodies within the first two weeks post-transplant and repeated as clinically indicated. Routine testing for DSA will be done on all post-transplant patients at least every 6 months post-transplant and as needed if any clinical concerns.

Standard blood product transfusion protocols are followed both pre- and post-transplantation.

Immunosuppression Management

Immunosuppression management is determined based on the solid organ to be transplanted.

Pediatric Heart Transplants

All patients will receive induction therapy with basiliximab or anti-thymocyte globulin based on their clinical situation and risk factors. The type of induction therapy used will be determined prior to transplant (first immunosuppression regimen drug therapy).

In an embodiment, pre-transplant/induction therapy typically comprises administration of:

Mycophenolate mofetil (CellCept®) 25 mg/kg IV prior to the operating room.

Methylprednisolone 10 mg/kg IV on induction (max dose 500 mg).

Methylprednisolone 10 mg/kg IV on release of x-clamp (max dose 500 mg).

ATG (antithymocyte globulin) 1.5 mg/kg IV on release of x-clamp.

Alternatively use basiliximab (Simulect®), dosed by weight of recipient.

<35 kg, 10 mg on release of x-clamp and 2nd dose 4 days later.

>35 kg, 20 mg on release of x-clamp and 2nd dose 4 days later.

In an embodiment pre-transplant induction immunosuppressive therapy for heart and CTT transplant candidates may comprise:

Basiliximab (Simulect®)—(if cannot give ATG).

Dosing:

<35 kg: Initial dose: 10 mg IV administered preoperatively by anesthesia on induction of anesthesia (after stable and methylprednisolone given).

Second dose: 10 mg IV administered 4 days after transplantation; hold second dose if complications occur (including severe hypersensitivity reactions or graft loss)

>35 kg: Initial dose: 20 mg IV administered preoperatively by anesthesia on induction of anesthesia when stable.

Second dose: 20 mg IV administered 4 days after transplantation; hold second dose if complications occur (including severe hypersensitivity reactions or graft loss.

Administration: IV infusion over 20-30 minutes. Half-life children 1-11 years: 9.5 days, adolescents 12-16 years: 9.1 days, adults: 7.2 days.

In an embodiment, anti-thymocyte globulin (ATG, rabbit derived, Thymoglobulin®), may be given according to the following dosing schedule for heart transplant subjects:

1.5 mg/kg/day for 3 to 7 days based on lymphocyte count and markers and platelet count. The first dose is given after organ reperfusion on release of cross-clamp after second dose of steroids (intra-operatively).

Continued daily based on above parameters, will be determined by transplant MD.

Administration: Slow IV infusion over 6 hours for first dose, subsequent doses can be given over 4 hours as tolerated.

In an embodiment, in addition to routine preoperative/intraoperative methylprednisolone for CPB/pump cases, patients may receive a dose of methylprednisolone (SoluMedrol®) 10 mg/kg (max dose 500 mg) IV to be administered by anesthesia on induction of anesthesia before basiliximab and then a second dose of 10 mg/kg (max 500 mg) on reperfusion (before ATG).

Post-Operative Maintenance Immunosuppression (Maintenance Immunosuppression Regimen)

In an embodiment, post-transplant immunosuppression comprises:

ATG (Thymoglobulin®) 1.5 mg/kg IV daily for 5-7 doses. Hold if WBC <2,000 or platelet count <50,000.

½ dose if WBC 2,000-3,000 or platelet count 50,000-75,000.

Mycophenolate 15-25 mg/kg IV/PO every 12 hrs.

Adjust for GI intolerance or leukopenia/neutropenia.

Can substitute azathioprine if GI intolerance.

Can substitute mycophenolic acid (Myfortic®) if GI intolerance.

Tacrolimus to start at 24-48 hrs after tx depending on renal function & oral tolerance.

Starting dose ~0.05 mg PO q 12 hrs & adjust based on levels.

~10-15 for first 6 months, 8-12 for 6 mo-3 years, 4-8 for >3 years.

Can substitute cyclosporine if IV medication needed or intolerance to tacrolimus.

Methylprednisolone 5 mg/kg IV q 8 hours×6 doses (max dose 125 mg).

Then, 1 mg/kg/dose IV/PO q 12 hours (max 30 mg/dose).

Wean over next 2-3 months based on biopsy results.

In an embodiment, tacrolimus (FK506, Prograf®) may be administered. Usual dosage forms include intravenous solutions of 0.5 mg/ml, and oral capsules of 0.5 mg, 1 mg, and 5 mg per capsule.

A starting dose of ~0.05 mg/kg/dose—is given every 12 hours (maximum 5 mg/dose) when the recipient is PO/NG/SL, usually started at ~24 hours post-operatively if renal function acceptable.

Tacrolimus trough levels are monitored daily until therapeutic dosing is achieved. Increase administration to every 8 hours, if necessary, to achieve therapeutic trough levels. If the drug is given sublingually, the capsule contents are sprinkled under tongue (may result in higher levels). Oral and sublingual doses are not. Generally it will be necessary to administer ½ of the oral dose to be given sublingually.

Tacrolimus dosing may be administered based on serum whole blood levels measured by mass spectrometry method 10-14 hours (7-9 hours if dosed every 8 hours) following the last dose.

Renal and hepatic function, adverse drug effects, infection and rejection history are all considered in managing a patient's tacrolimus levels. Dose adjustments do not need to be made if levels fall +/−1 within the desired range if the patient is clinically doing well. In these cases the decision is up to the attending transplant physician.

In an embodiment, cyclosporine is administered to patients unable to tolerate tacrolimus. The starting dose: 2 mg/kg/dose by mouth every 12 hours. If unable to achieve therapeutic levels (especially infants and young children) then the dosing frequency is increased to every 8 hours.

General dosing is based on the following serum whole blood levels measured by mass spectrometry method 10-14 hours (7-9 hours if dosed every 8 hours) following the last dose.

Renal and hepatic function, adverse drug effects, infection and rejection history are all considered in managing a patient's cyclosporine level. Dose adjustments do not need to be made if levels fall +/−10-20 within the desired range if the patient is clinically doing well. In these cases the decision is up to the transplant attending. Every effort should be made to document the patient's goal cyclosporine level in the chart. The IV dose is generally equal to ⅓ the oral dose.

In an embodiment, mycophenolate mofetil (Cellcept®) (200 mg/ml, 250 mg or 500 mg tabs) may be administered:

Begin 30-50 mg/kg/day in two divided doses (maximum dose children 2 g/day, adults 3 g/day).

IV dose=PO dose.

No therapeutic drug monitoring is required but can be done if concerns about toxicity.

Mycophenolate may cause bone marrow suppression and neutropenia.

The dose may be held when ANC <500 or WBC <1000; may need to decrease dose in setting of decreasing ANC (<1000) or WBC (<3000). In practice dosages of Cellcept® (mycophenolate mofetil) 500 mg=Myfortic (mycophenolate) 360 mg.

In an embodiment, mycophenolate (Myfortic® dosage forms 180 mg tablet, 360 mg tablet) may be administered in lieu of mycophenolate mofetil, according to the following dosage parameters:

Begin delayed-release tablet: 400 mg/m2/dose twice daily; maximum dose: 720 mg OR BSA 1.19-1.58 m2: 540 mg twice daily, BSA >1.58 m2: 720 mg twice daily.

No IV or suspension available. If IV or suspension is necessary then the drug is converted to Cellcept® (mycophenolate mofetil). (Cellcept® (mycophenolate mofetil) 500 mg=Myfortic (mycophenolate) 360 mg). Mycophenolate may cause the same bone marrow suppression as mycophenolate mofetil.

In an embodiment, if mycophenolate mofetil cannot be tolerated, azathioprine may be administered in the following manner:

Begin 2-4 mg/kg/day, given once daily

Azathioprine causes bone marrow suppression and dose may need to be reduced based on WBC/ANC. The IV dose equals the oral dose.

In an embodiment steroid may be administered, as methylprednisolone (Solu-Medrol®), prednisone or prednisolone.

Intravenous steroids are started intraoperatively (as induction immunosuppressive therapy), and the continued postoperatively at 5 mg/kg/dose (maximum 125 mg/dose) IV every 8 hours×6 doses.

Oral steroids may begin thereafter as prednisone tablets or prednisolone suspension 3 mg/ml. Intravenous methylprednisolone is continued if the transplant recipient is unable to tolerate the immunosuppression treatment regimen orally. A switch over to oral therapy may be made the recipient can tolerate oral medications. Exemplary dosing ranges of steroids are:

0-10 kg, start at 2 mg/kg/day divided BID, wean every 2 days, holding at 6 mg daily 0-30 kg, start at 2 mg/kg/day divided BID (max single dose of 30 mg, see below), wean by 5 mg/day every two days then hold at 10 mg daily.

>30 kg, 30 mg BID×4 doses, 25 mg BID×4 doses, 20 mg BID×4 doses, 15 mg BID×4 doses, 10 mg BID×4 doses, then start 15 mg daily to be further weaned by transplant cardiologist Continue to wean steroids to off over first month after transplant based on biopsy results. If rejection develops, then steroids will be restarted at the discretion of the transplant cardiologist and continued indefinitely based on further biopsy results and patient clinical status.

Other drugs in the second immunosuppression regimen include the following:

Sirolimus (Rapamune®) (0.5 mg, 1 mg, 2 mg caps): Initiated after diagnosis of coronary allograft vasculopathy or as otherwise clinically indicated by the transplant cardiologist.

Starting dose: 1 mg/m2 (maximum dose: 3 mg) once daily or divided into 2 daily doses if difficulty achieving adequate levels.

Therapeutic level goal is 4-8, accept lower tacrolimus level (same 4-8 range) if on both drugs.

Trough level drawn 23-25 hours following last dose or 11-13 hours following last dose if dosing every 12 hours.

Discontinue mycophenolate (Cellcept® (mycophenolate mofetil), Myfortic® (mycophenolate)), azathioprine when starting sirolimus.

Start Bactrim® (trimethoprim-sulfamethoxazole) prophylaxis: Can cause troublesome mouth sores, and delayed wound healing.

Pravastatin (Pravachol®)—used in teenagers/older children and those with CAV

Begin 0.2 mg/kg/day administered once daily (comes in tablet form, can give ¼, ½ or up to 1-2 tabs per day at night.

Titrate up dose as weight changes (maximum dose 20 mg/day).

Monitor LFT's, CK every 8 weeks.

Discontinue drug if joint or muscle pain develops.

Ganciclovir IV—given for CMV prevention if recipient or donor is CMV IgG positive.

Induction therapy: 5 mg/kg IV q 12 hours×7-14 days.

Maintenance therapy: 5 mg/kg IV daily.

Monitor WBC and renal function.

Transition to oral valganciclovir when tolerable.

Valganciclovir (Valcyte®)—for CMV prevention in all CMV+recipient or donor.

450 mg tabs or 50 mg/ml suspension.

4 months—16 years: total daily oral dose (mg)=[7×BSA× Cr Clearance].

>16 years: 900 mg orally daily.

Monitor CMV PCR at each visit.

Trimethoprim-sulfamethoxazole (Bactrim®, Septra®):

Single strength tablets 80 mg/400 mg, double strength tab 160 mg/800 mg, suspension 40 mg/200 mg per 5 ml.

Start when taking oral meals as well, prior to discharge for PCP/toxo prevention.

1 mo—12 yr: 5-10 mg/kg/day TMP div BID 3×/week on consecutive days.

>12 yr: 80-160 mg TMP orally daily or 160 mg TMP orally 3×/week.

Monitor for drugs which may increase or decrease tacrolimus and cyclosporine levels, as known to the person of ordinary skill in the art.

Also monitor for drugs having a synergistic nephrotoxicity with tacrolimus and cyclosporine.

Acute Transplant Rejection Treatment

In an embodiment, the subject is treated in the following manner in the event transplant rejection is noted.

In an embodiment, if the transplant recipient is grade 0, 1R without hemodynamic compromise: no treatment is required and consideration may be given to weaning steroids.

If the patient presents with grade 2R cellular rejection without hemodynamic compromise, the following treatment regimen is followed:

Optimize maintenance immunosuppression.

Administer methylprednisolone 15 mg/kg/day IV×3 days (maximum 1000 mg), can divide into every 12 hr dosing or give once every 24 hr.

Repeat biopsy in 1 to 2 weeks, for refractory cellular rejection repeat methylprednisolone and optionally Thymoglobulin® (anti-thymocyte globulin).

If rejection resolved then repeat biopsy 1 month later (6 weeks post-rejection) and resume previously defined biopsy protocol if rejection was successfully treated.

For refractory cellular rejection repeat methylprednisolone and consider Thymoglobulin® (anti-thymocyte globulin).

If the patient presents with grade 2R cellular rejection without hemodynamic compromise or higher grade rejection.

Optimize immunosuppression with higher levels (10-15).

Administer methylprednisolone 15 mg/kg/day IV×3 days (maximum 1000 mg).

Administer Thymoglobulin® (anti-thymocyte globulin).

Perform plasmapheresis if evidence of or concern for antibody mediated rejection.

If the patient presents with antibody-mediated rejection with or without hemodynamic compromise:

Administer methylprednisolone 15 mg/kg/day IV×3 days (maximum 1000 mg).

Perform plasmapheresis×5 runs (daily or every other day).

Administer IVIG 1-2 gm/kg IV monthly×6 months.

Evidence of graft dysfunction or hemodynamic compromise warrants a biopsy (when patient is stabilized) for cellular rejection and antibody-mediated rejection, including C4d staining. Start methylprednisolone (SoluMedrol®) while awaiting biopsy results, consider starting Thymoglobulin® (anti-thymocyte globulin) and plasmapheresis.

Treat grade 3R biopsies or hemodynamic compromise as a high-grade rejection episode.

Methylprednisolone (SoluMedrol®) 15 mg/kg/day IV×3 days (maximum 1000 mg). Consider inotrope therapy, Thymoglobulin® (anti-thymocyte globulin); and/or plasmapheresis.

Antibody-mediated rejection with or without hemodynamic compromise. Diagnosis: identification of C4d deposition in myocardial tissue with presence of donor-specific antibodies in peripheral serum sample. Consider steroids, ATG pheresis for AMR.

Kidney and Pancreas Immunosuppression Management

Exemplary induction immunosuppressive regimens and maintenance immunosuppressive regimens for kidney and pancreas transplantation procedures are presented below. In an embodiment, transplant recipients receive belatacept as maintenance therapy as part of the second immunosuppressive regimen. This protocol is typically employed when the recipient is Epstein Barr Virus (EBV) Ig+, exhibits no DSA (donor specific alloantibody); irrespective of absolute or calculated panel reactive antibodies (PRA), the transplant involves a negative cross-match and the recipient is <70 years old with a BMI of <35. Further considerations include the recipient's ability to tolerate induction (if they would not otherwise receive Thymoglobulin® (anti-thymocyte globulin)). The recipient should have no history of idiopathic focal segmental glomerulosclerosis (FSGS) and no previous non-kidney solid organ transplant. The protocol is for kidney transplants only.

In an embodiment, the induction immunosuppressive regimen comprises administration of methylprednisolone 500 mg intravenously intra-operatively. Alemtuzumab 30 mg is administered by intravenous infusion over a period of three hours (2 hours post administration of steroids). Belatacept 10 mg/kg is administered (TBW) (rounded to the nearest 12.5 mg) after the prior drug administrations.

In an embodiment, the maintenance immunosuppressive regimen comprises belatacept 10 mg/kg TBW on POD 4 and end of week 2, 4, 8, and 12; then 5 mg/kg every month (rounded to nearest 12.5 mg). Sirolimus is administered 2 mg daily with first trough level taken after 2 weeks (goal 8-10 ng/ml). No steroid maintenance therapy is normally required.

In an embodiment in low risk renal transplants where the recipient is not a candidate for belatacept, the induction immunosuppressive regimen may comprise no induction immunosuppressive regimen, i.e., the induction immunosuppressive regimen is optional. The maintenance immunosuppressive regimen may comprise mycophenolic acid 1000 mg administered every 12 hours and tacrolimus administered 0.1 mg/kg/day with a maximum of 5 mg every 12 hours.

In an embodiment when the recipient is high risk and ATG contraindicated, frail, an age >70 and who has evidence of recent infection and recent cancer activity, the induction immunosuppressive agent may comprise basalixiimab 20 mg to start in the operating room and post-operative day (POD) 4. The maintenance immunosuppressive regimen may comprise mycophenolic acid 1000 mg every 12 hours and tacrolimus 0.1 mg/kg/day with a maximum of 5 mg every 12 hours with tapering dosages of steroids.

In an embodiment involving high risk renal transplants or kidney and pancreas transplants the following parameters are considered. Recipients having a historic peak PRA>30, a historic donor specific antibody (DSA, irrespective of absolute or calculated PRA), 2nd transplant with early graft loss due to presumed immunological reason, 3rd or greater transplant, Pediatric en bloc (adult) recipients, kidney/pancreas, Pancreas alone and if high risk for DGF or high risk biopsy. In such a transplant, the induction immunosuppressive regimen (induction therapy) may comprise Thymoglobulin® (anti-thymocyte globulin) 1.5 mg/kg IBW (rounded to nearest 25 mg)×4 doses started in the operating room.

In an embodiment, where the recipient has zero PRA, no autoimmune diseases and a high BMI, the induction immunosuppressive regimen may comprise Thymoglobulin (anti-thymocyte globulin) 1.5 mg/kg IBW (rounded to nearest 25 mg)×4 doses started in the operating room. The second immunosuppressive regimen (maintenance therapy) may comprise tapering dosages of steroids, such as 500 mg in the OR, 240 mg POD 1, 125 mg POD 2, 125 mg POD 3, 90 mg POD 4, with mycophenolic acid 1000 mg every 12 hours starting POD 4 and tacrolimus 0.1 mg/kg/day with a maximum of 5 mg every 12 hours.

In an embodiment where a pancreas transplant is performed after a kidney transplant, the induction immunosuppressive regimen may comprise Thymoglobulin® (anti-thymocyte globulin) 1.5 mg/kg IBW (rounded to nearest 25 mg)×4 doses started in the operating room. The second immunosuppressive regimen may comprise a steroid taper to lowest of 5 mg daily, mycophenolic acid 1000 mg administered every 12 hours starting POD 4 and tacrolimus administered 0.8 mg/kg/day with a maximum of 4 mg every 12 hours.

For all immunosuppressive regimens involving administration of mycophenolic acid, the initial dose may be chosen based on an assessment of patient and transplant factors.

Adult Heart Transplant Immunosuppression Management

In an embodiment, induction immunosuppressive regimens are normally administered. Exceptions may occasionally be made when the risks of induction therapy are thought to outweigh the benefits of such therapy (i.e, the induction immunosuppressive regimen is optional).

In an embodiment, when an induction immunosuppressive regimen is administered, the regimen may comprise Simulect® (basiliximab): 20 mg IV given in the OR after reperfusion (cross-clamp removal) and repeated on post-operative day 4. In patients receiving induction immunosuppressive therapy, the calcineurin inhibitor (CNI) administered in the second immunosuppressive regiment should be initiated at 48 hours post-operatively, but may be delayed further depending upon the patient's renal condition. Steroids may be administered in the peri-operative period, typically methylprednisolone 500 mg intravenously at induction of general anesthesia and 500 mg IV before reperfusion (cross-clamp removal).

In an embodiment, the maintenance immunosuppressive regimen (post-operative maintenance immunosuppressive treatment), the regimen may comprise steroids, for example, methylprednisolone 125 mg IV q8 hours×3 doses (Start 8 hours after reperfusion) followed by prednisone: 0.5 mg/kg twice daily beginning post-operative day 2; decrease dose by 5 mg twice daily every 2 days to 10 mg twice daily (or 20 mg daily) and maintain this dose to 30 days post-transplant. The second immunosuppressive regimen may also comprise calcineurin inhibitors (CNI), for example, tacrolimus (FK506/Prograf®) (preferred agent): 1 mg by mouth every 12 hours. The dose is titrated to trough goal level of 10-15 ng/ml. Typical dose adjustments are made after 5 doses of the calcineurin inhibitor to establish steady state. Daily levels of the CNI are monitored initially to evaluate for CNI toxicity.

In an alternative embodiment cyclosporine/CyA (Neoral®) is administered at a dosage of 100 mg (1.5 to 5 mg/kg) by mouth every 12 hours. The dose is typically titrated to a trough goal level of 33 ng/ml. The maintenance immunosuppressive regimen may also comprise an antiproliferative agent such as mycophenolate mofetil (Cellcept®) 1,000 to 1,500 mg orally, with the dosage adjusted to maintain a WBC count >3,000. In the alternative, the antiproliferative agent may be mycophenolate (Myfortic®) 360 mg-720 mg administered orally twice a day, with the dosage adjusted to maintain a WBC count >3,000. In another embodiment, the antiproliferative agent is azathioprine (Imuran®) administered orally in a dosage of 2 mg/kg daily, with the dosage adjusted to maintain a WBC count >3,000.

In an embodiment, the maintenance immunosuppressive regimen may comprise sirolimus (Rapamune®) (TOR-I) administered orally at a dosage of 2 mg daily. The dosage is typically titrated to maintain a trough of 4-12 µg/ml.

In an embodiment, the maintenance immunosuppressive regimen may comprise a tapering dosage of steroids, for example, Month 1, decrease dose to 15.0 mg PO daily; Month 2, decrease dose to 12.5 mg PO daily; Month 3, decrease dose to 10.0 mg PO daily; Month 4, decrease dose to 7.5 mg PO daily; Month 5, decrease dose to 5.0 mg PO daily; Month 6, decrease dose to 2.5 mg PO daily. The steroid taper should be reevaluated following >ISHLT grade 1R with evidence of myocyte necrosis. The taper may be resumed after improvement in histological rejection guidelines.

In an embodiment, the maintenance immunosuppressive regimen may comprise the following additional/adjunctive agents: methotrexate (MTX) administered 2.5 to 5 mg twice weekly for cell-mediated rejection. MTX should be considered for 3 or more consecutive biopsies with >=grade 1R/2 or 2 consecutive biopsies with grade 2R/3A.

Adult Liver and Intestine Immunosuppressive Management

In an embodiment, a liver transplant with no renal dysfunction may be performed without any induction immunosuppressive regimen, i.e. such induction immunosuppressive regimen is optional. The maintenance immunosuppressive regimen may comprise, administration of mycophenolate 1 g every 12 hours and tacrolimus 2-3 mg every 12 hours along with a tapering dosage of steroids. A typical tapering dosage of steroids is: methylprednisolone 500 mg IV intra-operatively; methylprednisolone 250 mg IV 6 hours post-operatively once; methylprednisolone 180 mg IV once POD 1; methylprednisolone 90 mg IV once POD 2; methylprednisolone 60 mg IV once POD 3; methylprednisolone 30 mg IV once POD 4; prednisone 20 mg PO daily POD 5-14; decrease by 2.5 mg every 2 weeks. In an embodiment, the tapering dosage of prednisolone may be administered as 20 mg daily for the first 2 weeks; 17.5 mg daily for weeks 2-4; 15 m daily for weeks 4-6, 12.5 mg daily for weeks 6-8; 10 mg daily for weeks 8-10; 7.5 mg daily for weeks 10-12; 5 mg daily for weeks 12-14; 2.5 mg daily for weeks 14-16. Stop at 16 weeks. In certain circumstances the prednisolone is weaned to 5 mg daily and held for one year.

In an embodiment, a renal sparing liver transplant is performed where there is pre-operative dysfunction requiring HD or CVVHD/F. In another embodiment, a renal sparing liver transplant is performed where there is post-operative renal dysfunction with serum creatinine levels of >2 mg/dL on POD 0-1.

In an embodiment, the induction immunosuppressive regimen comprises Thymoglobulin® (anti-thymocyte globulin) 1.5 mg/kg (rounded to the nearest 25 mg) every 48 hours for 4 doses. In an embodiment, dosage reductions are made for pancytopenia or neutropenia. If WBC count is 2-3 or platelets are 30-50, give 12 dosage. If WBC is <2 or platelets are <30, hold the dosage.

In an embodiment, when premedication is indicated, the premedication may be administered 30-60 minutes prior to ATG infusion, acetaminophen 650 mg VT or orally, diphenhydramine 25-50 mg; and methylprednisolone 40 mg IV (or may use taper described above).

In an embodiment, the transplant is an intestine or multivisceral transplant such as a liver, intestine, pancreas transplant where the recipient is at high immunologic risk (PRA >0, prior pregnancy or transplant of isolated intestine, or where there is a low immunologic risk but a high risk of infection, the induction immunosuppressive regimen may comprise premedication, as described above, and may also comprise Thymoglobulin (anti-thymocyte globulin) 1.5 mg/kg (rounded to the nearest 25 mg every 24 hours for a total of 6 mg/kg, and basiliximab 20 mg in POD 0 and 4. The maintenance immunosuppressive regimen may comprise a tapering dosage of steroids as described above and mycophenolate 1 g every 12 hours and tacrolimus 1 mg SL every 12 hours (goal 12-16 mg/ml).

In certain embodiments, the tacrolimus is administered at a dosage to achieve target levels of 5-8 (liver) or 12-17 (intestine, liver-intestine) while patient is on mycophenolate mofetil (Cellcept®). The target may be altered if the patient is participating in a drug study trial, has rejection, renal compromise, or for advancing age.

In certain embodiments where mycophenolate mofetil (MMF, Cellcept®) is administered the standard dosage for adults is 1,000 mg every 12 hours. Dosage reductions may be made in patients with pancytopenia or neutropenia in accordance with the following: WBC 2-3 or platelets 30-50: consider giving 1%2 dose; for WBC <2 or platelets <30; consider holding dose.

In certain embodiments involving treatment of acute Liver allograft rejections, the following treatment may be administered: methylprednisolone 500 mg IV daily for 3 doses. If liver function tests are not improving, an additional two doses may be given (total of 5 doses of 500 mg IV daily), with a repeat lover biopsy performed on the eve of POD 3 or the morning of POD 4.

In certain embodiments, patients treated with SoluMedrol® (methylprednisolone) or Thymoglobulin® (anti-thymocyte globulin) whose CMV IgG was previously negative, should have a CMV IgG rechecked at the beginning of treatment.

Immunosuppressive Management in Lung Transplants

In certain embodiments, immunosuppressive management in lung implants follows the following induction and maintenance immunosuppressive regimens. Induction immunosuppressive regimens may follow an induction immunosuppressive regimen described previously. Maintenance immunosuppressive regimens may comprise the following:

Calcineurin Inhibitors: tacrolimus every 12 hours with dosing adjusted to maintain trough tacrolimus levels. See Table 5 below.

TABLE 5

Tacrolimus Trough Levels

| Time since transplant | Clinical factors | Target trough |
|---|---|---|
| 1$^{st}$ year | Young, high rejection risk, normal renal function | 12-15 ng/ml |
| 1$^{st}$ year | ≥65 yrs and/or CKD | 8-12 ng/ml |
| 1-3 years | Young, recurrent rejection, normal renal function | 10-14 ng/ml |
| 1-3 years | Stage 2-3 CKD | 8-10 ng/ml |
| 1-3 years | Stage 3-4 CKD | 6-8 ng/ml |
| >3 years | Stage 2-3 CKD | 6-8 ng/ml |
| >3 years | Stage 4 CKD | 6 ng/ml |
| Post Campath | | 8 ng/ml or lower, depending on renal function. |

Cyclosporine administered every 12 hours with dosing adjusted to maintain trough CyA levels according to Table 6 below.

TABLE 6

Cyclosporine Trough Levels

| Time since transplant | Clinical factors | Target trough |
|---|---|---|
| 1$^{st}$ year | Young, high rejection risk, normal renal function | 250-300 ng/ml |
| 1$^{st}$ year | ≥65 yrs and/or CKD | 150-200 ng/ml |
| 1-3 years | Young, recurrent rejection, normal renal function | 250-300 ng/ml |
| 1-3 years | Stage 2-3 CKD | 150-200 ng/ml |
| 1- 3 years | Stage 3-4 CKD | 100- 150 ng/ml |
| >3 years | Stage 2-3 CKD | 100-150 ng/ml |
| >3 years | Stage 4 CKD | 75-125 ng/ml |
| Post Campath | | 150 ng/ml or lower, depending on renal function. |

Steroid tapering dosage of 0-3 months post-transplant, 20 mg administered orally on a daily basis; 3-6 months post-transplant, 15 mg administered orally on a daily basis; 6-9 months post-transplant, 10 mg administered orally on a daily basis; and >9 months post-transplant, 5 mg administered orally on a daily basis.

Azathioprine 2 mg/kg may be administered orally on a daily basis. Important to ensure normal TMIPT enzyme levels prior to start and to follow LFTs/CBC. Dosage adjustments may be considered if leukopenia is observed.

Mycophenolate mofetil (Cellcept®) may be administered at a usual dosage of 1,000 mg twice daily. The usual dosage for heart and lung transplants is 1,500 mg daily administered orally. CBC should be followed and dosage adjustments should be considered if leukopenia is observed.

Sirolimus is generally contraindicated in the first 3 months following transplantation due to concerns for anastomoctic dehiscence. If administered, sirolimus is typically administered 1 mg daily by oral administration, which is adjusted based on trough levels. For example, administered as a 3$^{rd}$ agent or for CNI sparing, a target trough is 4-8 ng/ml; and as a CNI alternative, the trough level is 10-15 ng/ml.

EXAMPLES

Example 1: Intra-Thymus Variability Study

Intra-thymus variability was studied to determine whether histology testing results from one part of a thymus could be considered representative of histology testing results in any other part of the same thymus. The results of this test were used to determine how many samples should be tested during both routine release testing and for process validation testing.

Histology acceptance criteria were established, as noted previously, including the assessment of: areas positive for keratin AE1/AE3 scattered throughout tissue on days 5-9; at least 1 Hassall body identified; CK14 staining scattered throughout tissue; and intact nuclei observed.

Figure 5A:
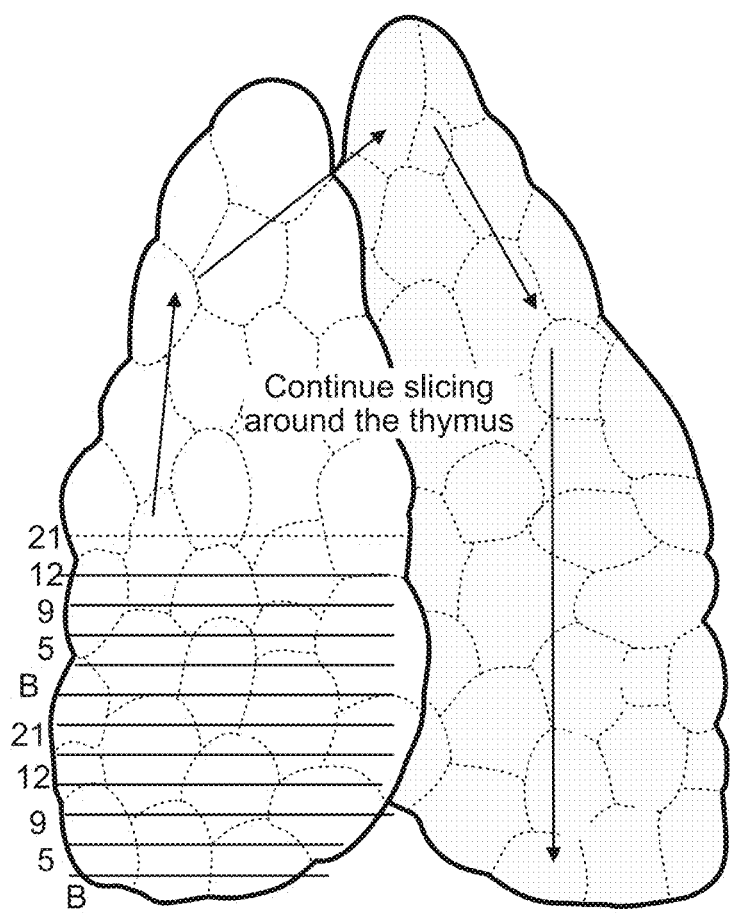
FIG. 5A shows a schematic showing the slicing of thymus tissue for characterization testing, as discussed in section [00520].
Figure 5B:
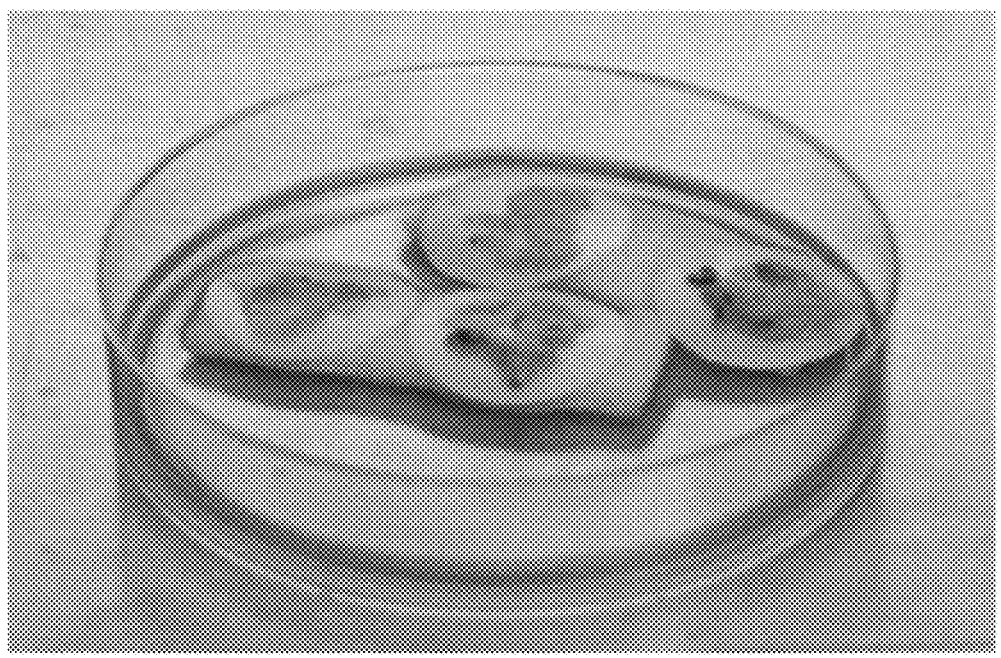
FIG. 5B is a figure showing slices of thymus tissue on cellulose filters on surgical sponges in a tissue culture dish as is used for culture of the thymus.
Figure 6A:
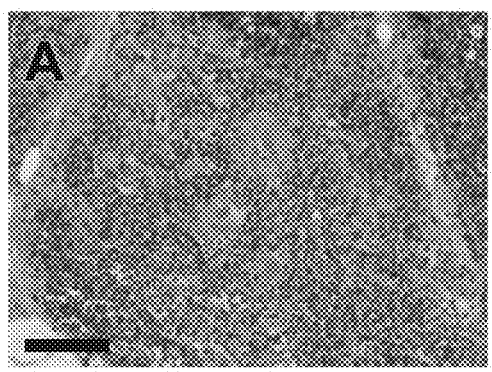
FIGS. 6A-H depict histology testing of thymus tissue slices from a lot (MFG-056) of cultured thymus tissue on day 5, 9, 12 and 21 after harvest of the thymus from a donor. Hematoxylin and eosin-stained slices (left panels) and their corresponding reactivity with a cocktail of the anti-cytokeratin antibodies AE1/AE3 (right panels; brown color denotes positive reactivity) are shown at day 5 (FIG. 6A, FIG. 6B), day 9 (FIG. 6C, FIG. 6D), day 12 (FIG. 6E, FIG. 6F), and day 21 (FIG. 6G, FIG. 6H), respectively. Bars in the lower left of each panel represent 100 μm. Panels with H&E show progression depletion of T cells with time.
Figure 6B:
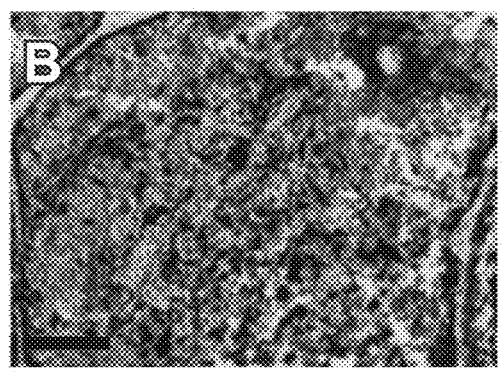
Figure 6C:
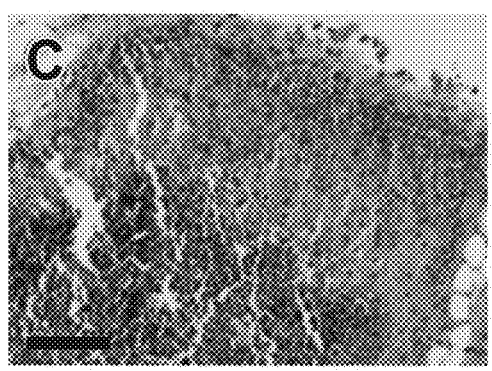
Figure 6D:
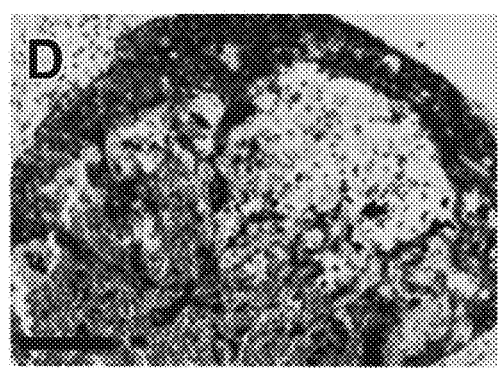
Figure 6E:
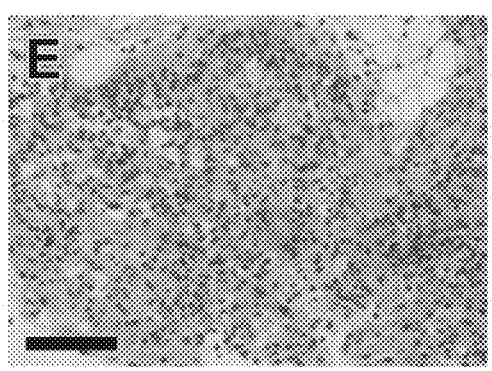
Figure 6F:
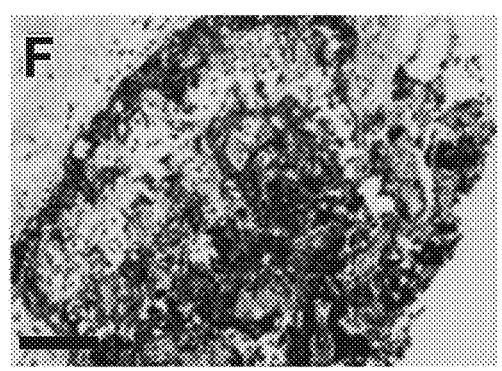
Figure 6G:
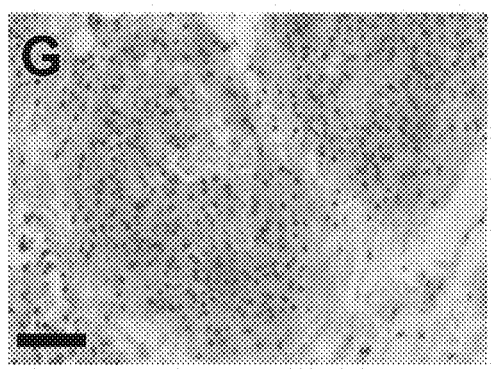
Figure 6H:
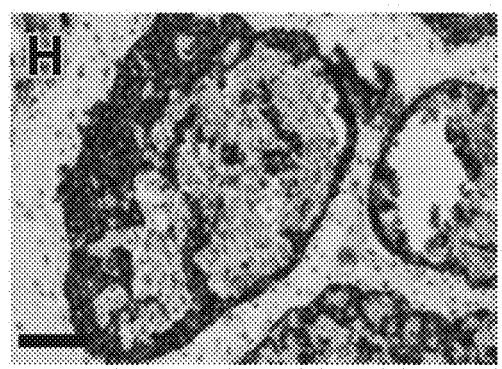

For this study, three thymuses were sliced in a directional manner and the location of the slices within each thymus was tracked. Slices were cultured in 6-well plates to allow tracking of each slice. Slicing was conducted as shown in FIG. 5A.

For each thymus in the study, slices were dedicated for analysis at each of the following time points, baseline (day 0), day 5, day 9, day 12 and day 21.

Between 5-11 slices were cultured at each time point for each thymus. Slices were cultured per the methods described above with daily media changes. Slices were submitted for H&E staining in the pathology lab and analyzed for identity, potency and viability. All slices in this study met the release acceptance criteria for histology testing as designated above, namely: areas positive for keratin AE1/AE3 scattered throughout tissue on days 5-9; at least 1 Hassall body identified; CK14 staining scattered throughout tissue; and intact nuclei observed.

In addition to assessment of whether each slice met the release acceptance criteria, a more detailed review of each H&E and AE1/AE3 slide was made by the pathologist. Images of some of these slides for cultured thymus tissue lot MFG-056 are shown in FIGS. 6A-H. The following observations were noted.

All slices derived from the same donor thymus met the acceptance criteria at each time point. In different slices, areas of cortex resemble each other and areas of medulla resemble each other. However, variations were observed in the relative proportion of cortex and medulla between slices.

The differences observed between different slices derived from the same thymus as a function of culture time were primarily related to the amount of necrosis, primarily of thymocytes (which increased as culture time increased) and the numbers of residual thymocytes (which decreased as culture time increased).

Based on these observations, any one slice from a thymus was representative of the entire thymus. In addition, the histologic appearance of the tissue slices at day 5 reflects what is observed at each of the later time points (day 9, 12 and 21).

Example 2: Whole Thymus Time-Course Study

Figure 7A:
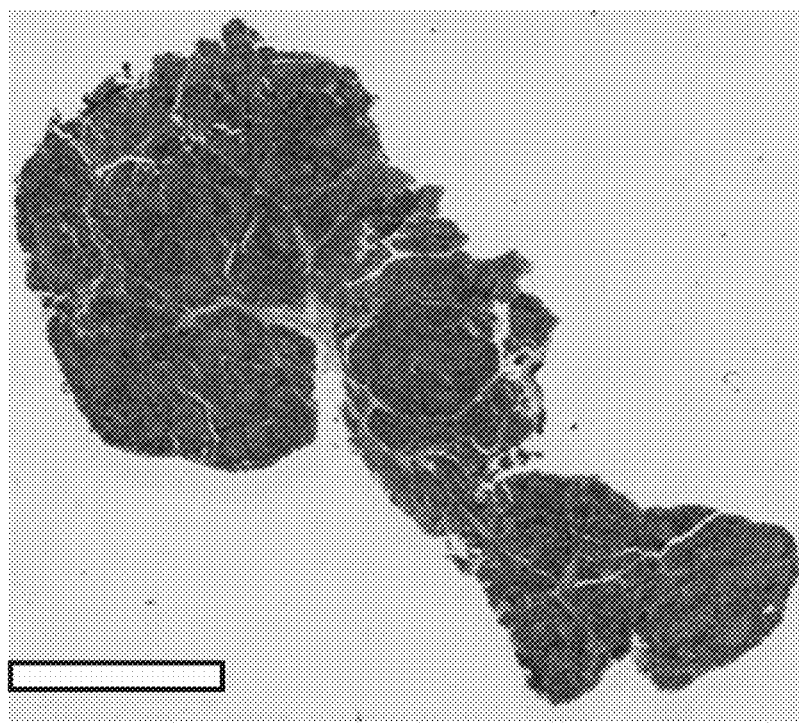
FIGS. 7A and 7B depict the histology of thymus tissue slices on day 0 of the time course in a scale of 5 mm (FIG. 9A) and 100 μm (FIG. 7B), respectively. This shows the thymus and thymocytes at low power (bar 5 mm) and high power (bar 100 um) on day 0. This is normal thymus. At this time the cortex and medulla both have large numbers of thymocytes with dark blue nuclei contributing to the overall dark blue appearance of the tissue. Photo by Laura P. Hale, MD, PhD, Department of Pathology, Duke University.
Figure 7B:
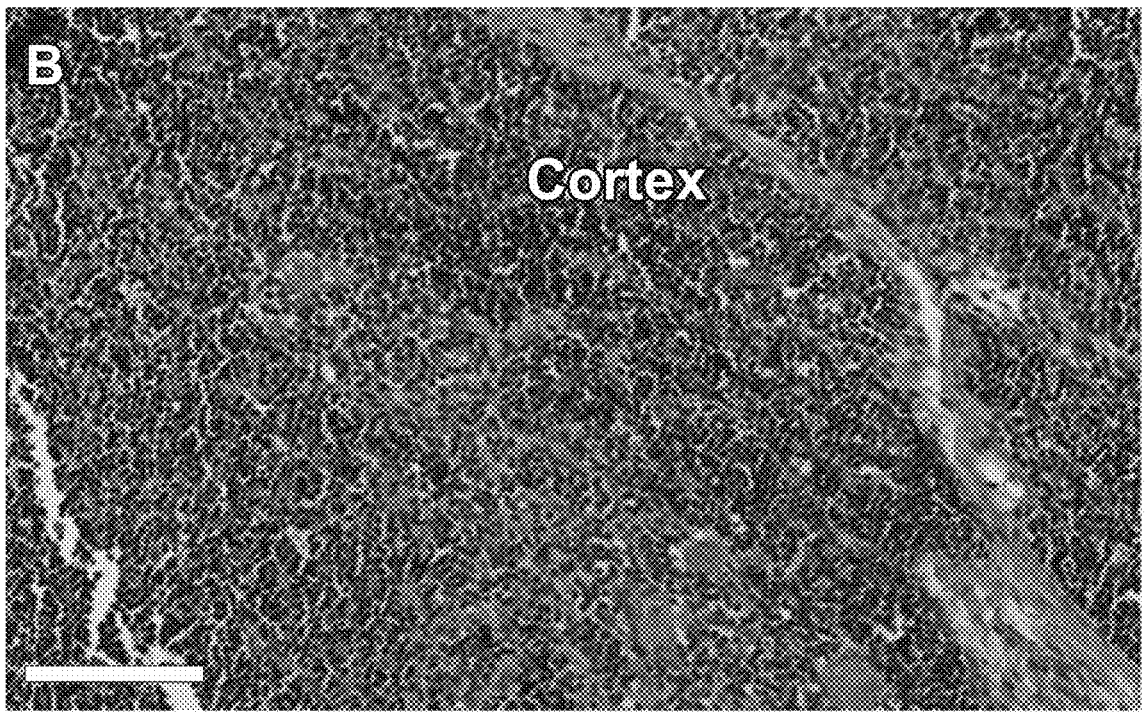
Figure 8A:
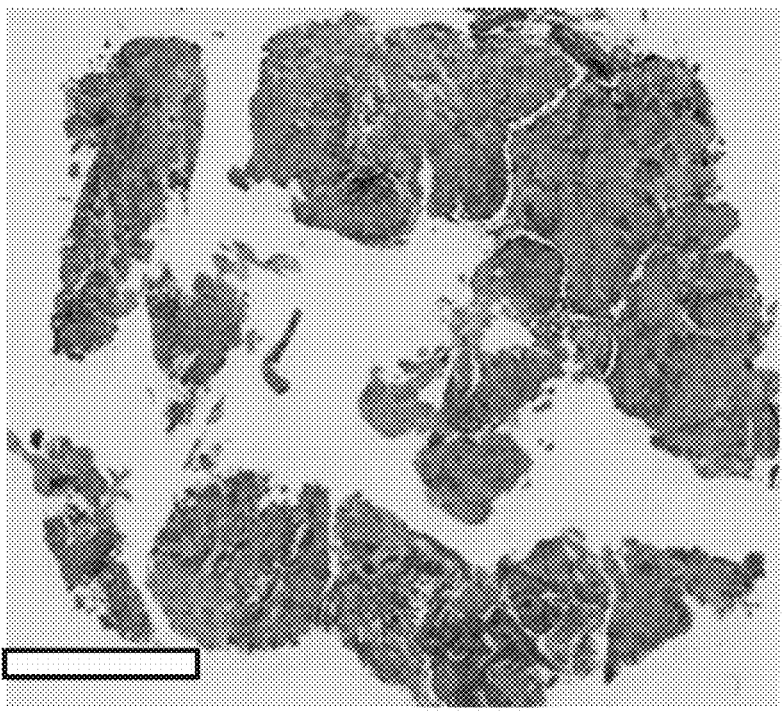
FIGS. 8A and 8B are images from H&E stained slide that depict the histology of thymus tissue slices on day 5 of the time course in a scale of 5 mm (FIG. 8A) and 100 μm (FIG. 8B), respectively. Progression of depletion of the thymocytes results in a more eosinophil (pink) appearance of the tissue. Photo by Laura P. Hale, MD, PhD, Department of Pathology, Duke University.
Figure 8B:
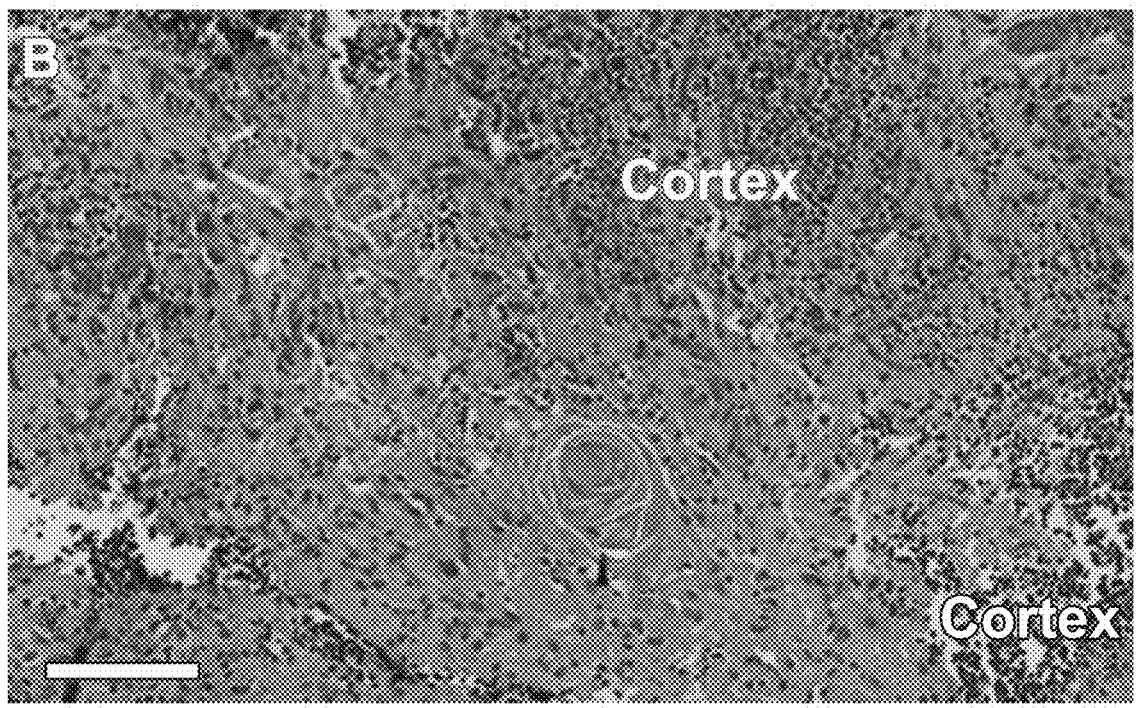
Figure 9A:
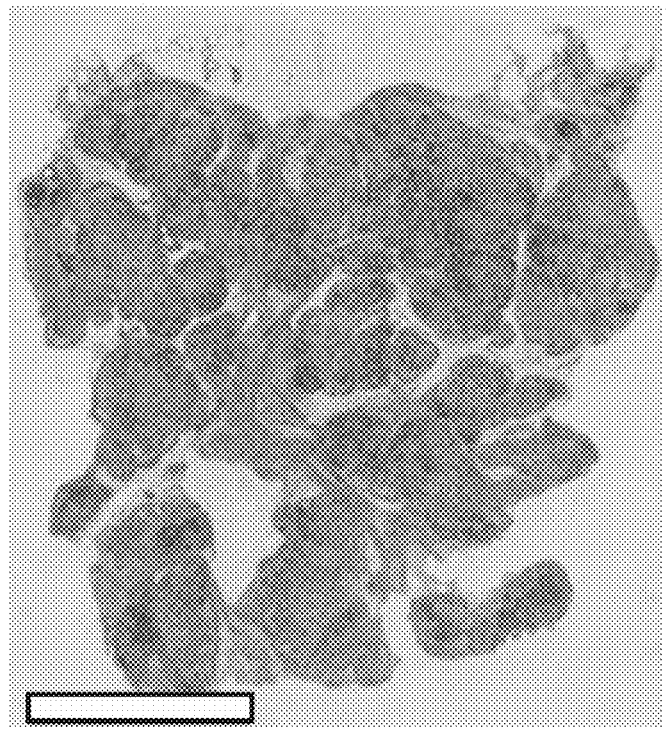
FIG. 9A and FIG. 9B depict H&E staining of the thymus tissue slices on day 12 of the time course in a scale of 5 mm (FIG. 9A) and 100 μm (FIG. 9B), respectively. We see progressive depletion of thymocytes. The higher magnification shows numerous eosinophilic cell bodies lacking nuclei which are diagnostic of necrotic cells that have undergone karyolysis (dissolution of the nuclei). This degree of necrosis is expected at this time in culture. Photo by Laura P. Hale, MD, PhD, Department of Pathology, Duke University.
Figure 9B:
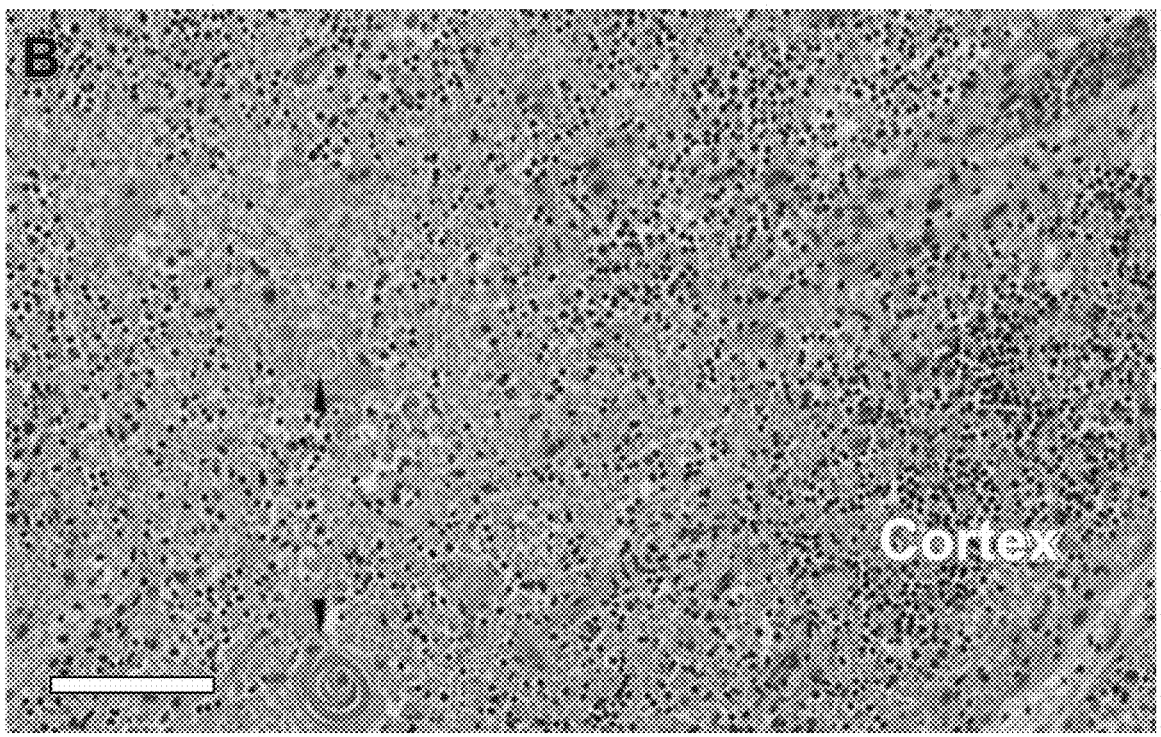

For this study, five thymuses were sliced and cultured per SOP. On the day of slicing, the first, middle and last slices were prepared for immunohistochemistry. The remainder of each thymus was sliced and cultured in 6-well plates. Each thymus was designated for one of the following time points: baseline (day 0), day 5, day 9, day 12 and day 21. See FIG. 7 for a day 0 thymus slice, FIG. 8 for a day 5 slice, FIG. 9 for a day 12 slice, and FIG. 10 for a day 21 slice.

The total number of slices from each thymus ranged from 21 to 62 slices. Slices were cultured per the procedures outlined above with daily media changes. Slices were submitted for H&E staining in the pathology lab and analyzed for identity, potency and viability. All slices in this study met the release acceptance criteria for histology testing, namely: areas positive for keratin AE1/AE3 scattered throughout tissue on days 5-9; at least 1 Hassall body identified; CK14 staining scattered throughout tissue; and intact nuclei observed.

In addition to assessment of whether each slice met the release acceptance criteria, a more detailed review of each H&E and AE1/AE3 slide was made by the pathologist. The following observations were noted.

All slices derived from the same donor thymus and tested at the same time point similarly met the acceptance criteria for that time point with variations in the relative amounts of cortex and medulla, residual thymocytes and/or necrosis, as described above.

Differences noted were the relative size, shape, relative content of thymus cortex versus medulla, amount of necrosis, condensation of the thymus epithelium and numbers of residual thymocytes.

In addition, lots from different donors tested at different time points were also qualitatively similar to each other. Differences observed were related to the amount of necrosis (which increased as culture time increased) and numbers of residual thymocytes (which decreased as culture time increased).

Histologic examination of any one slice resulted in the same conclusion regarding acceptability of the entire lot. Based on these observations, the relevant characteristics of any one slice from a thymus reflect those of the entire thymus. In addition, the histologic appearance of the tissue slices at day 5 reflects what is observed at each of the later time points (day 9, 12 and 21), although more necrosis is observed at later time points. FIG. 11 is a good example showing the similarity of the epithelial network as assessed by antibody AE1/AE3 from day 0 to day 21.

Example 3: Thymus Tissue Forced Degradation Study

In this study, thymus tissue slices were treated to generate tissue slices that were considered degraded or non-viable. Three thymuses were used for these experiments. Control samples were taken from each thymus. The treatment conditions presented in Table 7 were tested.

TABLE 7

Forced Degradation Treatment Conditions

| Condition | Duration of Treatment |
|---|---|
| Control | No treatment |
| Heat Shock, 55° C. | 4 hours |
| Freeze/thaw, −20° C./ambient | 4 hours |
| Room Temperature, 20-24° C. (Culture in BSC) | 24 hours |
| Dehydration (Culture in absence of media) | 24 hours |
|  | 48 hours |
| Nutritional Depletion, (Culture in Normal Saline) | 24 hours |
|  | 48 hours |
| Osmolarity Change, (Culture in 10X PBS) | 24 hours |
| DMSO Exposure, (Culture in 1% DMSO in TOM) | 24 hours |

Heat shock was accomplished by placing the 10 cm culture dish containing the slices into a Ziploc® bag (a re-sealable sliding channel storage bag), and placing into a 55° C. water bath. The plate rested on a support and was not submerged. Freeze/thaw was accomplished by placing the 10 cm culture dish into a −20° C. freezer for 4 hours followed by thawing at ambient.

Samples were tested for histology on days 5 and 9 in culture. Some samples were also tested on day 21. All slices in this study met the release acceptance criteria for histology testing namely: areas positive for keratin AE1/AE3 scattered throughout tissue on days 5-9; at least 1 Hassall body identified; CK14 staining scattered throughout tissue; and intact nuclei observed.

In addition to assessment of whether each slice met the release acceptance criteria, a more detailed review of each slide was made by the pathologist. The following observations were noted.

Samples exposed to freeze/thaw or to 10×PBS showed the most necrosis but some cells still appeared intact and met the histologic criteria for viability. See FIG. 12 for an example of exposure to 10×PBS.

Slices that were held at room temperature, dehydrated, incubated in normal saline or 1% DMSO or underwent heat shock showed a lesser degree of histologic changes.

For control samples, the following observations were noted by the pathologist.

Thymocytes are progressively lost as thymus tissue is cultured. However, dead cells may persist in cultured thymus long-term due to inability to recruit phagocytes to clear them. The nuclei of cells undergoing apoptotic cell death initially condense and stain more darkly (blue) with hematoxylin dye. As these cells deplete their energy but are not phagocytosed, they lose their membrane integrity and become necrotic. Karyolysis (dissolution of nuclei in necrotic cells) typically occurs within 2-3 days in vivo, but appears to occur more slowly during thymus culture. Thus, it is not unusual to see large eosinophilic (pink) expanses of necrotic cell debris where thymocyte nuclei have undergone karyolysis. Some dead thymocytes retain their nuclei, which have ragged edges and altered staining characteristics compared to those of viable cells.

As thymocytes are depleted from the tissue, the thymic epithelial cells become more visible. The three-dimensional thymic epithelial (TE) network is normally demonstrated in sections via a light and lacy arrangement of connected epithelial cells and/or (seemingly) scattered TE cells whose connections are not evident in the section being examined. As thymocytes are lost during culture, the three-dimensional network contracts. This results in condensation of the residual epithelium, such that the subcapsular cortical epithelial layer becomes thicker and medullary TE cells become more tightly packed. The nuclei of viable TE cells are typically oval, larger than those of thymocytes, and have a sharply defined nuclear membrane outlined by the hematoxylin (blue) stain, as well as one or more nucleoli. These TE nuclei typically look "open", meaning they do not stain darkly with hematoxylin. This fits with an interpretation that they are alive and metabolically active, since active chromatin ("euchromatin") cannot bind the hematoxylin dye. The presence of nucleoli, which are the sites of ribosome synthesis, in many TE cells further confirms that they are alive and metabolically active. The typical histologic appearance of control sections from days 5, 12 and 21 is shown FIGS. 8, 9 and 10, respectively.

For the treatment conditions including room temperature, dehydration, 1% DMSO and heat shock the pathologist indicated that the appearance of the slices did not differ significantly from those of the control. For the heat shocked sample, the pathologist noted that the heat treatment may have "fixed" the cells, by coagulating proteins that prevent further degradation. Heat treatment has been used as a fixative for tissues, including thymus.

Figure 10A:
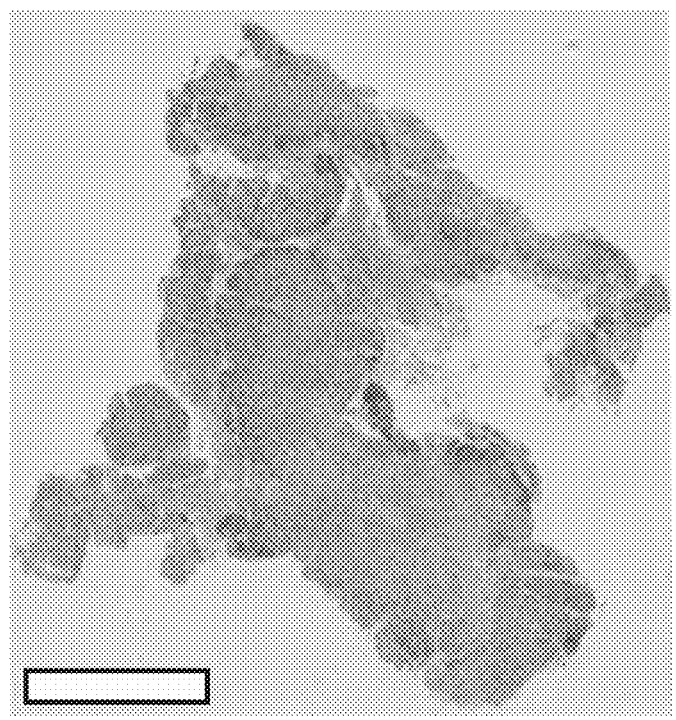
FIG. 10A and FIG. 10B depict H&E staining of thymus tissue slices on day 21 of the time course in a scale of 5 mm (FIG. 10A) and 100 μm (FIG. 10B), respectively. Note the preservation of the overall architecture of the tissue including in FIG. 10B the subcapsular cortex, cortical region and medullary region containing numerous Hassall bodies. The small dark cells are mostly necrotic thymocytes that have not yet undergone karyolysis. Photo by Laura P. Hale, MD, PhD, Department of Pathology, Duke University.
Figure 10B:
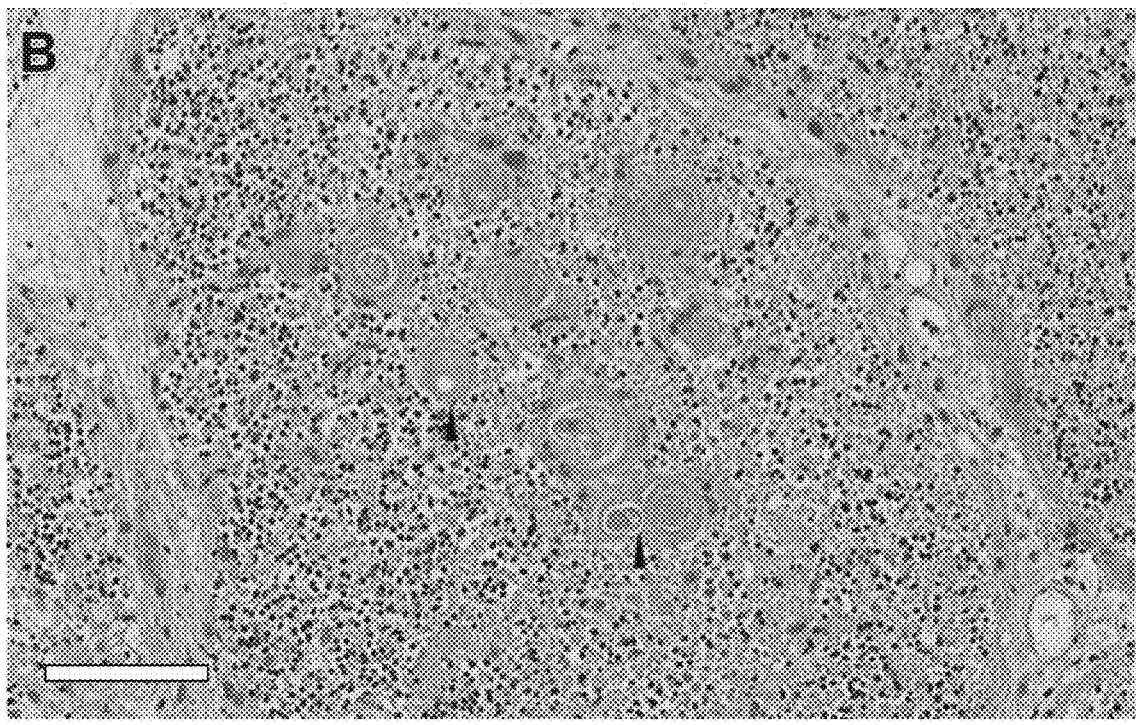
Figure 11A:
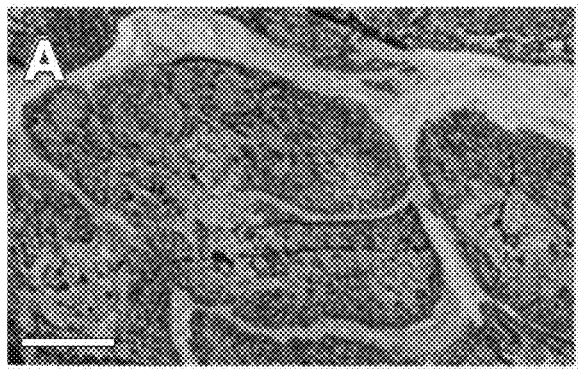
FIGS. 11A-E depict representative thymus slices which were immuno-stained with a cocktail of anti-cytokeratin antibodies (AE1/AE3).
Figure 11B:
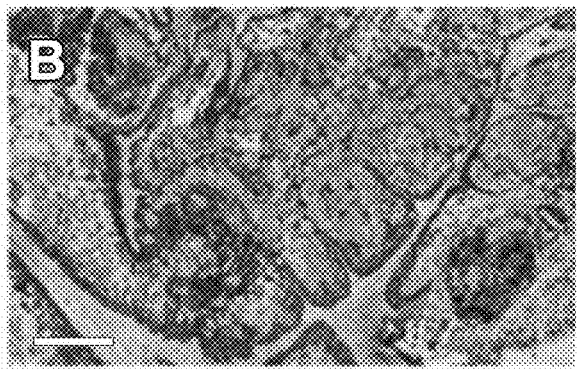
Figure 11C:
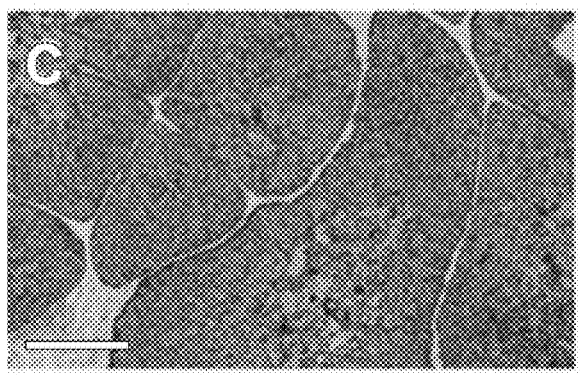
Figure 11D:
Figure 11E:
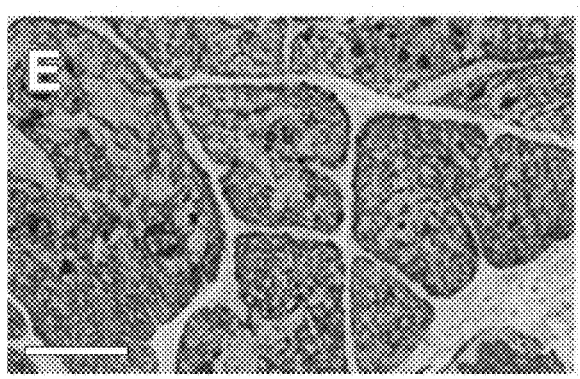

FIGS. 12A and 12B depict the histology of thymus tissue slides after exposure to forced degradation conditions. FIG. 10 depicts the histologic appearance of control thymus tissue slices at day 21.

The general histologic appearance of the forced degradation tissue is similar at these time points, but with fewer residual thymocytes at day 21 (FIG. 12B). Representative Hassall bodies in medullary areas are indicated by arrow heads in FIG. 12B. Representative viable-appearing thymic epithelial cells are indicated by arrows in FIGS. 12A and 12B. The cortical area shown in FIG. 12B consists almost entirely of necrotic lymphocytes day 21. The bars at the lower left represent 100 μm.

Example 4: Thymus Tissue Drug Substance Batch Analysis

Batch analysis data for 10 lots of thymus tissue are shown in Table 8 below.

TABLE 8

| Lot | Year of Manufacture | Weight of incoming thymus (g) | Final dose given to patient ($mm^2/m^2$) | Appearance[b] | Histology[c] | Endotoxin | Sterility[d] | Mycoplasma[d] | Gram stain |
|---|---|---|---|---|---|---|---|---|---|
| MLM428 | 2016 | 4.97 | 8,034 | pass | pass | <0.500 EU/mL | No growth | No growth | Negative |
| MLM434 | 2016 | 7.48 | 9,110 | pass | pass | <0.500 EU/mL | No growth | No growth | Negative |
| MLM435 | 2016 | 27.74 | 7,104 | pass | pass | <0.500 EU/mL | No growth | No growth | Negative |
| MLM437 | 2016 | 8.99 | 9,884 | pass | pass | <0.500 EU/mL | No growth | No growth | Negative |
| MLM438 | 2017 | 10.68 | 19,134 | pass | pass | <0.500 EU/mL | No growth | No growth | Negative |
| MLM444 | 2017 | 10.51 | 19,402 | pass | pass | <0.500 EU/mL | No growth | No growth | Negative |
| MLM447 | 2017 | 5.95 | 8,459 | pass | pass | <0.500 EU/mL | No growth | No growth | Negative |
| MLM449 | 2017 | 7.81 | 9.260 | pass | pass | <0.500 EU/mL | No growth | No growth | Negative |
| MLM450 | 2017 | 12.99 | 17,128 | pass | pass | <0.500 EU/mL | No growth | No growth | Negative |
| MLM452 | 2017 | 7.61 | 16,802 | pass | pass | <0.500 EU/mL | No growth | No growth | Negative |

Testing performed on RVT-802[a]

Key:
[a]These lots were tested according to the specification that was in place at the time of manufacture. The drug substance testing results presented in this table also represents the final drug product testing results.
[b]The appearance specification was no evidence of tampering or damage to containers.
[c]The histology assay was used for both identity and potency. The histology specification (tested between days 5-9) was the following:
[d]Areas positive for keratin scattered throughout the tissue. i. At least 1 Hassall body identified ii. CK14 staining scattered throughout the tissue iii. Intact nuclei observed iv. Sterility and mycoplasma samples were collected on days 1, 7 and 14.

Key:
(a) These lots were tested according to the specification that was in place at the time of manufacture. The drug substance testing results presented in this table also represents the final drug product testing results.
(b) The appearance specification was no evidence of tampering or damage to containers.
(c) The histology assay was used for both identity and potency. The histology specification (tested between days 5-9) was the following:
(d) Areas positive for keratin scattered throughout the tissue.
  i. At least 1 Hassall body identified
  ii. CK14 staining scattered throughout the tissue
  iii. Intact nuclei observed
  iv. Sterility and *mycoplasma* samples were collected on days 1, 7 and 14.

Data for 56 clinical thymuses, 8 thymuses used for intra-thymus variability, inter-thymus variability and time-course testing, and 3 thymuses that had undergone forced degradation were used to generate the current control library. The forced degradation samples in the library (negative controls) were the ones that had undergone degradation by exposure to freeze/thaw or to 10×PBS. The full data set resulted in 14 different clusters. All forced degradation samples clustered together and no clinical samples or characterization samples clustered with the forced degradation samples.

Example 5

Figure 20:
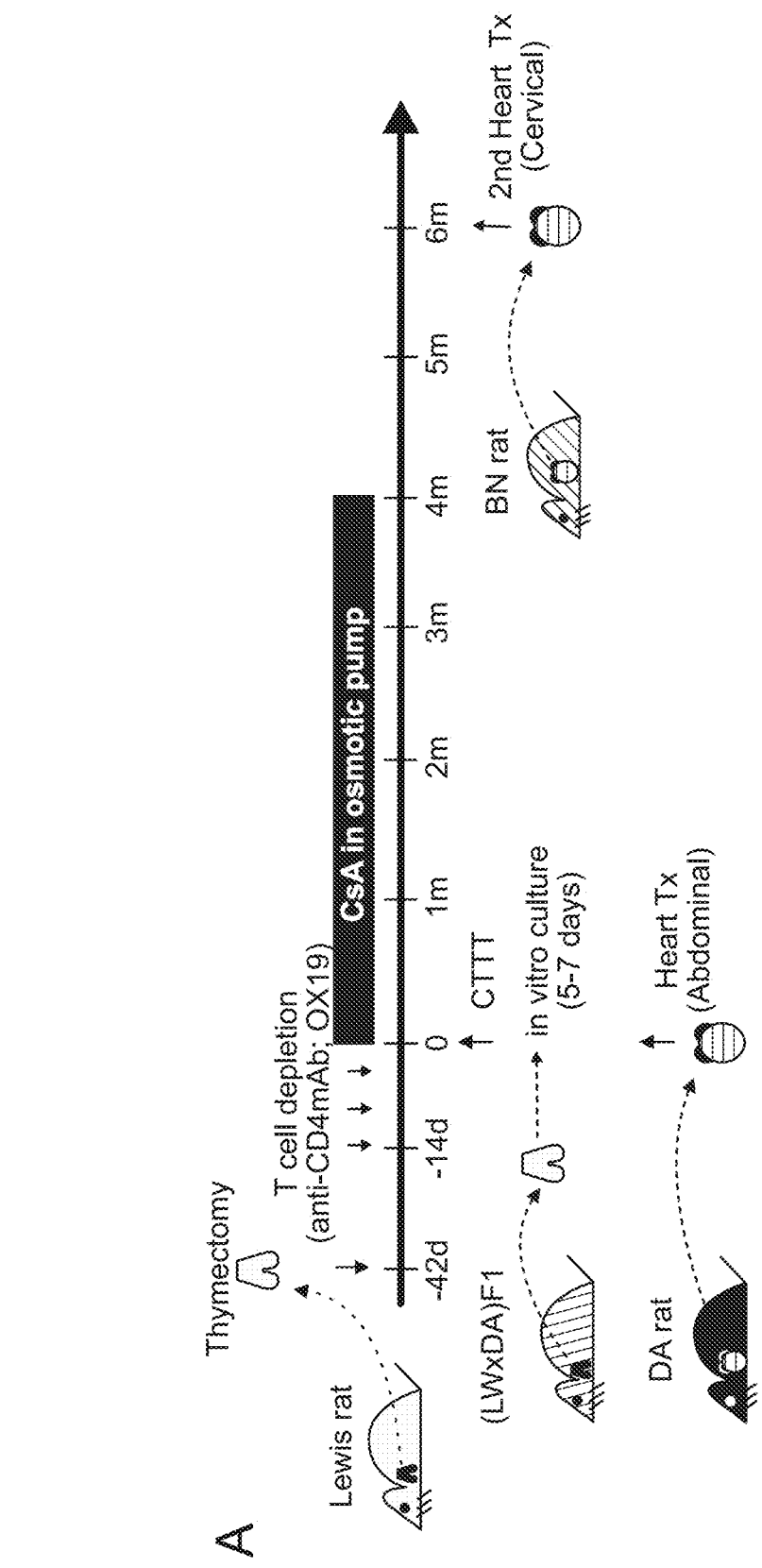
FIG. 20 is a schematic of the experimental design of the experiment reported in Example 5. This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.

The overall experimental design of Example 5 is depicted in FIG. 20. A schematic representation of surgical procedures and treatment schedule is presented. The figures and much of the text below come from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.

The schematic presentation of the experimental design depicts naïve T cell reconstitution, thymopoiesis, and donor-specific tolerance induced by the surgical insertion of CTT. All Lewis (LW) rats were thymectomized and T cell depleted via anti-CD5 mAb prior to heart transplantation and surgical insertion of a CTT. CTT from F1 (LW×DA) rats and hearts from DA rats were transplanted into thymectomized LW recipients. Cyclosporine (CsA) was given for four months after transplantation via osmotic pump. The third-party BN heart was transplanted into the neck 2 to 3 months after CsA discontinuation. Control rats experienced identical procedures except they did not receive a surgical insertion of CTT Example 5 demonstrates that CTT implanted in an immunoincompetent rat model, as described below, can induce tolerance to a transplanted solid organ. We performed haplomatched F1 (Lewis×Dark Agouti, LW×DA) a transplant of CTT (cultured as described below) with vascularized mismatched DA heart transplants into Lewis rats.

Prior to the transplant of CTT, recipients were thymectomized and T cell depleted.

Figure 23:
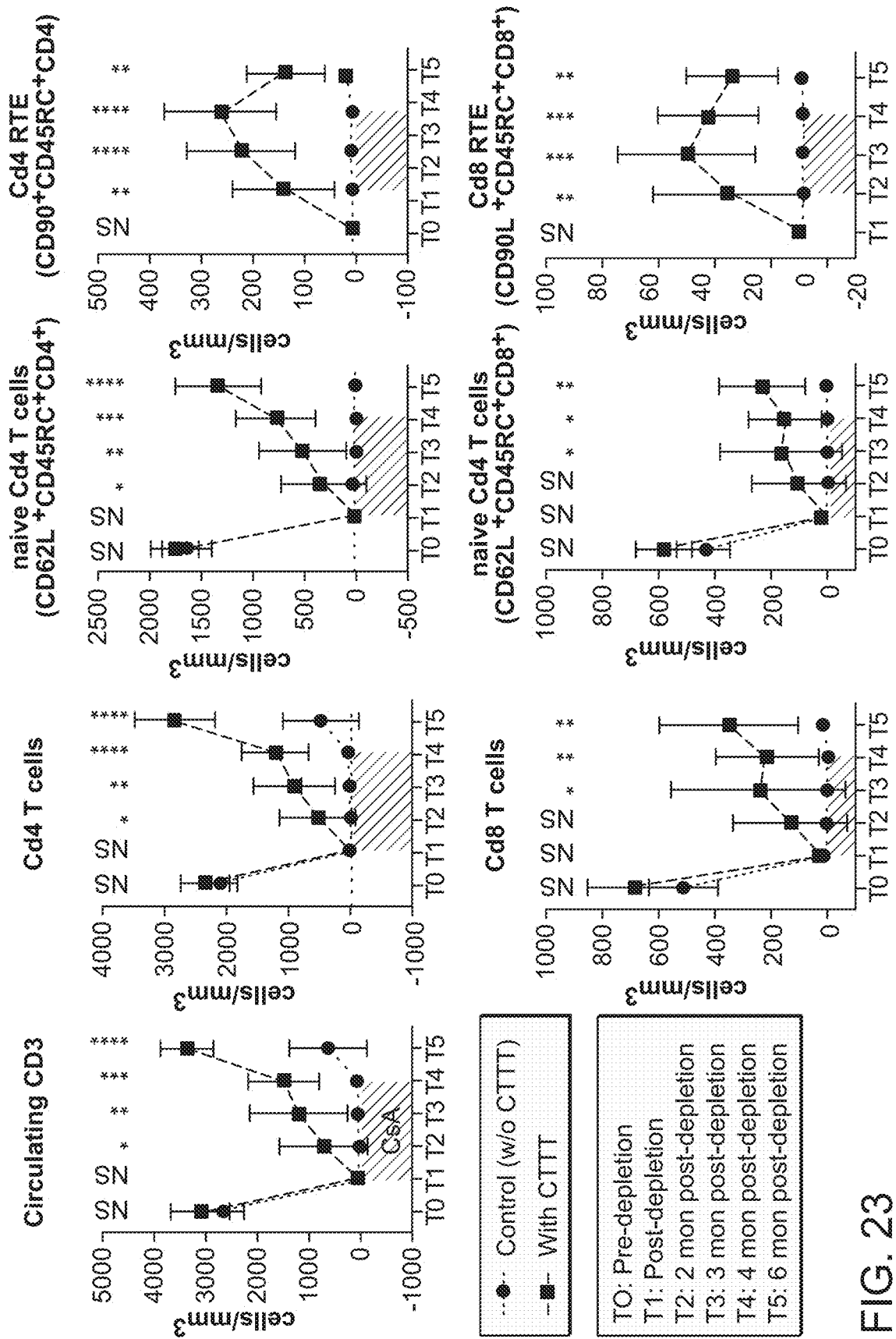
FIG. 23 shows plots of significantly increased numbers of circulating CD4 and CD8 T cells compared to control animals without transplantation of CTT. It also shows significantly increased numbers of naïve CD4 and naïve CD8 T cells in the cultured thymus tissue transplantation (CTTT) group compared to the control group that did not receive CTTT and significantly increased numbers of CD4 and CD8 recent thymus emigrants (RTE) in the cultured thymus tissue transplantation (CTT) group compared to the control group that did not receive CTT. This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.

Cyclosporine was administered for 4 months starting on the day of heart transplantation. The control group did not receive a transplant of CTT. Two months after discontinuation of immunosuppression, recipients transplanted with CTT showed repopulation of naïve CD4 (CD62L+ CD45RC+) T cells in the peripheral blood; control rats had none (FIG. 23). Even after developing recent thymic emigrant CD4 (CD90+CD45RC+) T cells, recipients transplanted with CTT did not reject the DA cardiac allografts (FIG. 23). Controls did not reject the DA grafts, due to lack of functional T cells (FIG. 23).

Figure 24A:
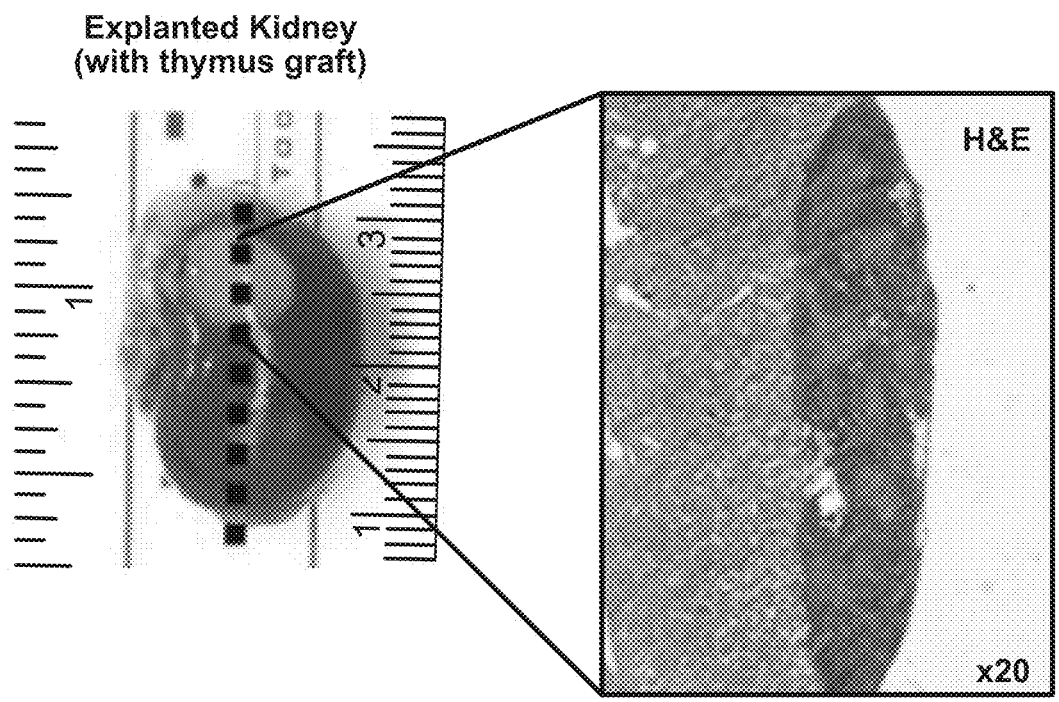
FIG. 24A shows immunohistologic analysis of transplanted CTT explanted on day 180 showing normal thymus histology under the capsule of the kidney (right hand side of FIG. 24A).
Figure 26A:
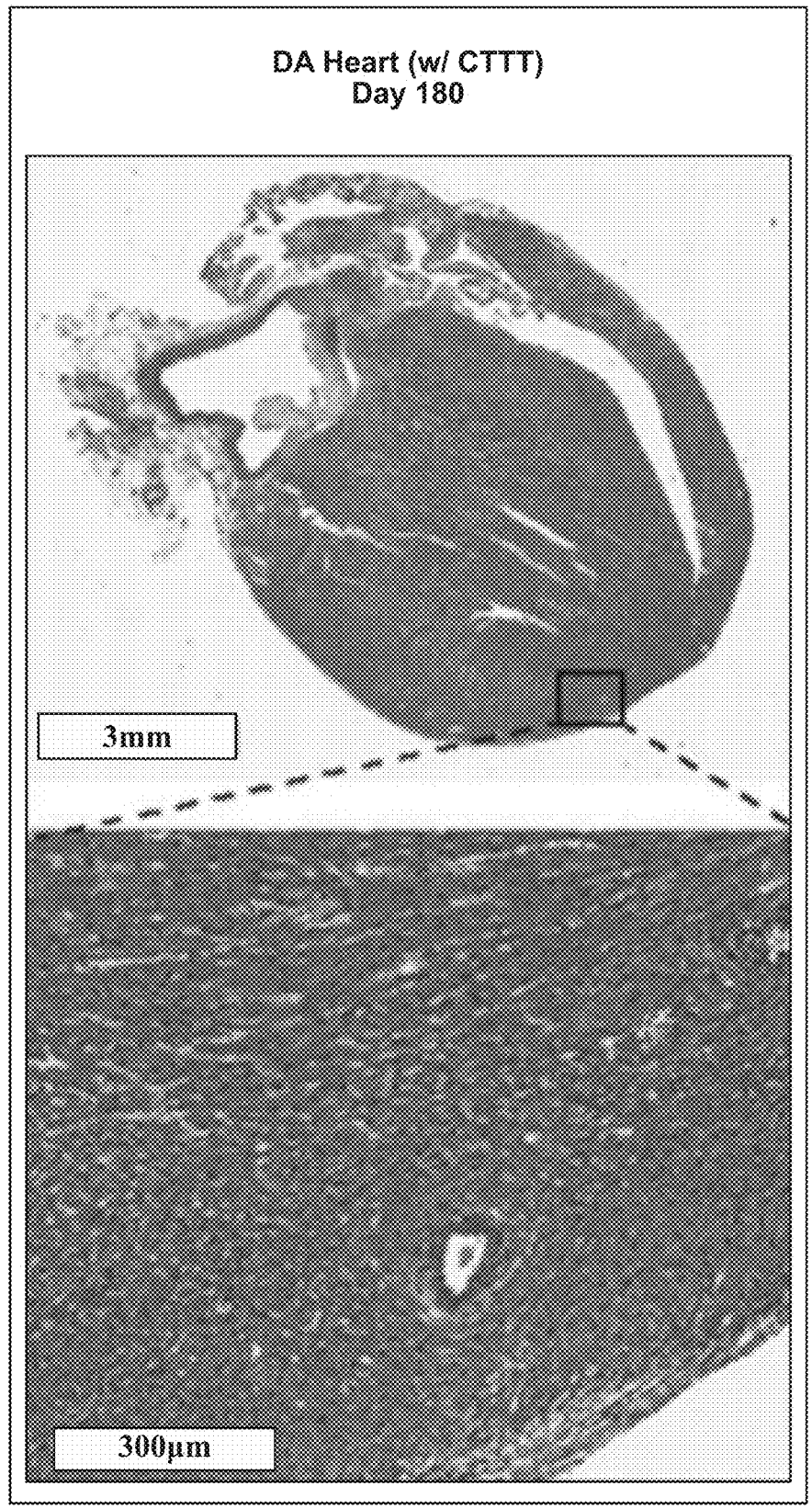
FIGS. 26A and 26B are photographs of transplanted allografts (DA hearts) from animals transplanted with (FIG. 26A) and without (FIG. 26B) CTT showing mononuclear cell infiltration with no signs of rejection by 2004 International Society for Heart &Lung Transplantation (ISHLT) depicted in FIG. 26C (the solid blue squares and solid red triangles). This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.
Figure 26B:
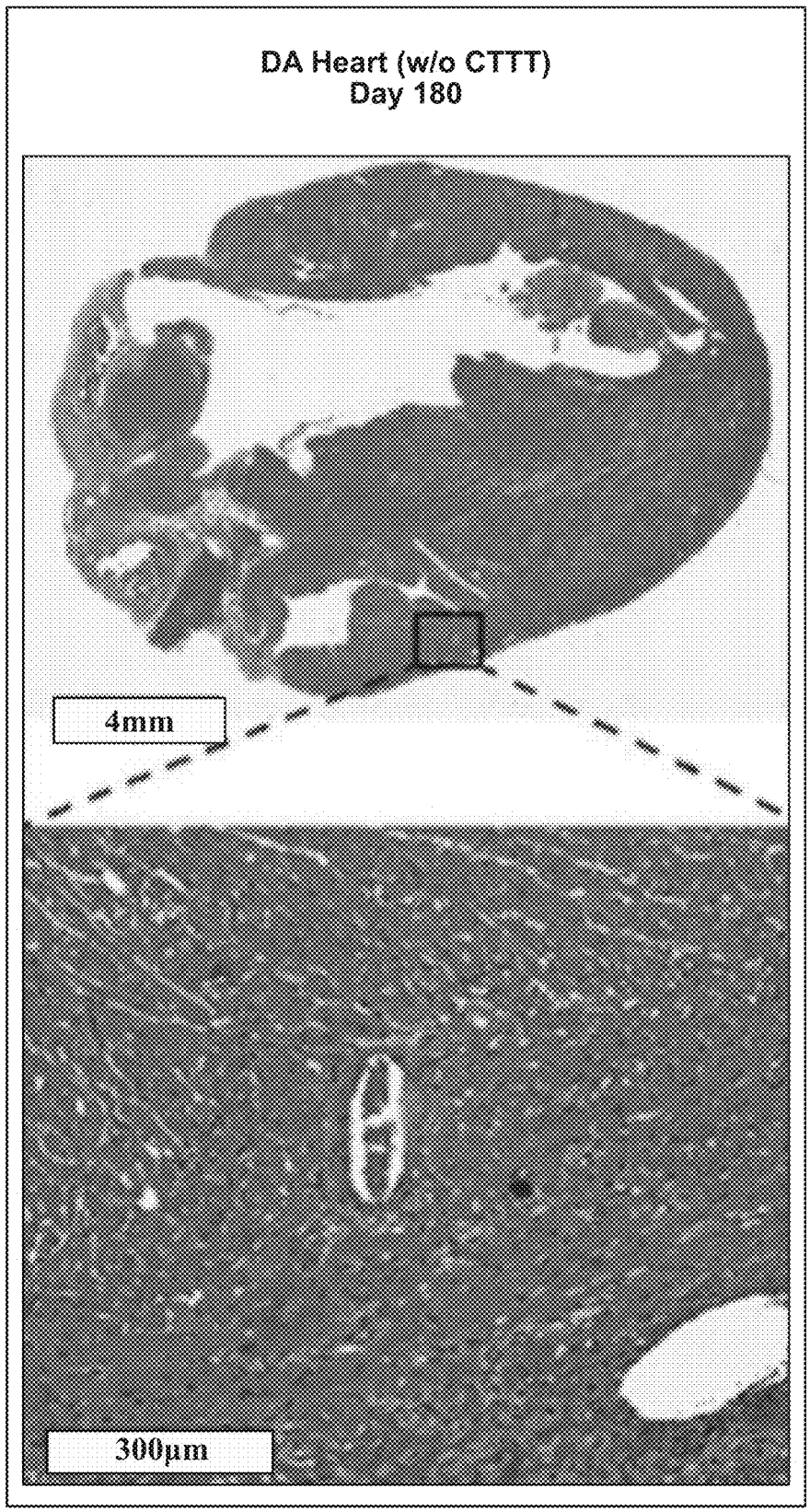
Figures 26C, 27:
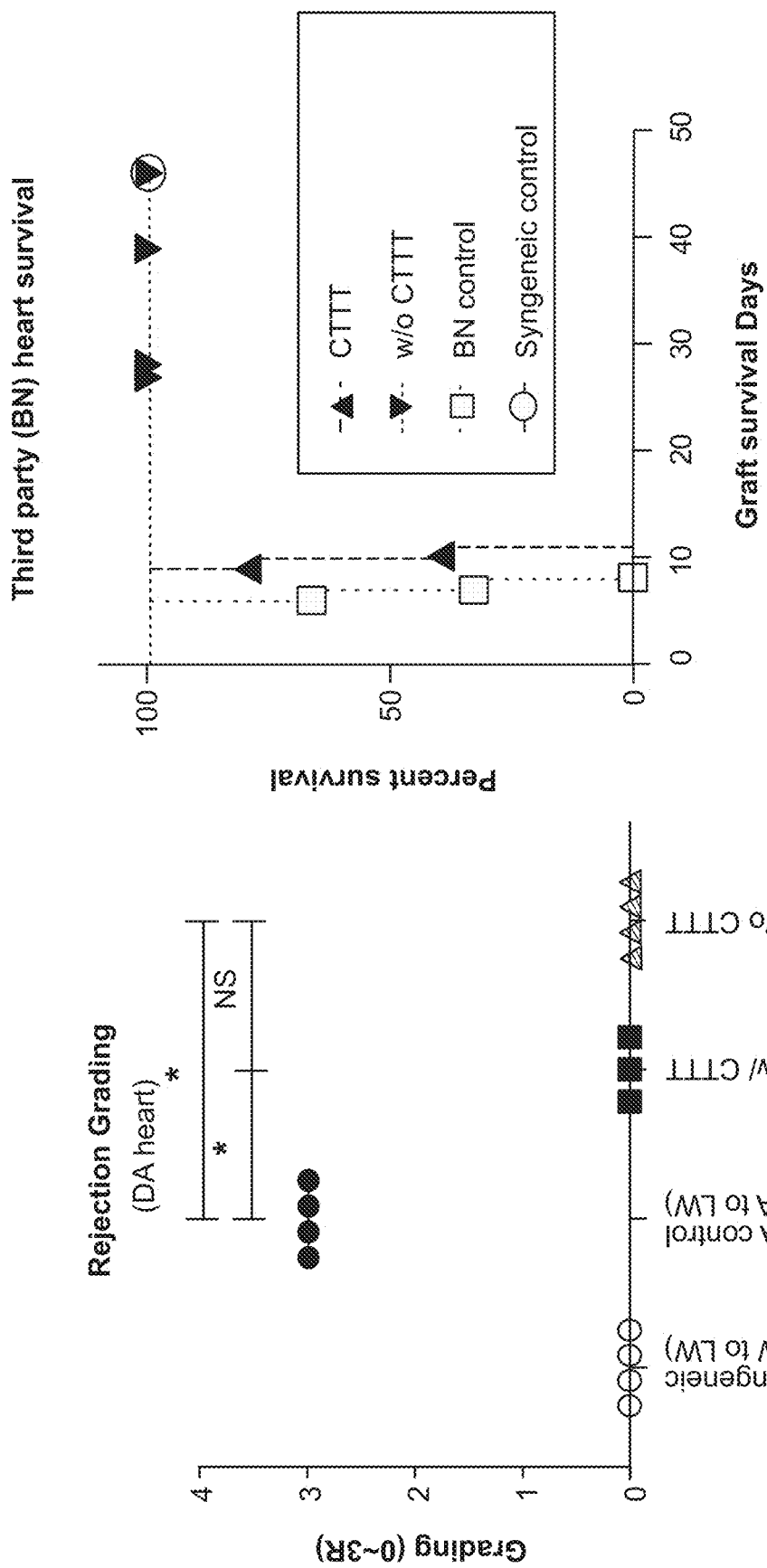
FIG. 27 is a plot of BN heart graft survival in the neck percentage animal survival vs. graft survival days in LW rats with CTT (that were immunocompetent and rejected the cervical allogeneic BN heart) and control LW animals without CTT (that were immunodeficient because of lack of thymus and could not reject the cervical BN heart) inserted vs. BN control (LW rat rejecting a cervical BN heart) and syngeneic controls (LW rats do not reject cervical LW hearts). This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.
Figure 32A:
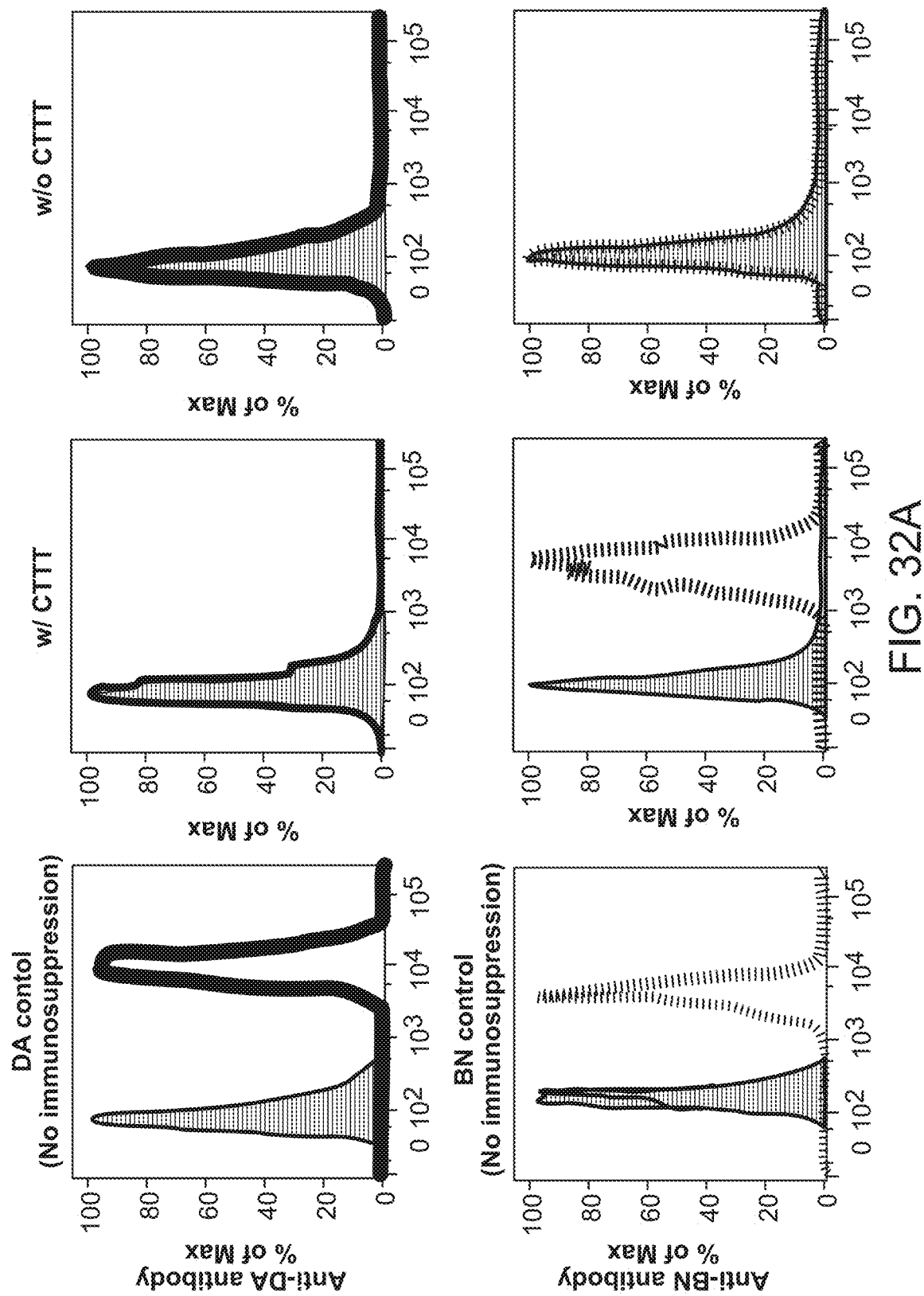
FIG. 32A to FIG. 32C: Humoral tolerance after CTTTCTT.

To confirm donor-specific unresponsiveness, an MHC-mismatched Brown Norway (BN) heart was transplanted on day 180 after the initial mismatched DA heart transplant. LW rats with F1 (LW×DA) transplants of CTT rapidly rejected the third-party BN heart (mean time of rejection, 10d; n=5) (FIG. 27). Controls did not reject the third-party heart (n=5). Recipients of CTT were able to produce antibody against third party BN donor but not against the DA thymus donor demonstrating humoral donor-specific tolerance (FIG. 32A). Immunohistochemistry of the transplanted CTTs at necropsy showed functional thymus tissue (FIG. 24). Taken together, F1(LW×DA) CTTT given to Lewis rats resulted in specific tolerance to the allogeneic DA MHC expressed in the donor thymus with resulting long-term survival of DA heart transplants after withdrawal of all immunosuppression.

Materials and Methods.
Animal Models

Figure 17A:
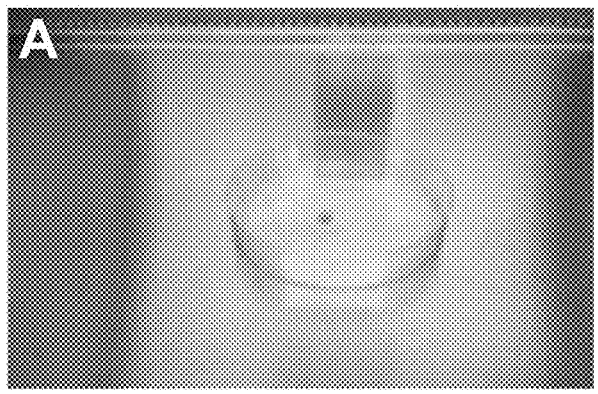
FIGS. 17A-D present photographs of the harvesting of thymus tissue from 3-day old F1 (LW×DA) rats that was cut into four pieces as described in Example 5 (FIG. 17A). A photograph of thymus pieces cultured on sterile mixed cellulose ester filters with thymus organ medium for 5-7 days in a 37° C. $CO_2$ incubator, as described in Example 5 (FIG. 17B).

In this Example 5, allogeneic CTT was harvested and cultured from 3-day old F1 (Lewis×Dark Agouti ray pups (FIGS. 17A and 17B), as described below, and then implanted into thymectomized Lewis (RT-1) recipient rats in a manner comparable to the treatment of human infants with athymic cDGA, as described previously. (Markert, M L, et al., 2008; Market, M L, et al., 2010).

Lewis (RT-11) and BN (RT-ln) rats were purchased from Charles River. DA (RT-1av1) rats were purchased from Envigo. F1(LEW/DA; RT-11/av1) were bred by protocol staff at the Duke Breeding Core Division of Laboratory Animal Resources facility. Lewis recipients received thymectomies as described in Rendell V R, Giamberardino C, Li J, Markert M L, & Brennan T V, 2014, "Complete thymectomy in adult rats with non-invasive endotracheal intubation." *J Vis Exp* (94).

Briefly, the submandibular glands and sternohyoid muscle were separated with blunt forceps to expose the tissue overlying the trachea. A 1- to 1.5-cm incision was made in the sternal manubrium. A 7 cm alms-type retractor was used to retract the manubrium and the two halves of the sternohyoid muscles to expose the thymus. The thymus was grasped with blunt forceps and extracted. The cut ends of the sternum were closed with a single 3 to 4-0 silk suture. Two drops of 2.5 mg/ml bupivacaine were applied on the incision and the outer layer of skin was closed with three or four 9-mm wound clips.

All thymectomized rats were maintained on a diet containing Septra® (trimethoprim-sulfamethoxazole) (PMI Nutrition International, LLC). To induce T cell depletion in vivo, 1 mg anti-CD5 mAb (OX19; BioXCell, NH) was intraperitoneally administered on days 0, 5, and 10 after thymectomy and suppression with 0.25 mg/kg/d cyclosporine pump was given from day 0 (heart transplant & CTTT time point) to 4 months with respect to heart transplantation. All rats were used and maintained in accordance with the guidelines and compliance of the Duke Institutional Animal Research Ethics Committee.

In Vitro Thymus Culture and CTT

Figure 17B:
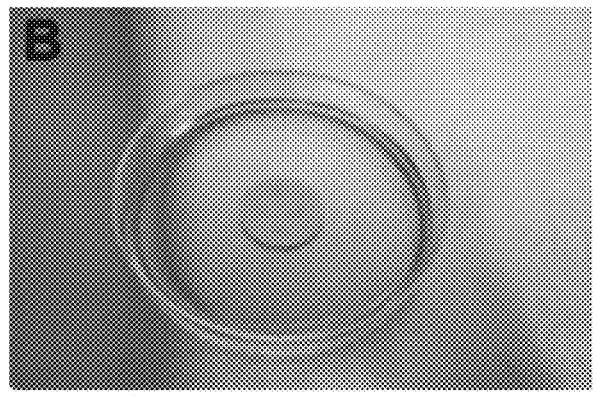
Figures 17C, 17D:
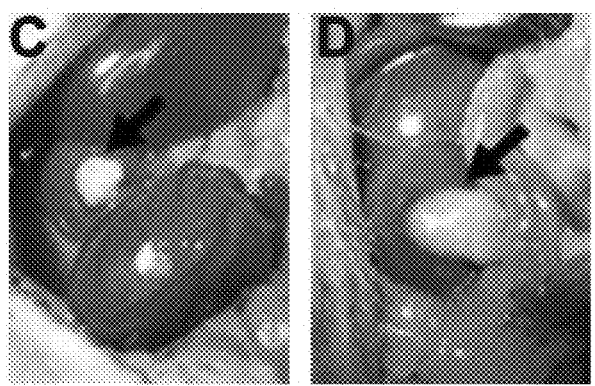

Thymuses from three day's old neonatal F1 (LEW/DA) rat pups were harvested sterilely, cut into four pieces along the longitude natural seam, and transferred onto sterile nitrocellulose filters (MF-Millipore®, Millipore Sigma) in a tissue culture dish with TOM medium (FIG. 17B). Thymus tissue was cultured in a $CO_2$ incubator with 5% $CO_2$ at 37° C. for the desired length of time (5 to 7 days). The medium was changed daily. The thymus organ medium (TOM) was composed of HAMS F12 (Life Technologies) at 86.5%; Hepes (Life Technologies) at 25 mM; L-Glutamine Life Technologies) at 2 mM; Fetal Bovine Serum (Life Technologies) at 10%; and Pen-strep (Life Technologies) at 1×. On the day of transplantation, the thymus pieces were rinsed with fresh medium and transplanted under the kidney capsule of a Lewis rat with one secure suture (10-0 monofilament). See FIG. 17C. All manipulations took place under sterile conditions in a biological safety cabinet.

Abdominal and Cervical Heart Transplantations

Full MHC mismatched DA ($RT-1^{av1}$) donor hearts were transplanted into thymectomized Lewis (RT-1) recipients. Abdominal heart transplantation was performed using a modified technique of the methods described by Schmid C, Binder J, Heemann U, & Tilney N L, 1994, "Successful heterotopic heart transplantation in rat," *Microsurgery* 15(4):279-281.

Briefly, the donor heart was transplanted into the abdominal cavity of the recipient after a short period of cold ischemia in Euro-Collins solution. The donor pulmonary artery and aorta were anastomosed to the recipient inferior vena cava and descending aorta with an end-side fashion as the inflow and outflow vessels for circulation, using running 9/0 non-absorbable monofilament sutures. Cyclosporine A (CsA) was given via the osmotic pump (Model 2ML4, Alzet). The recipients also received cyclosporine (CsA), approximately 2.5 mg/kg/day after thymus transplantation using osmotic pumps. CsA was discontinued 4 months after thymus transplantation when the test group had naïve T cells over 10%. The pump was loaded sterilely and surgically inserted subcutaneously to mid-dorsal area of recipients. The osmotic pump was replaced every month for 4 months. For full MHC mismatched BN (RT-1") third-party heart transplantation to the DA heart bearing Lewis recipients the cervical vascularized heart transplantation method described by Heron, et al. (Heron I., 1971, "A technique for accessory cervical heart transplantation in rabbits and rats," *Acta Pathol Microbiol Scand A* 79(4):366-372) was used in modified fashion.

At 6 to 7 months, the 3rd party BN heart was transplanted in the neck. Briefly, the third-party heart was transplanted into the right side of cervical area via a longitudinal incision from submaxilla to the xiphoid. The donor pulmonary artery and external jugular vein were anastomosed end to end and the aorta was anastomosed to the right common carotid artery by cuffing technique. The grafts were monitored by daily palpation and later confirmed by laparotomy at the time of sacrifice. Animals were sacrificed on the day of rejection (cessation of beating) or a designated time point.

Flow Cytometric Analysis and Monitoring DSA

Peripheral blood was obtained from the cranial vena cava and stained with antibodies. To analyze naïve and recent thymic emigrants, we used the combination of anti-Rat CD3 APC (BD Biosciences); anti-Rat CD4 APC-Cy7 (Biolegend); anti-Rat CD8a V450 (BD); anti-Rat CD45 PE-Cy7 (BD); anti-Rat CD45RC-PE (BD); anti-Rat CD62L FITC (BD); and anti-Rat CD90 BV 510 (Biolegend). To assess percentages of T, B, and NK cells, we used the combination of anti-Rat TCR FITC (BD); anti-Rat CD4 APC-Cy7(Biolegend); anti-Rat CD8a V450 (BD); anti-Rat CD45 PE-Cy7 (BD); anti-Rat CD45RA PE (Invitrogen); anti-Rat NKR-P1A-APC (Invitrogen). For host vs donor discrimination, we used the combination of anti-Rat TCR APC (Biolegend), anti-Rat CD45 PE-Cy7 (BD); MHC Class I RT1Aa (Santa Cruz Biotechnology). We also used a secondary goat anti-mouse IgG (Invitrogen) for the non-conjugated MHC Class I RT1Aa. Donor-specific alloantibody (DSA) was assessed by flow cross-match from serially collected recipient serum samples with DA donor or BN third party rats. FITC-conjugated pan-rat immunoglobulin antibody was added to the samples and incubated after washing. The T cells were stained with APC-conjugated anti-CD3. Samples were analyzed on a LSR fortessa (Beckman Coulter).

Necropsy

Figure 21:
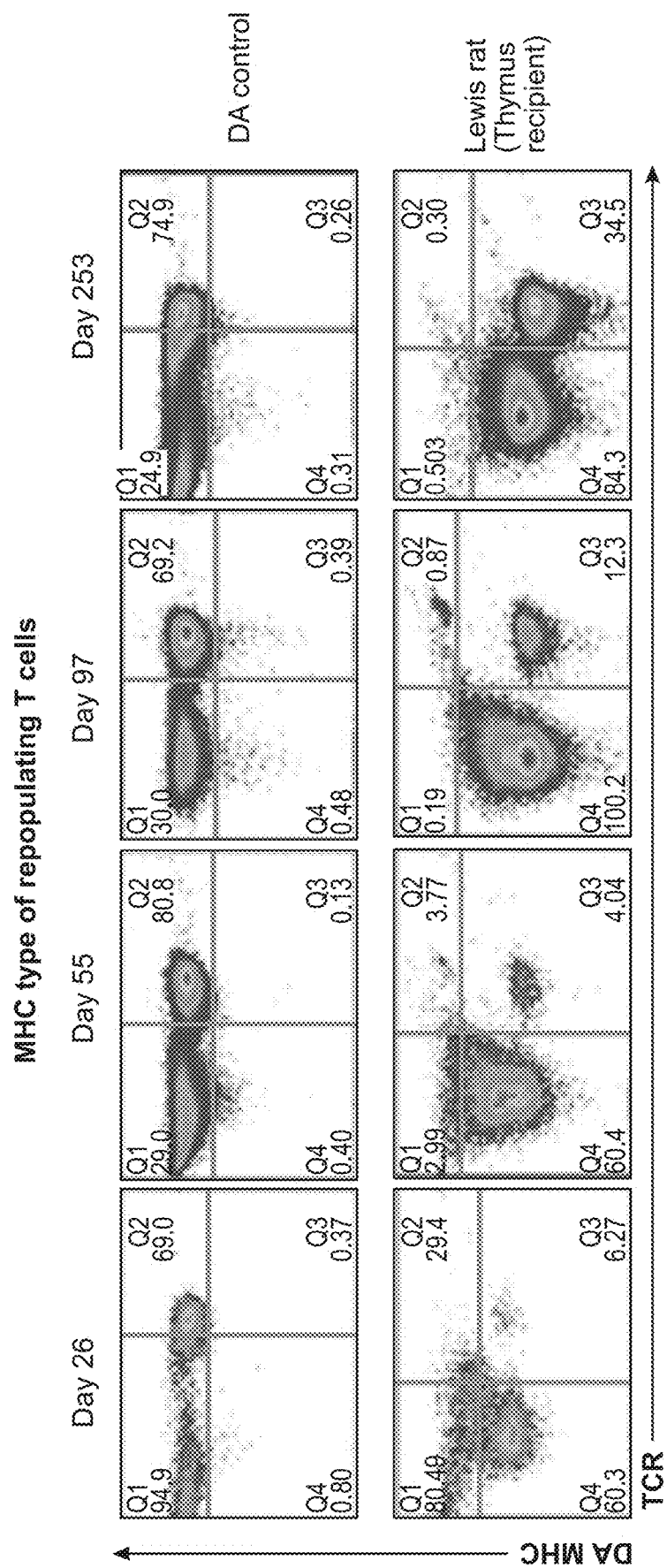
FIG. 21 shows repopulating recipient-type T cells are seen in the lower right quadrant after CTT transplantation. This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.

The thymus graft and all hearts were evaluated at necroscopy 8 months after CTTT when the test group rejected the cervical BN heart. As predicted, recipient-derived T cells, not expressing DA MHC, appeared in the peripheral blood of thymus transplant recipients (FIG. 21).

Histology, Immunohistochemistry (IHC), and Morphological Analysis

All cultured thymus and CTTT samples from under the kidney capsule were frozen in OCT (Tissue Tek® Optimal Cutting Compound; (water soluble glycol's and resins compound). Control thymus tissue was obtained from newborn to 5-day-old rat pups. Four to five mm sections were stained for CD3 (polyclonal; Dako), Ki-67 (clone: SP6; Thermo), CK, (polyclonal; Invitrogen). IHC images were obtained using an Olympus Vanox AH-3 microscope of the Olympus DP-70 digital camera system. The explanted hearts underwent serial sectioning (5 μm) from the midventricular level to the base. H&E stains were performed for routine examination and grading of rejection. Graft infiltrating T cells were evaluated with polyclonal anti-CD3 (Dako) staining. Whole slides of grafts were scanned with an Aperio ScanScope® XT (Aperio Technologies, Inc., Vista, CA) (a slide scanner).

Statistical Analysis

Experimental results were analyzed by a GraphPad Prism (GraphPad Software 7.0, San Diego, CA). The log-rank test for differences in graft survival and student t-test or Mann-Whitney U test were used for other data. All the data were presented as mean±SD. Values of p which were less than 0.05 were considered as statistically significant.

Results

Figure 18A:
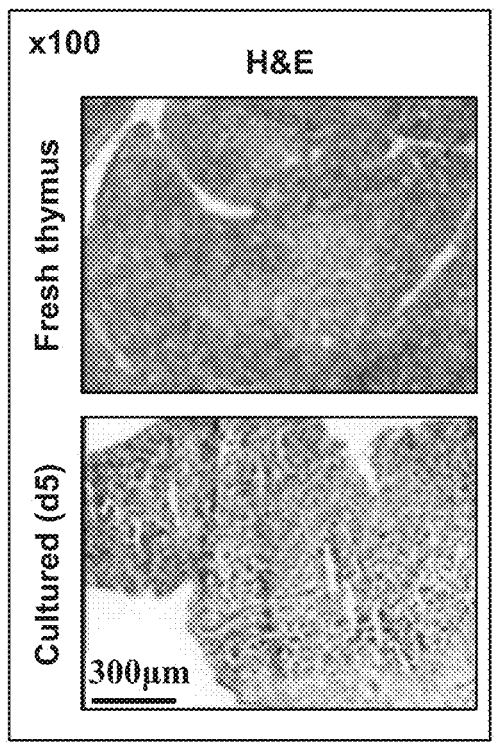
FIGS. 18A-D are photographs depicting the histologic appearance of fresh thymus tissue (top frames) and CTT (bottom frames) at 100× magnification.
Figure 18C:
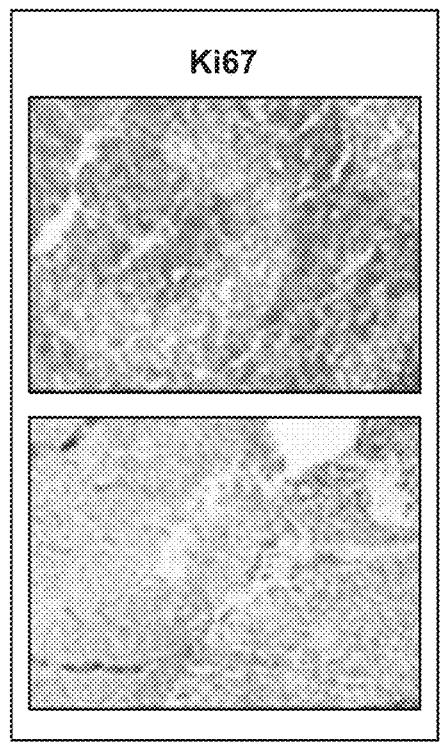
Figure 18B:
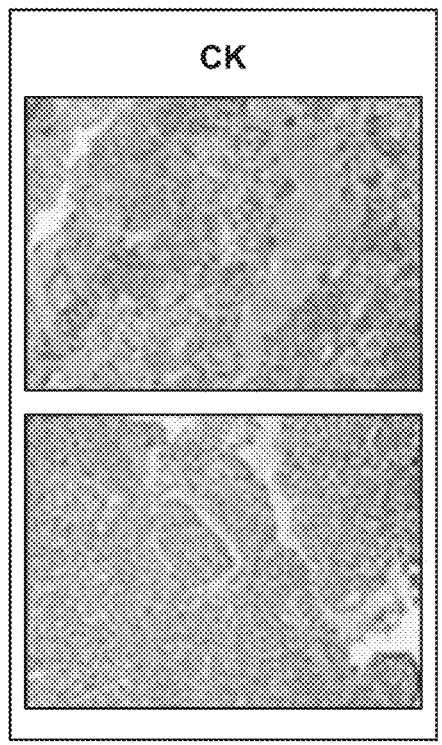
Figure 18D:
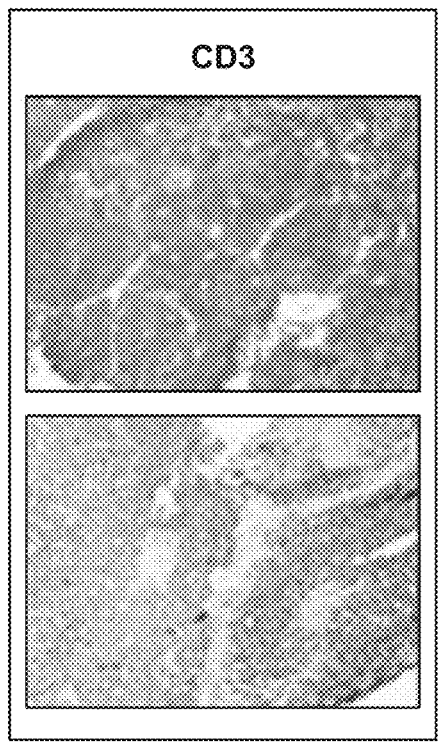
Figure 19A:
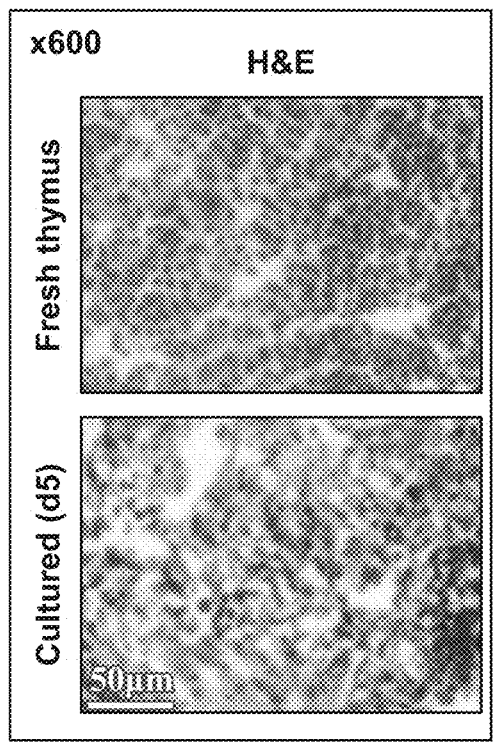
FIGS. 19A-D are photographs depicting the histologic appearance of fresh thymus tissue (top frames) and CTT (bottom frames) at 600× magnification.
Figure 19C:
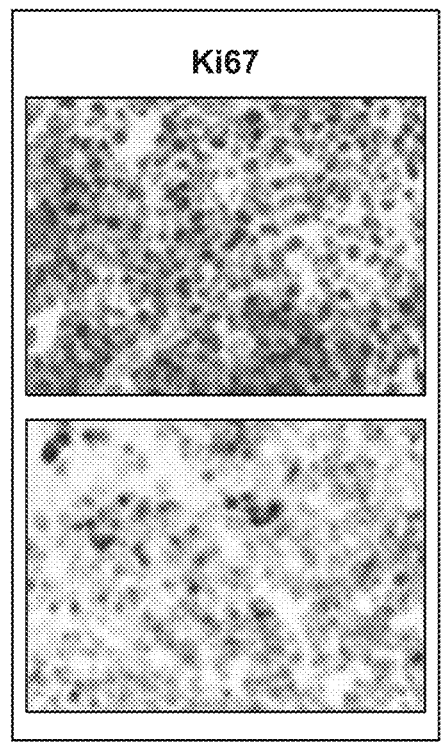
Figure 19B:
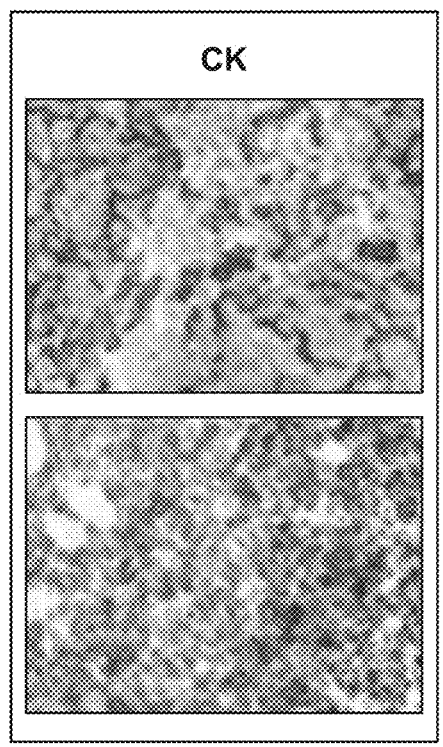
Figure 19D:
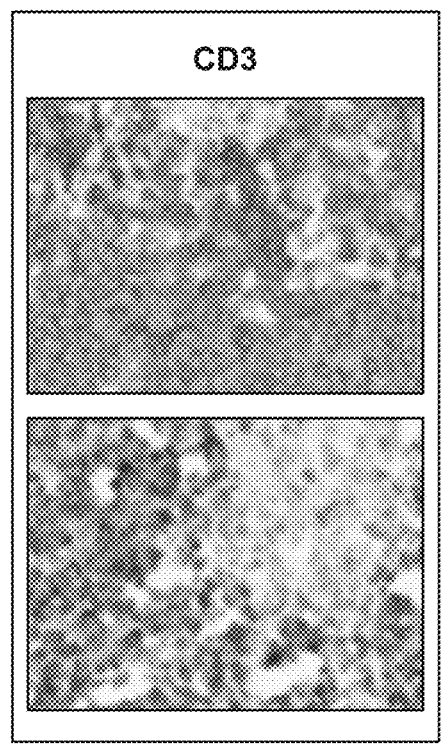

Histologic analysis (FIGS. 18C and 18D (100× magnification) and FIGS. 19C and 19D (600× magnification) showed reduced Ki67+, CD3+ cells in the thymus after culturing, similar to the changes seen after culturing of thymus tissue used for patients (Markert M L, et al., 2008), "Use of allograft biopsies to assess thymopoiesis after thymus transplantation." *J Immunol* 180(9):6354-6364). As in cultured human thymus, the network of thymic epithelial cells (TEC) was preserved in the rat cultured thymus tissue based on cytokeratin (CK) staining (FIG. 18B (100× magnification) and FIG. 19B (600× magnification).

As predicted, recipient-derived T cells, not expressing DA MHC, appeared in the peripheral blood of thymus transplant recipients (FIG. 21). After transplantation of CTT, increasingly repopulating recipient-type T cells are seen in the lower right quadrant of FIG. 21 at days 26, 55, 97 and 253.

Immunohistochemical Analysis of Engrafted Allogeneic Thymic Tissue.

Circulating T cell repopulation after T cell depletion and thymus and heart transplantation are depicted in FIG. 23. All animals showed dramatic reduction of circulating T cells after T cell depletion. Cardiac allograft recipients with a CTT insertion (blue/dashed line) showed gradual repopulation of circulating T cells. Animals without a CTT insertion also showed some degree of circulating T cells (red/dotted line). However, naïve and recent thymic emigrants CD4 and CD8 T cells were significantly increased (p<0.01) in animals with a CTT insertion while control animals showed no circulating naïve nor RTE CD4 and CD8 T cell.

Figure 22A:
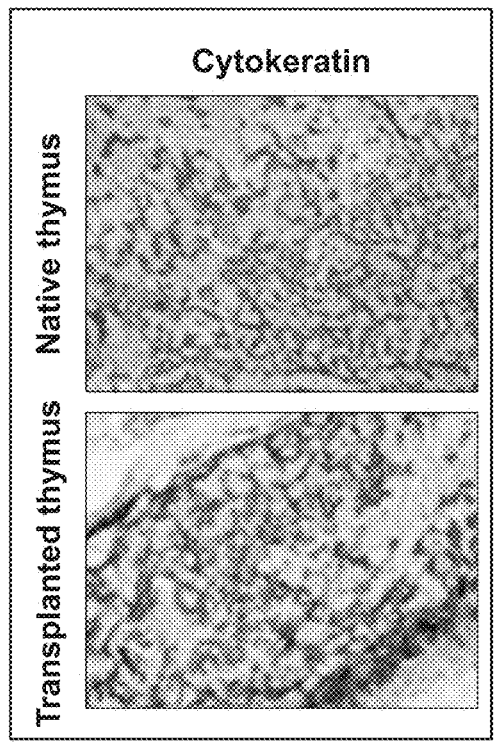
FIG. 22A and FIG. 22B show transplanted thymus explanted at 8.5 month after transplantation showing positive cytokeratin staining (FIG. 22A), as well as T cell staining similar to native thymus (FIG. 22B). Original magnification×400. This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.
Figure 22B:
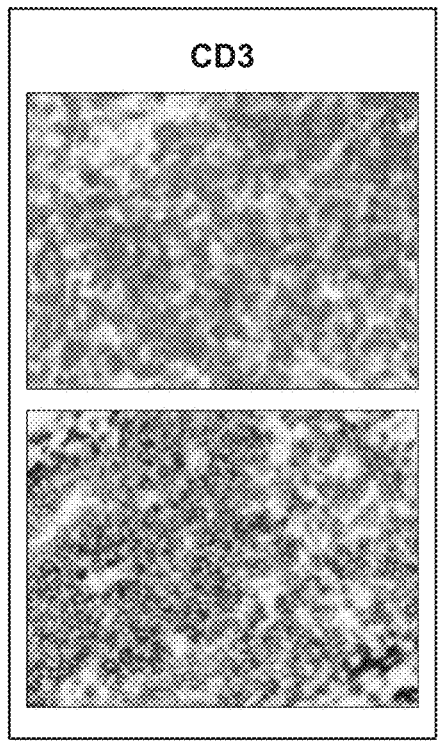

Transplanted thymus explanted at 8.5 month after transplantation showed positive cytokeratin staining (FIG. 22A) as well as T cell staining similar to native thymus (FIG. 22B). Original magnification ×400.

Animals with insertion of CTT showed significantly increased repopulation of naïve (CD62L+CD45RC+) CD4 and CD8 T cells as well as recent thymic emigrant (RTE) T cells in the peripheral blood while control groups without thymus transplantation showed low level of circulating naïve CD4 and CD8 T cells and did not show circulating RTE CD4 and CD8 T cells (FIG. 23). Total circulating CD3 T cell numbers were not significantly different in between groups prior to transplantation. As expected, LW recipients with a CTT transplant showed significantly increased numbers of circulating CD4 and CD8 T cells compared to control animals without transplantation of CTT (FIG. 23).

Engrafted cultured thymus tissues under the renal capsule on day 180 in a recipient of cardiac allograft recipients is depicted in FIG. 24.

Figure 24B:
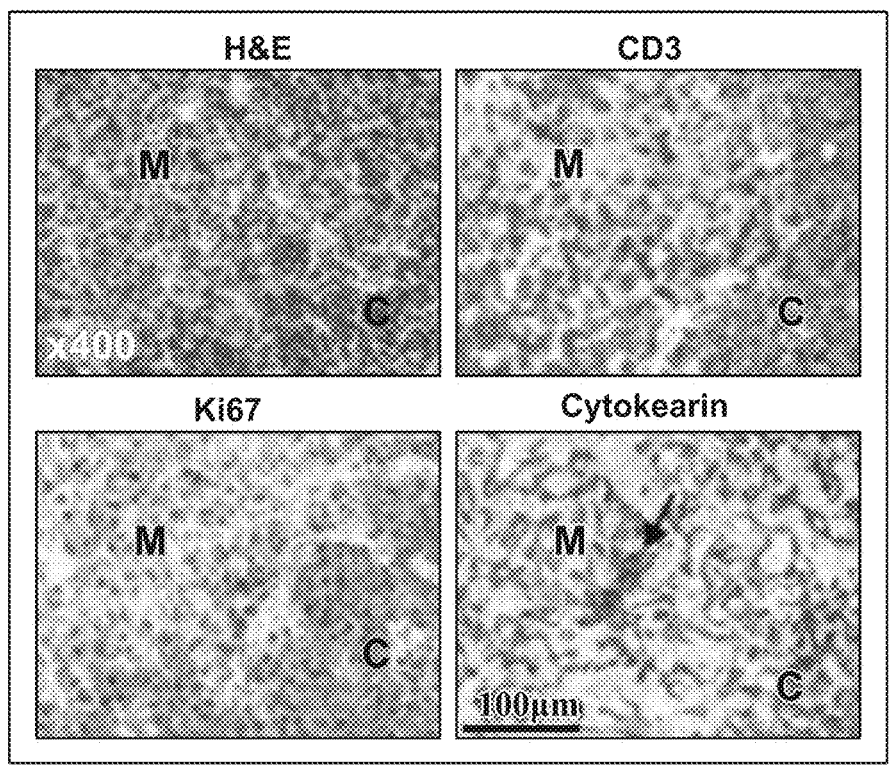
FIG. 24B shows the explanted graft on H&E. Strains for viable T cells (CD3), T cell proliferation (Ki67), and cytokeratin (detected by a rabbit polyclonal antibody) are shown. In the panel stained for cytokeratin, a lacy pattern is seen with Hassall body formation (arrow) on TECs. This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.

Histology showed distinct structures separate from renal tissue (Original magnification, ×20). Engrafted cultured thymus tissue showed a normal thymus structure (H&E), viable T cells (CD3), T cell proliferation (Ki67), and Hassall body formation (Black arrow) with a lacy pattern (Cytokeratin) on epithelial cells, confirming the viability of thymus with thymopoiesis (FIG. 24B). Original magnification, ×200. (Data are presented as means±SD; n=8-9 animals per group; student's t-test, *P<0.05; P<0.01; *P<0.001, ****P<0.0001; NS, not significant (p>0.05).

In addition, immunohistologic analysis of transplanted CTT explanted on day 180 showed normal thymus histology, viable T cells (CD3), T cell proliferation (Ki67), and a lacy pattern of CK with Hassall body formation (arrow) on TECs from the surgical insertion of CTT (FIG. 24B). These observations confirm the viability and function (thymopoiesis) of the transplanted thymus in the animals receiving allogeneic heart transplantation.

Taken together, rats transplanted with CTT demonstrated thymopoiesis with naïve T cell development in cardiac allograft recipients.

It was expected that T cells reactive to the DA donor would not develop since the T cells developed in CTT expressing DA as well as LW.

Figure 25:
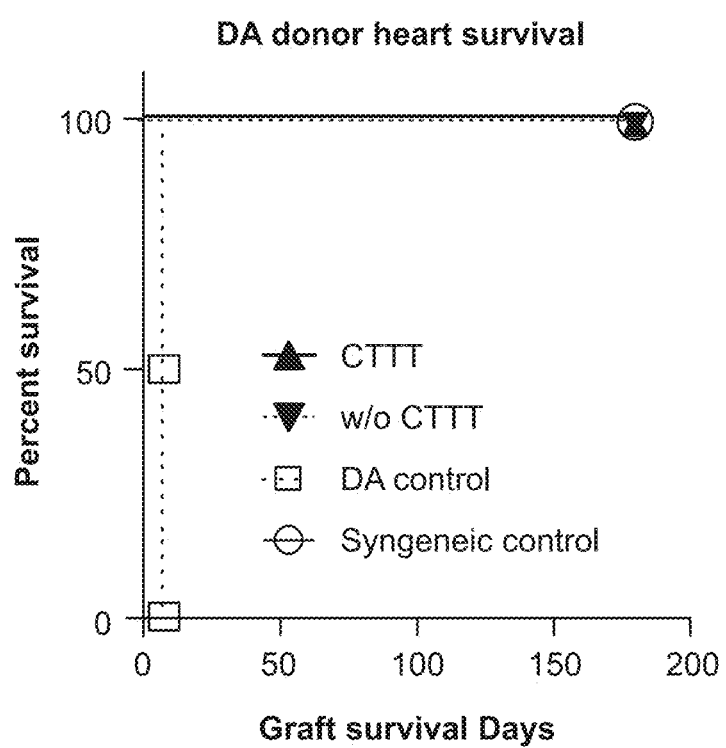
FIG. 25 shows survival percentages of LW rats after thymectomy and immunosuppression with DA heart transplants with CTT (solid triangles, blue line) and without CTT (upside down triangles, red lines) transplants (CTTT). The LW rats with CTTT are tolerant; the LW rats without CTTT are immunodeficient and thus do not reject the DA heart. The control shows complete rejection of DA heart transplants in LW unmanipulated rats (open squares). LW control animals also did not reject an LW cardiac graft (open circle with horizontal line) (n=9). This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.

The DA heart was evaluated for evidence of rejection. FIG. 25 shows LW rats with DA heart transplants and without any immunosuppressive treatment rejected the DA heart grafts within 10 days (the DA control, open squares). However, even after developing RTE (CD90+CD45RC+) T cells, LW recipients with surgically inserted CTT did not reject (no cessation of beating) the DA cardiac allografts (n=8, filled triangles). Unexpectedly, LW control animals without a CTT insertion also did not reject the DA cardiac graft (n=9, upside down filled triangles). Both groups showed good beating quality for the entire study period (day 180). Since continuous graft beating does not necessarily imply absence of rejection, two recipient rats were sacrificed two months after cessation of immunosuppression (i.e., prior to $3^{rd}$ party BN cervical heart transplantation) to confirm that there was no rejection. The explanted cardiac allografts (DA hearts) from both animals showed minimal mononuclear cell infiltration (FIG. 26A, with CTT insertion; and FIG. 26B, without CTT insertion), with no signs of rejection by 2004 International Society for Heart &Lung Transplantation (ISHLT) grading FIG. 26C.

A Kaplan-Meier survival curve (FIG. 25) showed significantly prolonged graft survival from animals with or without CTT and syngeneic controls (LW heart into LW rat) as compared to LW rats with DA heart transplants without any immunosuppression (DA control). Representative scanned images of explanted graft at day 180 from animals with and without CTT are shown in FIGS. 26A and 26B. The images were adapted from whole slide scan.

The ISHLT grading showed no difference in rejection grading between cardiac allografts from recipients with CTT vs. without CTT (n=3-4 per group) (FIG. 26C). Mann-Whiney U test, *P<0.05; NS, not significant (p>0.05).

Based on the reconstitution of naïve T cells after CTTT, we believe that animals with CTT lost their donor-reactive T cell repertoire while animals without thymus transplantation did not fully reconstitute their T cell populations (general hypo-responsiveness).

Alloreactivity Against Third-Party Vascularized Heart Transplantation

To confirm that donor-specific unresponsiveness (tolerance) was achieved as opposed to general hypo-responsiveness, additional fully MHC mismatched BN heart transplantation was performed in both groups of animals at 6 to 7 months (day 180 to 210) after DA heart transplantation.

LW rats with CTT inserted (solid triangles. FIG. 27) rapidly rejected (cessation of graft beating) the third-party BN heart (n=5, median survival time (MST)=10±1.0 days). However, the control LW animals without CTT inserted did not reject the third-party hearts (n=6, MST≤38.5±8.9 days), possibly due to the lack of any alloreactive T cells.

Figure 28A:
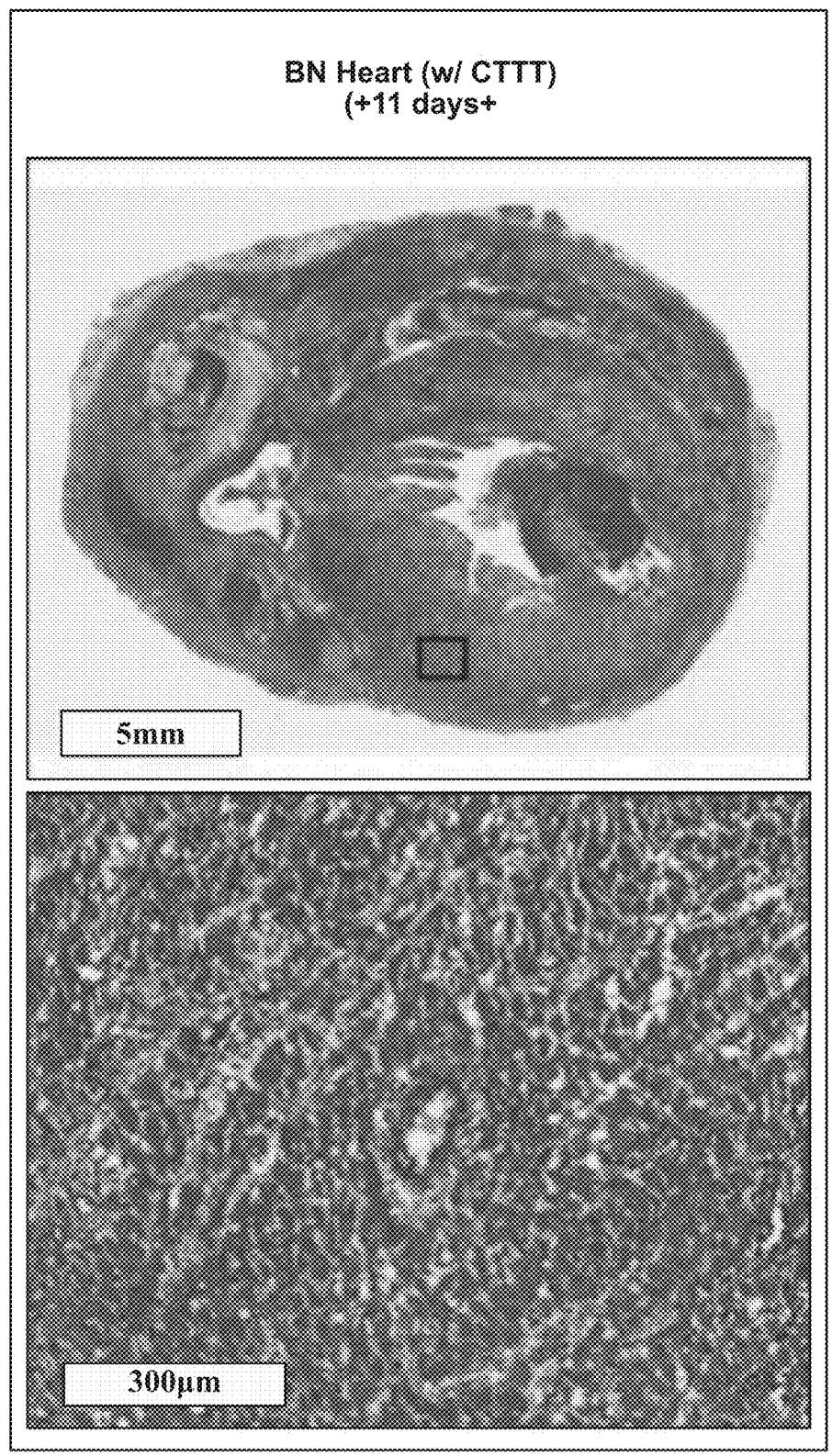
FIG. 28A and FIG. 28B are photographs of BN heart tissue with (FIG. 28A) and without (FIG. 28B) CTT insertions at 11 and 46 days, respectively. These pictures are the basis of the data in FIG. 27 and FIG. 29. The heart in FIG. 28A is not rejected because of tolerance. The heart in FIG. 28B is not rejected because of immunodeficiency from lack of thymus. This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.
Figure 28B:
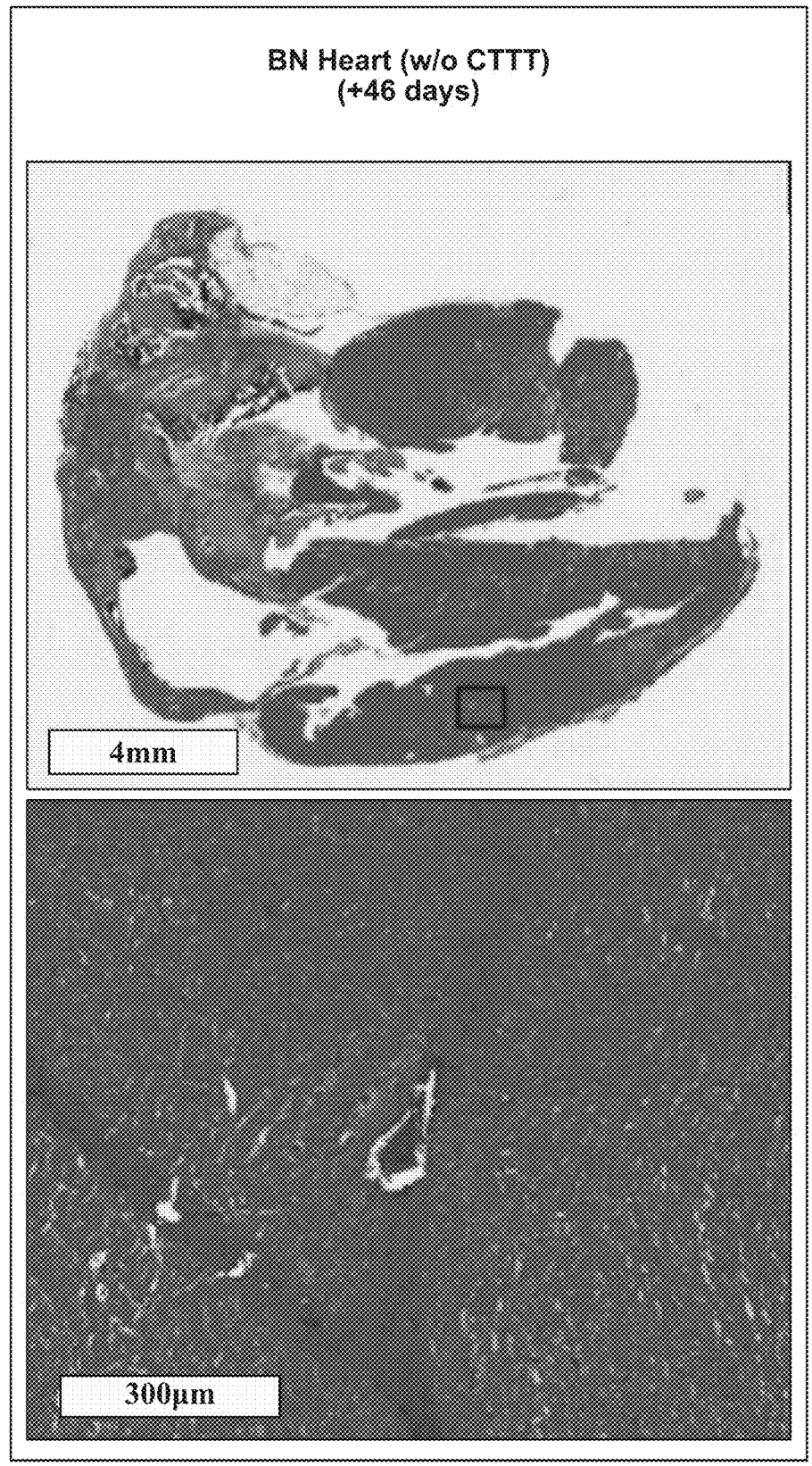

In accordance with this lack of rejection of the third party heart, histological analysis confirmed that animals with CTT inserted (upside down filled triangles, FIG. 27) showed increased mononuclear cell infiltration in the heart allograft (FIG. 28A), while animals without CTT inserted showed a pristine BN heart allograft (FIG. 28B). Recipients with CTT rejected the BN heart rapidly (MST=10±1.0 days) (filled squares, FIG. 29), while recipients without CTT did not reject the third-party BN hearts (dashed triangles, FIG. 29). The BN control (filled circles, FIG. 29) shows rejection of BN hearts by LW rats. The syngeneic control (open circles, FIG. 29) shows lack of rejection of LW hearts by LW rats. Kaplan-Meier survival curve (FIG. 27) showed significant differences in the graft survival. Representative scanned images of explanted BN heart graft at the time of rejection or 46 days post-transplantation are shown in FIGS. 28A and 28B, respectively. BN heart grafts from animals with CTT inserted showed severe mononuclear cell infiltration (FIG. 28A), while BN heart grafts from animals without CTT inserted showed no sign of rejection (FIG. 28B). Images were adapted from whole slide scan.

Figure 29:
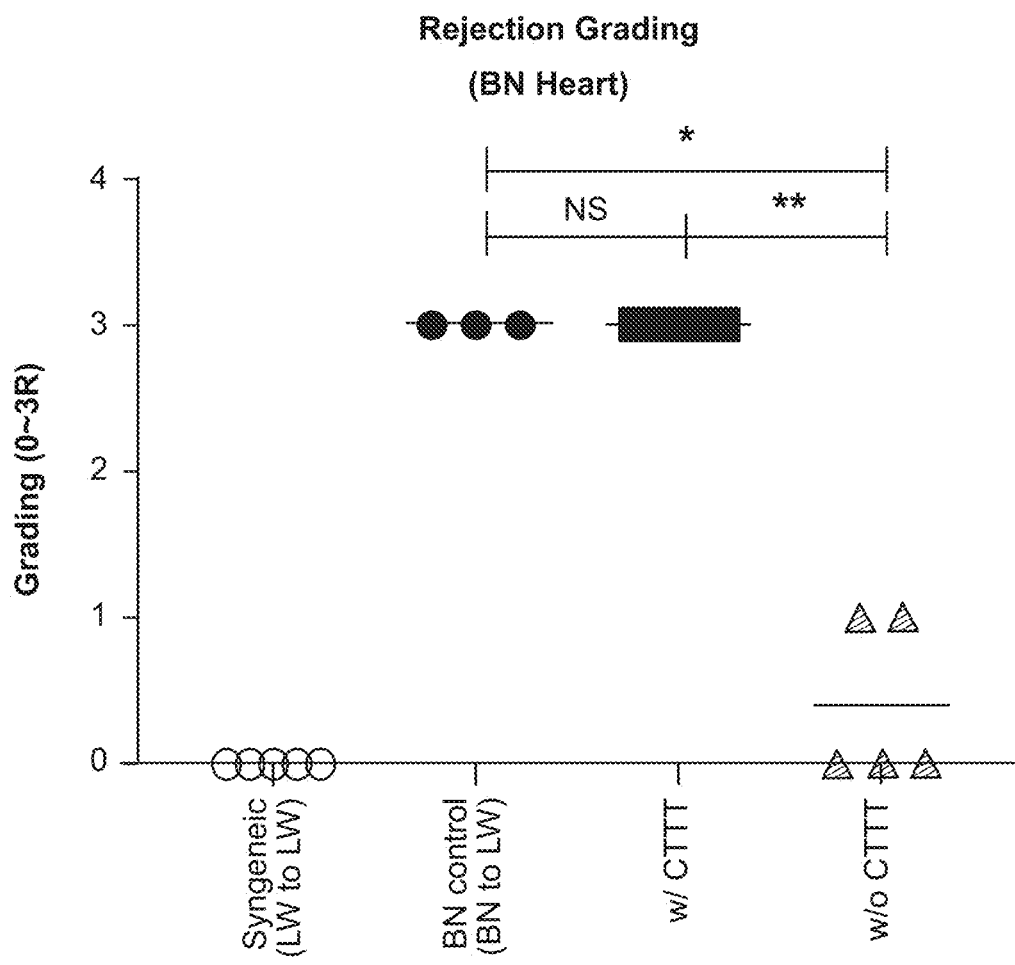
FIG. 29 shows rejection grading of the cervical BN hearts. Syngeneic L W hearts placed into LW rats (open circles) were not rejected. BN hearts placed into LW rats (filled circles) were rejected. BN hearts placed in LW rats who received CTT were rejected (filled squares). BN hearts placed in LW rats who did not receive CTT were weakly rejected (shaded triangles) in 2 rats and not rejected by the other three rats. These data show that the rats with CTT were able to strongly reject $3^{rd}$ party hearts even while they accepted DA hearts (FIG. 26C) as the CTTT expressed DA. The rats without CTT were immunodeficient and didn't reject either the DA (FIG. 26C) or the BN hearts. This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.

Histological analysis (ISHLT grading) of explanted BN hearts from rats with CTT inserted (filled squares, FIG. 29) showed grade 3R rejection with significantly increased inflammatory cell infiltration compared to syngeneic controls or rats without CTT inserted (shaded triangles, FIG. 29). ISHLT grading showed significantly higher rejection grading from BN hearts from animals with CTT compared to BN hearts from animals without CTT (n=3-5 per group). Mann-Whiney U test, *P<0.05; **P<0.01; NS, not significant (p>0.05).

Figure 30A:
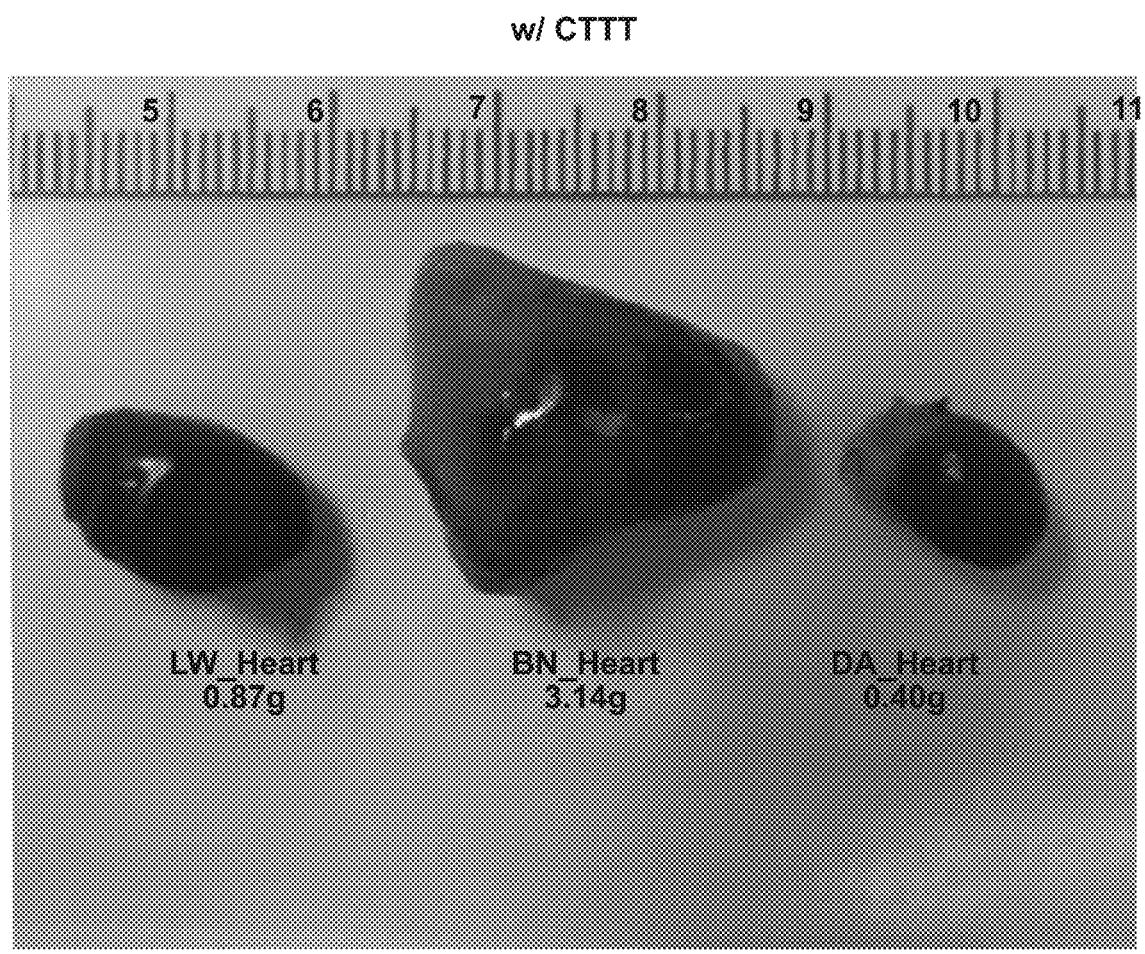
FIG. 30A and FIG. 30B are photographs of BN hearts in which rats received or did not receive CTT insertions compared to LW and DA hearts, respectively.
Figure 30B:
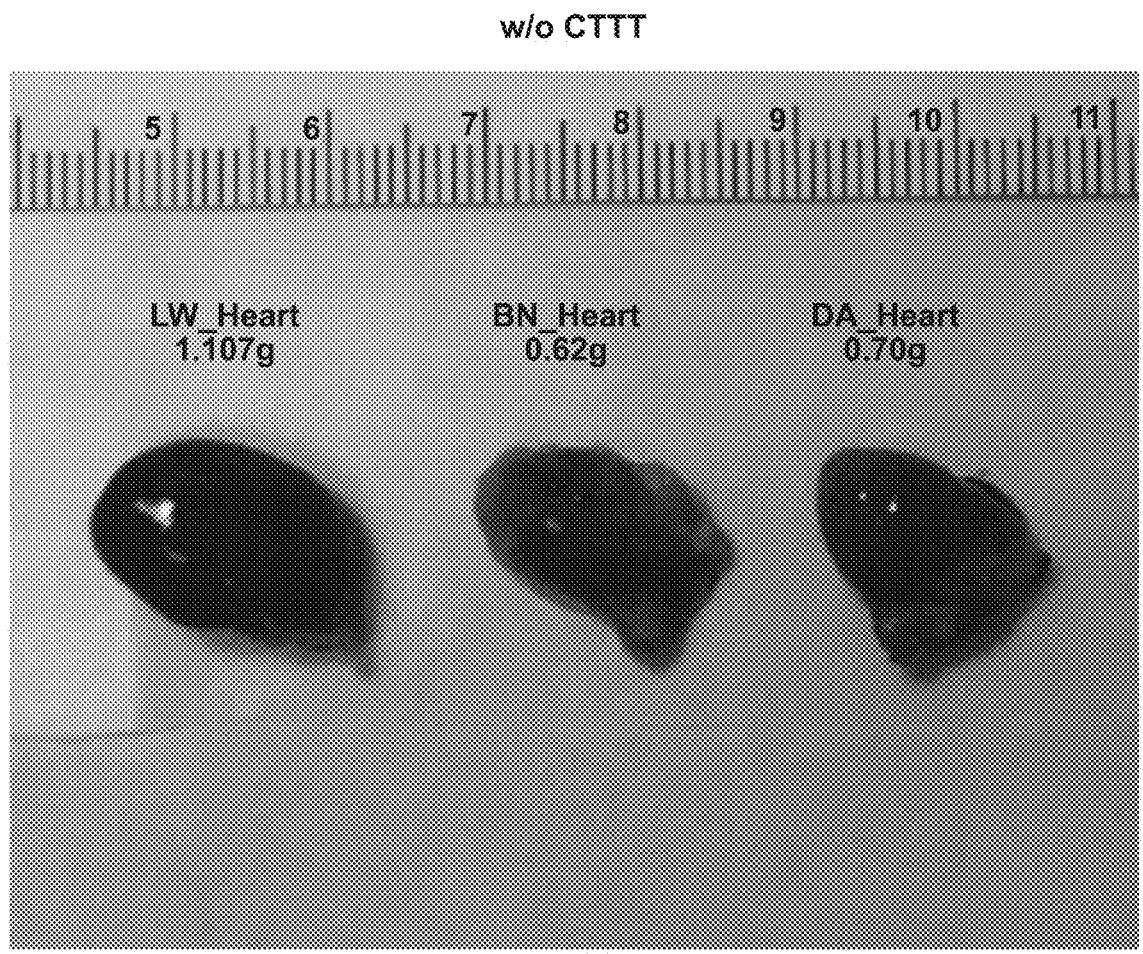

It is also notable that the cervical BN hearts in the recipients with CTT inserted were greatly enlarged (FIG. 30A), while the abdominal DA hearts were smaller than the native hearts (FIG. 30A). BN hearts from recipients without CTT inserted did not show any increase in size (FIG. 30B) compared to BN hearts from recipients with CTT.

Selective T Cell Infiltration in the Third-Party Hearts but not in the DA Hearts that Shared the DA MHC of the CTT Two conventional ways were used to define graft rejection in this rat heart transplantation model: heart beating/cessation measurements and the ISHLT human grading system. The former is insensitive with respect to low-grade rejection, while the latter is insensitive with respect to high-grade rejection. As a result, inflammatory cell infiltration was measured in DA hearts from 3 rats at day 180 and in BN hearts at the time of sacrifice at 7 to 8 months in 5 rats. Inflammatory cell infiltration was therefore measured in DA hearts from 3 rats at day 180 and in BN hearts at the time of sacrifice at 7 to 8 months in 5 rats.

Figure 31B:
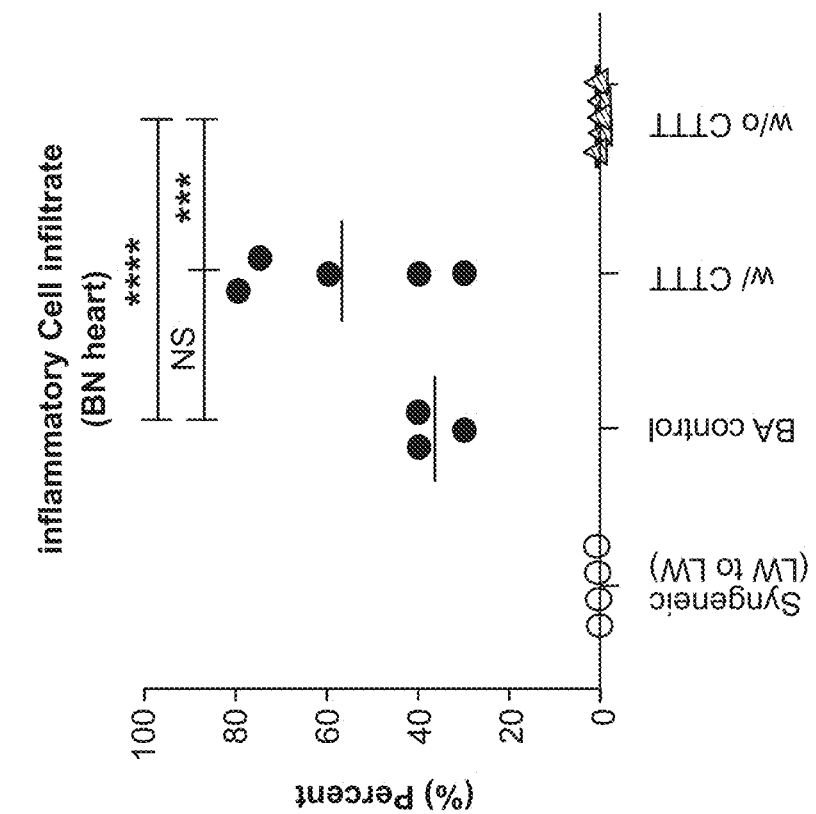
FIG. 31A and FIG. 31B are plots of rejection grading for explanted cervical BN hearts from rats with and without CTT insertions vs. BN controls and syngeneic control rats.
Figure 31A:
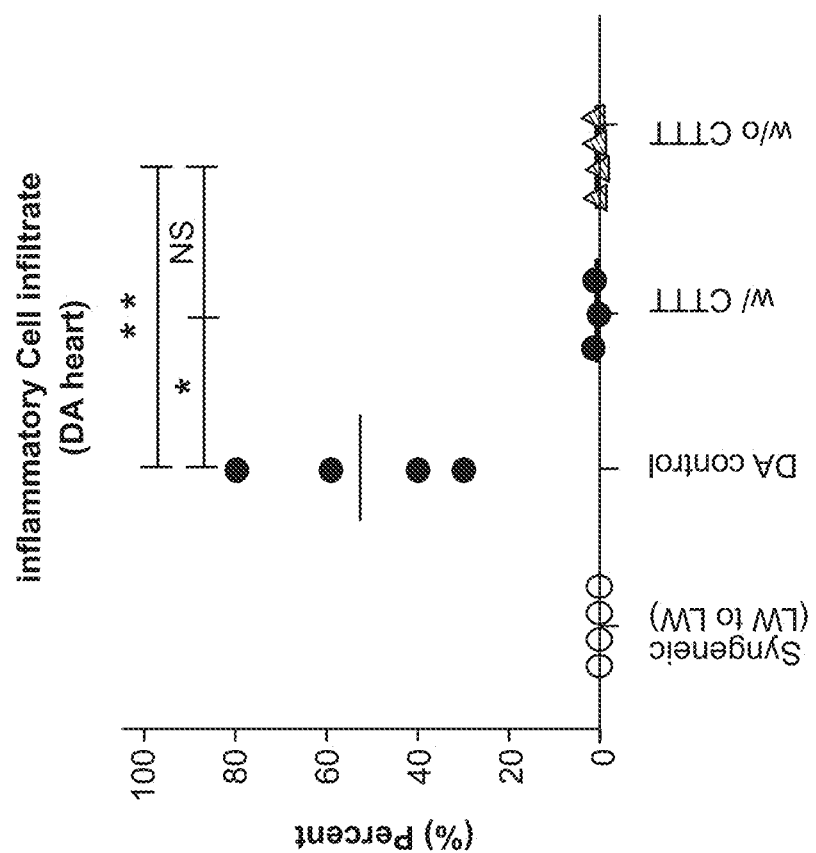

Rats that were treated with T cell depletion, surgical insertion of CTT, and CsA administered for four months, did not show an increased level of inflammatory cell infiltration in the DA hearts after T cell repopulation (FIG. 31A). DA control grafts (in LW rats with no immunosuppression) showed a significantly increased graft infiltration of immune cells in the DA heart compared to the infiltration of immune cells in DA hearts in rats with CTT or without CTT. Animals inserted with CTT showed massive inflammatory cell infiltration in the third-party cardiac allograft (BN heart) (FIG. 31B). The BN control grafts (in LW rats with no immunosuppression) and BN grafts from recipients with CTT showed significantly elevated inflammatory cell infiltration compared to those in BN grafts from animals without CTT. Rats not inserted with CTT showed no infiltrates in the BN heart (FIG. 31B) shaded triangles) because of their immunoincompetence.

Figure 31C:
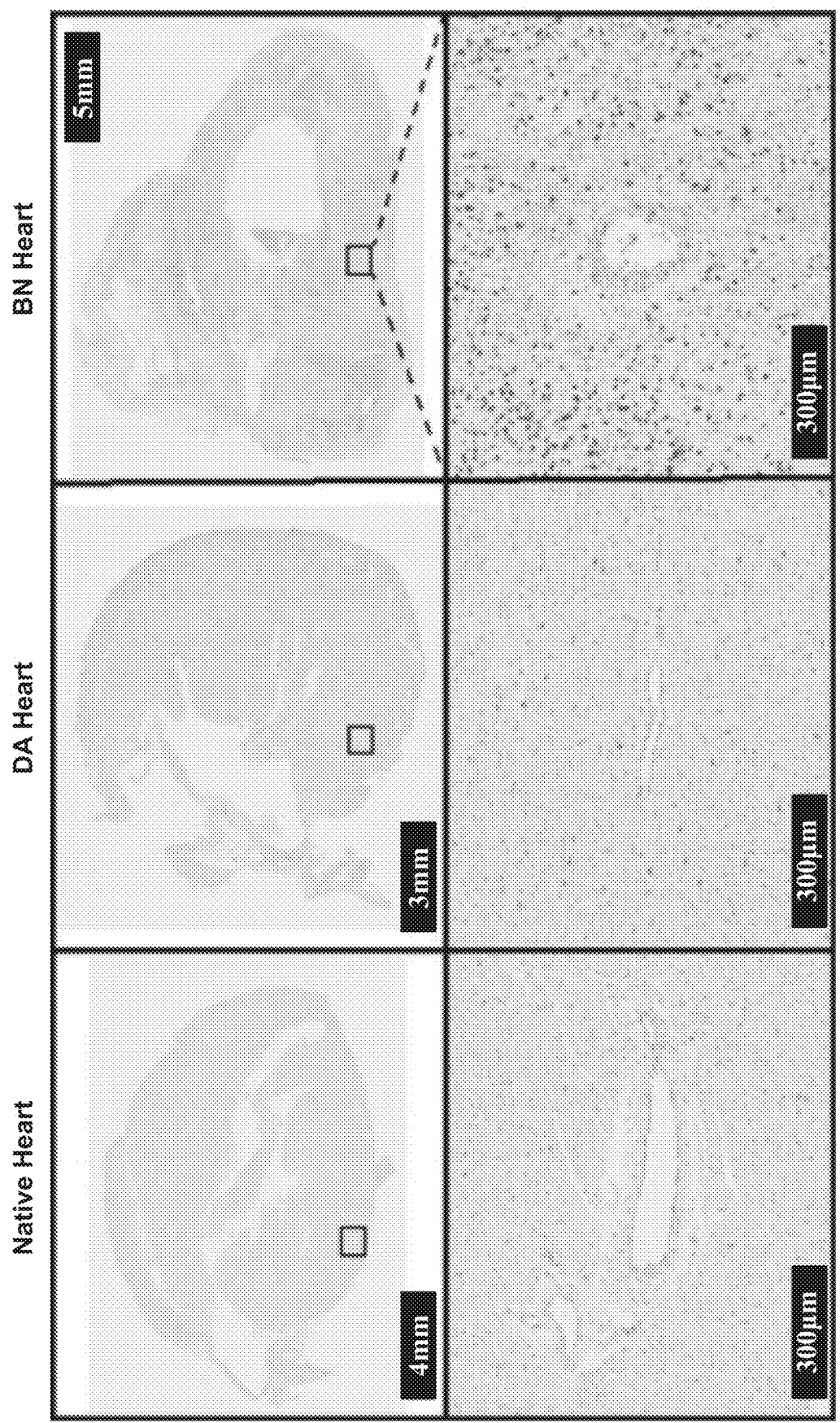
FIG. 31C shows DA and BN heart rats that were harvested from the LW recipients along with the native LW heart at the time of the cervical BN heart rejection. The lower right panel shows the T cells (brown) in the BN heart leading to its rejection.
Figure 31D:
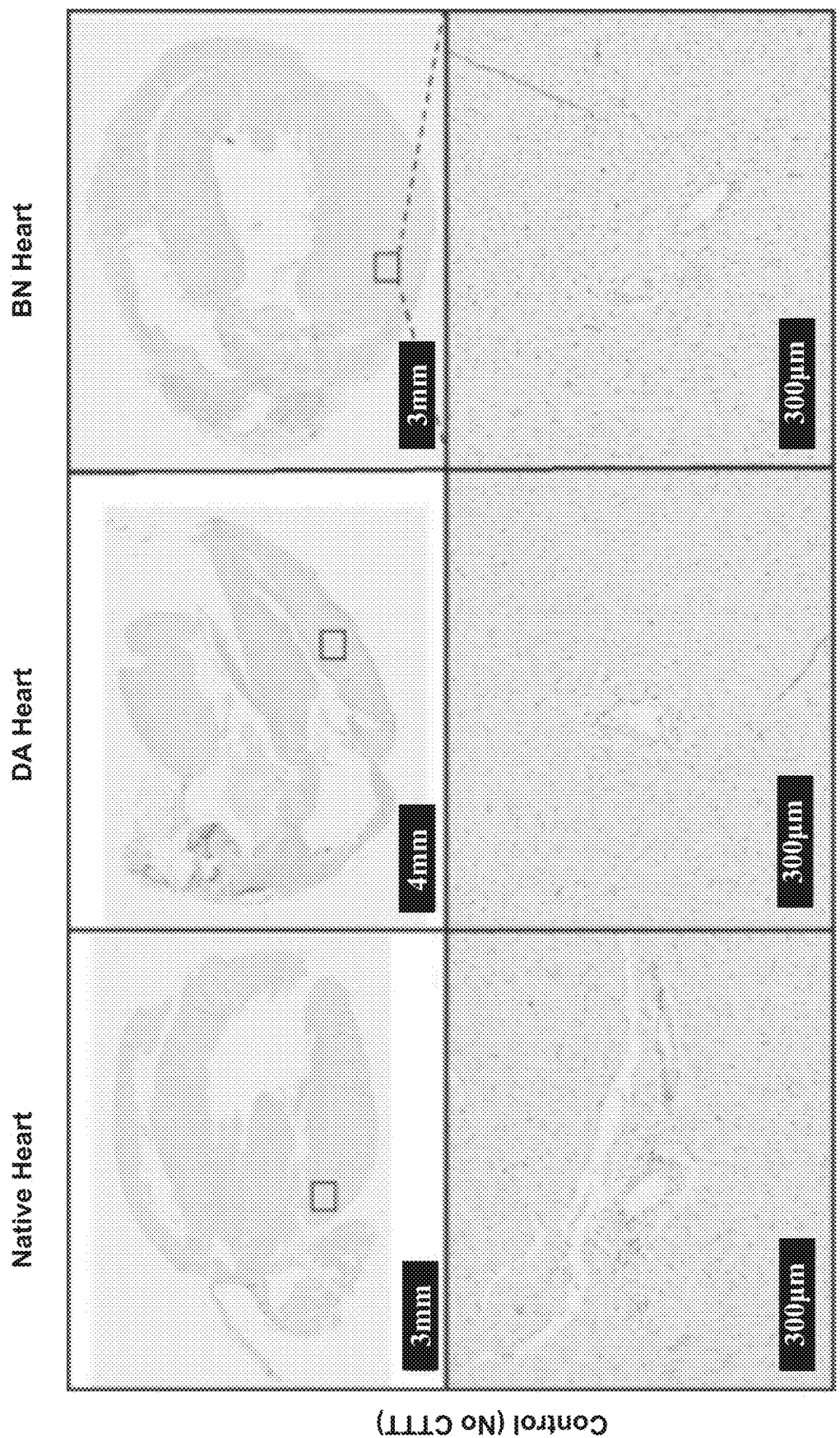
FIG. 31D shows T cell infiltration in the LW, DA, and BN hearts from control animals without insertion of CTT. There is no T cell infiltration because the animals are immunodeficient. This figure is taken from a manuscript in preparation for submission for publication: Kwun J, Li J, Rouse D C, Park J, Farris A B, Turek J W, Knechtle S J, Kirk A D, Markert M L Cultured Thymus Transplantation Promotes Donor-specific Tolerance to Allogeneic Heart Transplants.

T cell infiltration was evaluated with immunohistochemistry and confirmed a selective T cell infiltration in the BN (right hand panels, FIG. 31C), but not DA (middle panels, FIG. 31C) hearts of the animals inserted with CTT and a lack of T cell infiltration in both hearts of animals without CTT inserted (FIG. 31D). Heart allografts from DA and BN rats were harvested with native heart at the time of BN heart rejection. Grossly, native heart and DA heart (POD 196) did not show dramatic increase of T cells, while BN heart (POD14) showed a massive amount of T cells in recipients with CTT inserted. Images were adapted from whole slide scan. Total 3-5 animals per group were analyzed; student's t-test, *P<0.05; P<0.01; *P<0.001, ****P<0.0001; NS, not significant (p>0.05).

These data confirm that for the group receiving CTT the T cell infiltration occurs only in the third-party BN graft, but not in the graft sharing MHC (DA) with the transplanted thymus, possibly due to lack of T cell repertoire (by negative selection) against (DA heart) donor antigens.

Humoral Response Against Donor Antigens after Thymus Transplantation

Anti-donor antibody responses were evaluated to determine whether the allogeneic T cell unresponsiveness noted in thymectomized LW rats followed by LW×DA transplants and the surgical insertion of CTT, was associated with humoral tolerance against donor DA MHC. Serially collected recipient serum samples were collected and flow cross-match with PBMCs from DA and BN rats was performed. Animals that received DA or BN heart transplants without immunosuppression developed antibody against their donors (DA or BN, respectively). Animals with a syngeneic cardiac allograft did not produce antibody against either DA or BN MHC, as reported in FIG. 32A (horizontal shaded peaks in the left hand column, on top for DA, and on the bottom for BN). Representative histogram plots for post-transplant donor-specific alloantibody (anti-DA and anti-BN antibodies) measured by T cell flow cross-match are shown in FIG. 32A. Recipients with or without CTT did not generate any antibodies against DA antigen (the top row, middle and right hand columns in FIG. 32A), while animals with CTT were able to generate antibody against BN antigen (lower row, middle panel, FIG. 32A). Serum samples from recipients of DA heart transplantation without immunosuppression and from LW recipients of BN heart transplantation without immunosuppression were used as positive controls (DA control and BN control) for anti-DA (top row, left panel, bold line or anti-BN antibody (bottom row, left panel, dashed line), respectively.

Figure 32B:
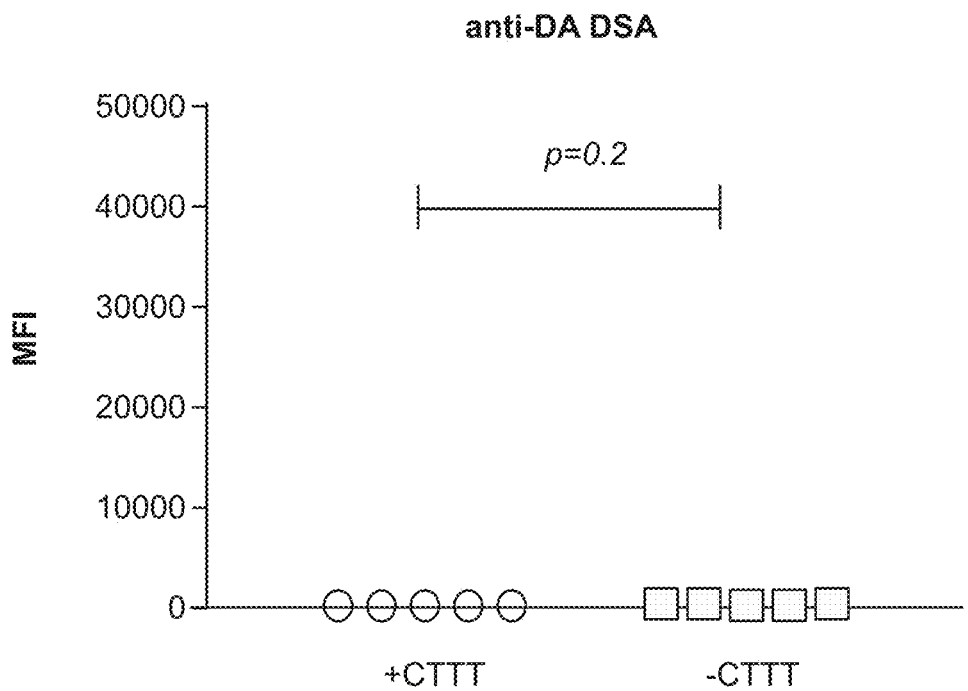
Figure 32C:
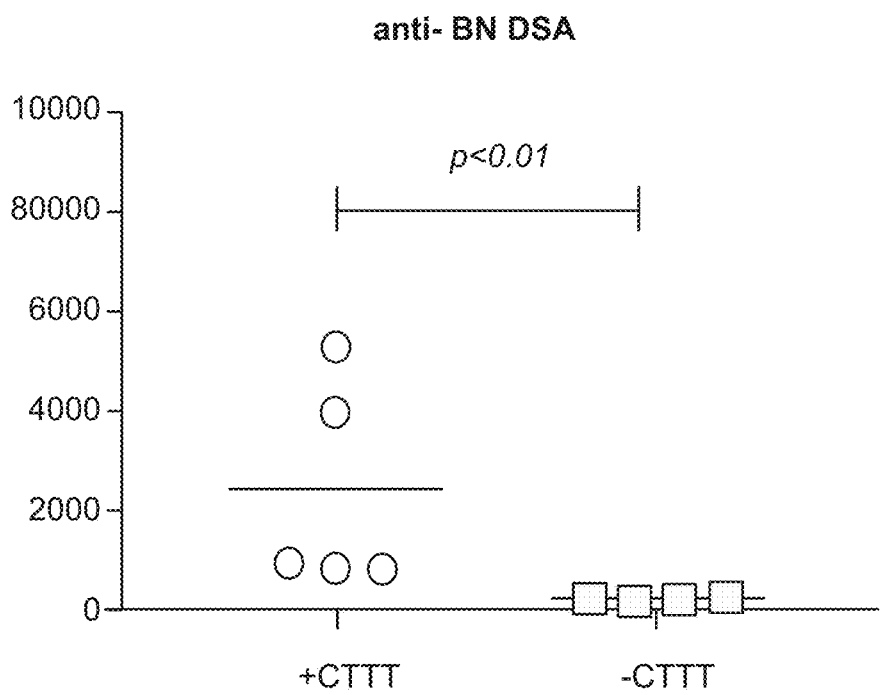
Figure 33A:
FIGS. 33A-P. Cryopreservation of non-human primate cultured thymus tissue after 12 days of culture. The top row is cytokeratin at harvest (FIG. 33A), day 6 of culture (FIG. 33B), day 12 of culture (FIG. 33C), and after 12 days of culture followed by 35 days cryopreservation then thawing for the photo (FIG. 33D). The cytokeratin (AE1/AE3) in FIG. 33D resembles the cytokeratin in FIG. 33C. The second row shows CK14 staining with the same time points in FIG. 33E (harvest), FIG. 33F (day 6 of culture), FIG. 33G (day 12 of culture) and FIG. 33H (after 12 days of culture followed by 35 days of cryopreservation then thawing), respectively. The CK14 in FIG. 33H is very similar to that in panel FIG. 33G. The third row shows CD3 staining in FIG. 33I, FIG. 33J, FIG. 33K and FIG. 33L at the same time points, which has the expected loss of viable T cells through time. Panel
Figure 33B:
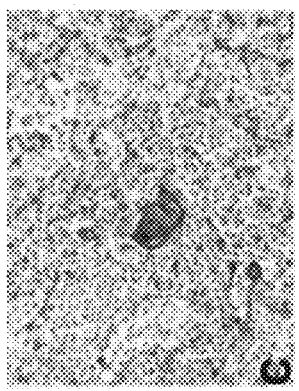
FIG. 33L is similar to panel FIG. 33K in having very few T cells. The fourth row FIG. 33M, FIG. 33N, FIG. 33 O
Figure 33C:
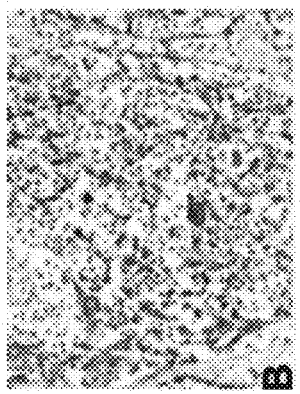
Figure 33D:
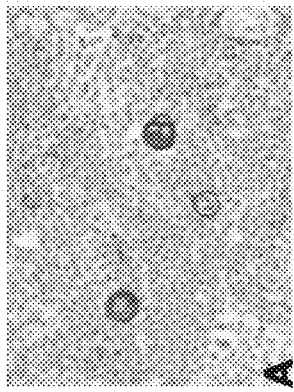
Figure 33E:
Figure 33F:
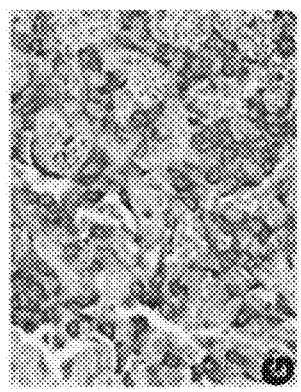
Figure 33G:
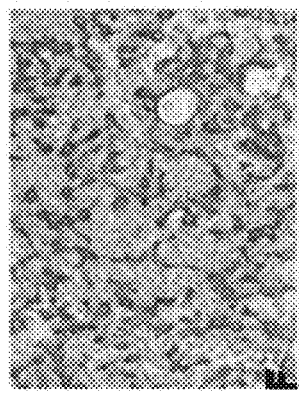
Figure 33H:

Interestingly, similar to T cell hypo-responsiveness, no anti-DA Ab was detected in animals with or without CTTT (FIG. 32B). Anti-BN Ab was readily detected in animals with LW×DA with CTT inserted, but not in animals without CTT inserted, p<0.01 (FIG. 32C). The animals without CTT were generally immunodeficient. The animals with CTT had specific tolerance to DA.

Taken together, thymus co-transplantation resulted in specific tolerance to the allogeneic DA MHC expressed in the donor thymus, and thus long-term survival of the DA heart transplant via preventing development of both the donor-specific anti-DA T cell repertoire as well as preventing the donor (DA)-specific humoral response. Immunocompetence was demonstrated in these rats by the rapid rejection of third-party BN hearts as well as alloantibody response against BN donor cells.

Further support for the treatment described above may be deduced from a clinical experience with a DiGeorge anomaly patient.

Patient 1 is a child born with complete DiGeorge anomaly. He had no T cells at birth. A major problem for Patient 1 was profound hypoparathyroidism leading to many hospitalizations for hypocalcemia. Patient 1 was given both a cultured thymus tissue transplant (CTT) and a parental parathyroid gland transplant on the same day. There were three other patients given thymus plus parental parathyroid in a small clinical trial. Patient 1 received the two transplants at 4 months of life. Although Patient 1 had no T cells, Patient 1 was given RATGAM for immunosuppression prior to transplantation per protocol. No other immunosuppression was given. Patient 1 developed naïve T cells and normal proliferative T cell responses to mitogens. All four patients who received both thymus and parathyroid in the trial developed normal parathyroid hormone levels. Patient 1 was the only subject who was able to come off calcium supplementation long term (10 years). Of the three other Patients, one died prior to one year from pulmonary problems, and the other two with complete DiGeorge anomaly had to return to calcium supplementation by approximately one year. Patient 1 was the only subject who had a negative mixed lymphocyte reaction (MLR) against the parental parathyroid donor at all time points. The other three subjects had positive MLRs starting with their first assay.

The possible explanation for Patient 1 maintaining parathyroid function is that the parathyroid donor of Patient 1 had HLA-Class II alleles that matched either the recipient Class II alleles ("*" in Table 9 below) or the thymus donor Class II alleles ("*" in Table 9 below).

The stem cells in Patient 1 developed into thymocytes in the thymus gland.

Dentritic cells from Patient 1 migrate to the thymus and delete T cells that bind tightly to the MHC on patient 1 DCs. There is tolerance to the alleles marked "*" in Table 9 below. See Table 9.

The thymus donor thymic epithelial cells also delete thymocytes that bound tightly to them (marked "*" in Table 9 below). This is the mechanism of tolerance toward the alleles marked "*" in Table 9 below.

TABLE 9

|  | HLA-A | HLA-B | HLA-C | HLA-DRB1 | HLA-DQB1 | HLA-DQA1 | HLA-DPB1 |
|---|---|---|---|---|---|---|---|
| Patient 1 | 24:02* | 08:01 | 07:02 | 03:01 | 02:01 | nt | 04:01 |
|  | 02:01* | 44:05* | 02:02* | 16:01* | 05:02* | Nt* | 04:02* |
| Parathyroid Donor | 02:01* | 44:05* | 02:02* | 16:01* | 05:02/05* | 01:02* | 04:02* |
|  | 24:01* | 35:03 | 04:01 | 11:04‡ | 03:01/19‡ | 05:05/09‡ | 04:02‡ |

TABLE 9-continued

|  | HLA-A | HLA-B | HLA-C | HLA-DRB1 | HLA-DQB1 | HLA-DQA1 | HLA-DPB1 |
|---|---|---|---|---|---|---|---|
| Thymus | 02:01* | 44:03 | 02:02 | 11:01‡ | 03:01‡ | 05:05/09‡ | 04:01‡ |
| Donor | 32:01 | 40:02 | 14:03 | 04:05 | 03:03 | 03:02/03 | 02:01 |

Of note, one can see that there is one HLA-B and one HLA-C allele in the parathyroid donor that were not matched to the recipient nor to the thymus donor. We did not understand why the parathyroid gland was not rejected. However, after 10 years passed, the child was given a live measles/mumps/rubella vaccine. The parathyroid function was destroyed within two weeks and Patient 1 returned to calcium supplementation.

We conclude that the live vaccine activated the CD8 T cells in Patient 1. One third of CD8 T cells have inherent alloreactivity. The alloreactive CD8 T cells would have reacted against the mismatched HLA-B and C alleles in the parathyroid donor (large bold HLA-B and HLA-C alleles in Table 9).

With the data from this patient, it is clear that matching for both Class I and Class II are needed to induce long term tolerance. In addition, one can see from the $2^{nd}$ field mismatches (bold italics) in DRB1 and DPB1 between the parathyroid donor and the thymus donor, that $2^{nd}$ field mismatches can be permissive and allow tolerance to form. In particular these $2^{nd}$ field mismatches did not lead to failure of graft function; they were permissive. This child is thriving with good T cell numbers and function and normal immunoglobulin levels. Patient 1, however, remains on calcium, as the parental parathyroid gland was rejected.

The foregoing embodiments and advantages are merely exemplary and are not to be construed as limiting the present invention. The present teachings can be readily applied to other types of apparatuses, experiments and surgical procedures. Also, the description of the embodiments of the present invention is intended to be illustrative and not to limit the scope of the claims. Many alternatives, modifications, and variations will be apparent to those skilled in the art.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

References discussed in the application, which are incorporated by reference in their entirety, for their intended purpose, which is clear based upon its context.

All patents, patent applications and publications cited herein are hereby incorporated by reference in their entirety. The disclosures of these publications in their entireties are hereby incorporated by reference into this application.

The disclosures of each and every patent, patent application, publication, and accession number cited herein are hereby incorporated herein by reference in their entirety.

While present disclosure has been disclosed with reference to various embodiments, it is apparent that other embodiments and variations of these may be devised by others skilled in the art without departing from the true spirit and scope of the disclosure. The appended claims are intended to be construed to include all such embodiments and equivalent variations.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

REFERENCES

Ahonen, P., 1985, "Autoimmune polyendocrinopathy—candidosis—ectodermal dystrophy (APECED): autosomal recessive inheritance," Clinical Genetics, 27: 535-542Ahonen, P., et al., 1987, "Adrenal and steroidal cell antibodies in patients with autoimmune polyglandular disease type I and risk of adrenocortical and ovarian failure," J. Clin. Endocrinology and Metabolism, 64: 494-500.

Ahonen, P., et al., 1987, "Adrenal and steroidal cell antibodies in patients with autoimmune polyglandular disease type I and risk of adrenocortical and ovarian failure," J. Clin. Endocrinology and Metabolism, 64: 494-500.

Ahonen, P., et al., 1988, J. Clin. Endocrinology and Metabolism, 66, 1152-1157.

Ahonen, P., et al., 1990, "Clinical variation of autoimmune polyendocrinopathy-candidiasis-ectodermal dystrophy (APECED) in a series of 68 patients," New Engl. J. Med. 322: 1829-1836.

Arulanantham, K., et al., 1979, "Evidence for Defective Immunoregulation in the Syndrome of Familial Candidiasis Endocrinopathy," New Eng. J. Med. 300:164-168.

Blizzard, R. M. and Kyle M., 1963, "Studies of the Adrenal Antigens and Antibodies in Addison's Disease," J. Clin. Invest. 42: 1653-1660Boehm T, Takahama Y. 2014. Thymic Development and Selection of T Lymphocytes. Heidelberg: Springer-Verlag.

Boehm T, Takahama Y. 2014. Thymic Development and Selection of T Lymphocytes. Heidelberg: Springer-Verlag.

CFR Title 21; 1271 Human cells, tissues, and cellular and tissue-based products.

Chinn I, Devlin B, Li Y J, et al., 2008. "Long-term tolerance to allogeneic thymus transplants in complete DiGeorge anomaly," Clin Immunol. 126(3): 277-281.

Heron I., 1971, "A technique for accessory cervical heart transplantation in rabbits and rats," Acta Pathol Microbiol Scand A 79(4):366-372.

Hong R, Schulte-Wissermann H, Jarrett-Toth E, Horowitz S D, Manning D D, "Transplantation of cultured thymic fragments. II. Results in nude mice," J Exp Med. 149(2): 398-415.

Li B, Li J, Hsieh C S, Hale L P, Li Y J, Devlin B H, Markert M L. 2009 "Characterization of cultured thymus tissue used for transplantation with emphasis on promiscuous expression of thyroid tissue-specific genes," 2009, Immunol Res. 2009, 44(1-3):71-83.

Li B, Li J, Devlin B H, Markert M L. 2011, "Thymic microenvironment reconstitution after postnatal human thymus transplantation," *Clin Immunol. September;* 140 (3): 244-59.

Krohn, K., et al., 1992, "Identification by molecular cloning of an autoantigen associated with Addison's disease as steroid 17α-hydroxylase," *Lancet* 339:770-773.

Markert M L, Kostyu D D, Ward F E, McLaughlin™, Watson T J, Buckley R H, Schiff S E, Ungerleider R M, Gaynor J W, Oldham K T, Mahaffey S M, Ballow M, Driscoll D A, Hale L P, Haynes B F. "Successful formation of a chimeric human thymus allograft following transplantation of partially HLA-matched postnatal thymus," 1997, *Journal of Immunology,* 158:998-1005.

Markert M L, Boeck A, Hale L P, Kloster A L, McLaughlin™, Batchvarova M N, et al., "Transplantation of thymus tissue in complete DiGeorge syndrome," 1999, *N Engl J Med.* 341(16): 1180-9.

Markert M L, et al., 2004, "Postnatal thymus transplantation with immunosuppression as treatment for DiGeorge syndrome," *Blood* 104(8):2574-2581.

Markert M L, Devlin B H, Alexieff M J, Li J, McCarthy E A, Gupton S E, et al., "Review of 54 patients with complete DiGeorge anomaly enrolled in protocols for thymus transplantation: outcome of 44 consecutive transplants," 2007, *Blood,* 109(10): 4539-47.

Markert M L, et al., 2008), "Use of allograft biopsies to assess thymopoiesis after thymus transplantation." *J Immunol* 180(9):6354-6364.

Markert M L, Devlin B H, McCarthy E A, 2010, "Thymus transplantation," *Clin Immunol.,* 135(2): 236-46.

Markert M L, Devlin B H, McCarthy E A. *Chapter 84 Thymic reconstitution.* 2013. In: Fleisher T A, Shearer W T, Schroeder H W, Frew A J, Wey and CM, editors. Clinical Immunology (Fourth Edition). London pp. 1032-8.

Markert M L. 2014. "Thymus Transplantation," *Stiehm's Immune Deficiences,* eds Sullivan K E & Stiehm E R (Academic Press), 1st Ed, pp 1059-1067.

Markert M L, Watson T J, Kaplan I, Hale L P, Haynes B F, "The human thymic microenvironment during organ culture," 1997, *Clin Immunol Immunopathol.,* January; 82(1): 26-36.

Neufeld, M. et al., 1981, "Two types of autoimmune Addison's disease associated with different polyglandular autoimmune (PGA) syndromes," *Medicine* 60: 355-362.

Parker W, Yu P B, Holzknecht Z E, Lundberg K, Buckley R H, Platt J L, "Specificity and function of 'natural' antibodies in immunodeficient subjects: Clues to B cell lineage and development," 1997, *J Clin Immunol.,* 17:311-321.

Perheentupa J., 2002, *Endocrinol. Metab. Clin. North Am.* 31: 295-320Rota I A and Dhalla F. FOXN1 deficiency nude severe combined immunodeficiency. Orphanet Journal of Rare Diseases. 2017; 12:6.

Rendell V R, Giamberardino C, Li J, Markert M L, & Brennan T V, 2014, "Complete thymectomy in adult rats with non-invasive endotracheal intubation," *J Vis Exp* (94).

Schmid C, Binder J, Heemann U, & Tilney N L, 1994, "Successful heterotopic heart transplantation in rat," *Microsurgery* 15(4):279-281.

Schoenecker J G, Hauck R K, Mercer M C, Parker W, Lawson J, 2000, "Exposure to topical bovine thrombin during surgery elicits a response against the xenogeneic carbohydrate galactose α1-3Galactose," *J Clin Immunol.,* 20:434-444.

Uibo R., et al., 1994, "Autoantibodies to cytochrome P450 enzymes P450scc, P450c17, and P450c21 in autoimmune polyglandular disease types I and II and in isolated Addison's disease," *J. Clin. Endocrinol. Metab.* 78: 323-328.

Zlotogora, J., et al., 1992, "Polyglandular autoimmune syndrome type I among Iranian Jews," *J. Med. Genet,* 29, 824-826.

Abbreviations

AIRE: autoimmune regulator gene.
Ab: Antibody.
Ag: Antigen.
APC: Antigen Presenting Cell.
ATG: thymoglobulin.
b.i.d.: twice daily
BMI body weight index
BSA: body surface area.
BSC: biological safety cabinet.
cDGA: complete DiGeorge anomaly.
CFR: Code of Federal Regulations.
CK: cytokeratin.
CNI: calcineurin inhibitor.
CTT: allogeneic cultured postnatal thymus tissue-derived product.
CVVHD/F: continuous veno-venous hemodiafiltration.
DC: Dendritic Cell.
DSA: Donor-specific Antibody.
DGF: Delayed Graft Function
EBV: Epstein Barr virus.
EU: endotoxin unit.
FBS: fetal bovine serum.
FDA: Food and Drug Administration.
FSGS: focal segmental glomerulosclerosis.
H&E: Hematoxylin and Eosin.
HD: hemodialysis.
HEPES: N-2-Hydroxyethyl peperazine N'-2-ethanesulfonic acid.
HI: HI—Heat inactivation.
HIP: Intraperitoneal.
HIV: human immunodeficiency virus.
IBW: ideal body weight.
IDDM: insulin dependent diabetes mellitus.
ISHLT: International Society for Heart & Lung Transplantation.
ISO: International Organization for Standardization.
LAL: limulus amebocyte lysate.
mAb: monoclonal antibody.
MHC: Major Histocompatibility Complex.
MST: mean survival time.
PBMC: peripheral blood mononuclear cells.
PBS: phosphate buffered saline.
POD: Post-Operative Day.
PRA: panel reactive antibodies.
SL: sublingual.
TBW: total body weight
TC: tissue culture.
Tfh: T follicular helper.
TOM: thymus organ medium.
USP: United States Pharmacopeia.

What is claimed is:

1. A method for promoting donor-specific tolerance to an allogeneic solid organ transplant obtained from a human donor, in a human recipient in need of a solid organ transplant, the method comprising the steps of:

(a) removal of the thymus of the recipient;
(b) treating the recipient with an induction immunosuppressive regimen comprising one or more immunosuppressive agent to deplete the recipient's T cells and/or to suppress the recipient's T cells from rejecting the transplanted solid organ;
(c) providing a suitable solid organ from a human donor;
(d) transplanting the solid organ into the recipient;
(e) treating the recipient with a maintenance immunosuppressive regimen;
(f) providing a cryopreserved allogeneic cultured postnatal thymus tissue-derived product maintained in a cryopreserved allogeneic cultured postnatal thymus tissue-derived product bank; wherein the cryopreserved allogeneic cultured postnatal thymus tissue-derived product is processed from thymus tissue from a thymus donor expressing HLA alleles matched to HLA alleles in the recipient that are not present in the solid organ transplant;
wherein the donor thymus tissue has been processed into donor thymus tissue slices, wherein the donor thymus tissue slices have been assessed by pathology and show >50% of areas positive for keratin in a lacy staining pattern, show Hassall bodies, show cytokeratin 14 (CK14) staining in a lacy pattern, and show >90% intact nuclei of thymic epithelial cells and other stromal cells, wherein the donor thymus tissue has been subjected to a conditioning regimen for a period up to 12 days; wherein the conditioning regimen for the donor thymus tissue comprises aseptically processing the donor thymus tissue in a thymus organ medium to produce partially T-cell depleted thymus tissue slices, wherein the partially T-cell depleted thymus tissue slices are assessed by pathology and, between day 5 and 9 of the conditioning regimen, show staining positive for keratin, show CK14 staining scattered throughout, show at least one Hassall body, and show intact nuclei of thymic epithelial cells and other stromal cells;
(g) thawing the cryopreserved allogeneic cultured postnatal thymus tissue-derived product; and
(h) implanting the thawed cryopreserved allogeneic cultured postnatal thymus tissue-derived product into the recipient, wherein the dosage of the cryopreserved allogeneic cultured postnatal thymus tissue-derived product is about 1,000-20,000 $mm^2$ of thymus tissue surface area/recipient body surface area in $m^2$, and further wherein the implanted allogeneic cultured postnatal thymus tissue-derived product induces thymopoiesis and tolerance in the recipient.

2. The method of claim 1, wherein the partially T-cell depleted donor thymus tissue slices show areas positive for cytokeratin 14 (CK14) staining upon completion of the conditioning regimen.

3. The method of claim 1, wherein the partially T-cell depleted donor thymus tissue slices show areas positive for cytokeratin 14 (CK14) staining upon completion of the conditioning regimen.

4. The method of claim 2, wherein the partially T-cell depleted donor thymus tissue slices show areas positive for cytokeratin 14 (CK14) staining upon completion of the conditioning regimen.

5. The method of claim 3, wherein the partially T-cell depleted donor thymus tissue slices show areas positive for CK14 staining in a lacy pattern upon completion of the conditioning regimen.

6. The method of claim 4, wherein the partially T-cell depleted donor thymus tissue slices show areas positive for CK14 staining in a lacy pattern upon completion of the conditioning regimen.

7. The method of claim 1, wherein the solid organ transplant is obtained from a deceased donor.

8. The method of claim 1, wherein the solid organ transplant is obtained from a living donor.

9. The method of claim 2, wherein the solid organ transplant is obtained from a deceased donor.

10. The method of claim 2, wherein the solid organ transplant is obtained from a living donor.

11. The method of claim 6, wherein the solid organ transplant is obtained from a deceased donor.

12. The method of claim 6, wherein the solid organ transplant is obtained from a living donor.

* * * * *